US011571455B2

(12) United States Patent
Hawiger et al.

(10) Patent No.: US 11,571,455 B2
(45) Date of Patent: *Feb. 7, 2023

(54) METHODS AND COMPOSITIONS FOR TREATING ALCOHOLIC LIVER DISEASE

(71) Applicant: VANDERBILT UNIVERSITY, Nashville, TN (US)

(72) Inventors: Jack Jacek Hawiger, Nashville, TN (US); Jozef Zienkiewicz, Nashville, TN (US); Danya Liu, Decatur, GA (US)

(73) Assignee: VANDERBILT UNIVERSITY, Nashville, TN (US)

( * ) Notice: Subject to any disclaimer, the term of this patent is extended or adjusted under 35 U.S.C. 154(b) by 76 days.

This patent is subject to a terminal disclaimer.

(21) Appl. No.: 16/887,860

(22) Filed: May 29, 2020

(65) Prior Publication Data

US 2021/0015893 A1 Jan. 21, 2021

Related U.S. Application Data

(60) Continuation-in-part of application No. PCT/US2019/051005, filed on Sep. 13, 2019, and a continuation-in-part of application No. 16/622,469, filed as application No. PCT/US2018/037993 on Jun. 18, 2018, application No. 16/887,860, which is a continuation-in-part of application No. 16/799,350, filed on Feb. 24, 2020, now Pat. No. 11,364,278, which is a division of application No. 15/297,996, filed on Oct. 19, 2016, now Pat. No. 10,568,928, which is a division of application No. 14/251,135, filed on Apr. 11, 2014, now Pat. No. 9,492,544.

(60) Provisional application No. 62/733,997, filed on Sep. 20, 2018, provisional application No. 62/731,394, filed on Sep. 14, 2018, provisional application No. 62/521,159, filed on Jun. 16, 2017, provisional application No. 61/810,939, filed on Apr. 11, 2013.

(51) Int. Cl.
| | |
|---|---|
| A61K 38/16 | (2006.01) |
| C07K 14/47 | (2006.01) |
| A61K 45/06 | (2006.01) |
| A61K 38/12 | (2006.01) |
| A61K 31/167 | (2006.01) |
| A61K 31/192 | (2006.01) |
| C07K 14/50 | (2006.01) |

(52) U.S. Cl.
CPC ............ *A61K 38/16* (2013.01); *A61K 31/167* (2013.01); *A61K 31/192* (2013.01); *A61K 38/12* (2013.01); *A61K 45/06* (2013.01); *C07K 14/47* (2013.01); *C07K 14/4702* (2013.01); *C07K 14/50* (2013.01); *C07K 2319/00* (2013.01); *C07K 2319/09* (2013.01)

(58) Field of Classification Search
CPC ............ C07K 14/4702; C07K 14/4703; A61K 38/16; A61K 38/12
See application file for complete search history.

(56) References Cited

U.S. PATENT DOCUMENTS

| | | | |
|---|---|---|---|
| 5,807,746 | A | 9/1998 | Lin et al. |
| 6,043,339 | A | 3/2000 | Lin et al. |
| 6,495,518 | B1 | 12/2002 | Hawiger et al. |
| 6,624,146 | B1 | 9/2003 | Imamura et al. |
| 7,112,568 | B2 | 9/2006 | Eisenberg et al. |
| 7,553,929 | B2 | 6/2009 | Hawiger et al. |
| 7,576,058 | B1 | 8/2009 | Lin et al. |
| 8,324,148 | B2 | 12/2012 | Hawiger et al. |
| 8,420,096 | B2 | 4/2013 | Hawiger et al. |
| 8,932,559 | B2 | 1/2015 | Hawiger et al. |
| 9,044,433 | B2 | 6/2015 | Hawiger et al. |
| 9,303,000 | B2 | 4/2016 | Sandanayaka et al. |
| 9,370,549 | B2 | 6/2016 | Hawiger et al. |
| 9,388,224 | B2 | 7/2016 | Hawiger et al. |
| 9,492,544 | B2 | 11/2016 | Hawiger et al. |
| 9,808,501 | B2 | 11/2017 | Hawiger et al. |
| 10,272,133 | B2 | 4/2019 | Hawiger et al. |
| 10,568,928 | B2 | 2/2020 | Hawiger et al. |

(Continued)

FOREIGN PATENT DOCUMENTS

| | | |
|---|---|---|
| EP | 2763688 | 8/2014 |
| WO | 1997/010818 | 3/1997 |

(Continued)

OTHER PUBLICATIONS

Liu et al. ("Nuclear Import of Proinflammatory Transcription Factors Is Required for Massive Liver Apoptosis Induced by Bacterial Lipopolysaccharide", The Journal of Biological Chemistry, 2004, pp. 48434-48442 (Year: 2004).*

"Cure", Cambridge English Dictionary, available online at https://dictionary.cambridge.org/us/dictionary/english/cure, 8 pages (accessed on Apr. 24, 18) (Year: 2018).

"Heal", Cambridge English Dictionary, available online at https://dictionary.cambridge.org/us/dictionary/english/heal, 8 pages (accessed on Apr. 24, 18) (Year: 2018).

(Continued)

*Primary Examiner* — Lianko G Garyu
(74) *Attorney, Agent, or Firm* — Meunier Carlin & Curfman LLC

(57) ABSTRACT

Disclosed are compositions and methods for treating inflammation including its end-stage sepsis and conditions mediated by inflammation such as liver apoptosis and cirrhosis, thrombocytopenia, hypoglycogenemia, hyperglycemia, and hypertriglyceridemia. In one aspect, the compositions and methods disclosed herein can also be used to enhance clearance of microbes from infected tissues, organs, or systems in a subject. Also disclosed herein are compositions and methods for reducing levels of stress responsible transcription factors and metabolic transcription factors in a cell in a subject with microbial, allergic, autoimmune, metabolic, and posttraumatic inflammation.

5 Claims, 6 Drawing Sheets

Specification includes a Sequence Listing.

(56) References Cited

U.S. PATENT DOCUMENTS

| | | | |
|---|---|---|---|
| 2004/0147435 | A1 | 7/2004 | Hawiger et al. |
| 2004/0235746 | A1 | 11/2004 | Hawiger et al. |
| 2004/0258688 | A1 | 12/2004 | Hawiger et al. |
| 2009/0233843 | A1 | 9/2009 | Marin |
| 2010/0210534 | A1* | 8/2010 | Bevec .................. A61P 17/02 514/5.5 |
| 2011/0229525 | A1 | 9/2011 | Hawiger et al. |
| 2011/0319323 | A1 | 12/2011 | Schricker et al. |
| 2012/0315341 | A1 | 12/2012 | Konowalchuk et al. |
| 2014/0309159 | A1 | 10/2014 | Hawiger et al. |
| 2014/0336113 | A1 | 11/2014 | Hawiger et al. |
| 2015/0250850 | A1 | 9/2015 | Hawiger et al. |
| 2016/0354431 | A1 | 12/2016 | Hawiger et al. |
| 2017/0100454 | A1 | 4/2017 | Hawiger et al. |

FOREIGN PATENT DOCUMENTS

| | | |
|---|---|---|
| WO | 1999/049879 | 10/1999 |
| WO | 2001/037821 | 5/2001 |
| WO | 0137821 | 5/2001 |
| WO | 2009/039966 | 4/2009 |
| WO | 2011/053822 | 5/2011 |
| WO | 2013/052813 | 4/2013 |
| WO | 2013/112834 | 8/2013 |
| WO | 2014/086835 | 6/2014 |

OTHER PUBLICATIONS

Ablamunits V, Elias D, Reshef T, Cohen IR. Islet T cells secreting IFN-γ in NOD mouse diabetes: arrest by p277 peptide treatment. Journal of autoimmunity. Feb. 1, 1998;11(1):73-81.

Akira, S. and Kaisho, T., Toll-like receptors: critical proteins linking innate and acquired immunity. Nat Immunol, 2001. 2(8): p. 675-80.

Alexander, W.S., Starr, R., Fenner, J.E., Scott, C.L., Handman, E., Sprigg, N.S., Corbin, J.E., Cornish, A.L., Darwiche, R., Owczarek, C.M., Kay, T.W., Nicola, N.A., Hertzog, P.J., Metcalf, D. and Hilton, D.J., SOCS1 is a critical inhibitor of interferon gamma signaling and prevents the potentially fatal neonatal actions of this cytokine. Cell, 1999. 98(5): p. 597-608.

Alexander, W.S., Suppressors of cytokine signaling (SOCS) in the immune system. Nat. Rev. Immunol., 2002. 2(6): p. 410-6.

Angus DC, van der Poll T (2013) Severe sepsis and septic shock. N Engl J Med 369: 2063.

Askjaer, P., Galy, V., Hannak, E. and Mattaj, I.W., Ran GTPase cycle and importins alpha and beta are essential for spindle formation and nuclear envelope assembly in living Caenorhabditis elegans embryos. Mol Biol Cell, 2002. 13(12): p. 4355-70.

Bagshawe KD, Springer CJ, Searle F, Antoniw P, Sharma SK, Melton RG, Sherwood RF. A cytotoxic agent can be generated selectively at cancer sites. British journal of cancer. Dec. 1988;58(6):700-3.

Bagshawe KD. Towards generating cytotoxic agents at cancer sites. The First Bagshawe Lecture. Br. J. Cancer. 1989;60:275-81.

Baldwin, A.S., Jr., The NF-kappa B and I kappa B proteins: new discoveries and insights. Annu Rev Immunol, 1996.14: p. 649-83.

Baran-Marszak F, Feuillard J, Najjar I, Le Clorennec C, Bechet JM, Dusanter-Fourt I, et al. (2004) Differential roles of STAT1alpha and STAT1beta in fludarabine-induced cell cycle arrest and apoptosis in human B cells. Blood 104: 2475-2483.

Batey, R.G., Cao, Q. and Gould, B., Lymphocyte-mediated liver injury in alcohol-related hepatitis. Alcohol, 2002. 27(1): p. 37-41.

Battelli MG, Abbondanza A, Tazzari PL, Bolognesi A, Lemoli RM, Stirpe F. T Tymphocyte killing by a xanthine-oxidase-containing immunotoxin. Cancer Immunology, Immunotherapy. Nov. 1, 1992;35(6):421-5.

Beutler B (2004) Innate immunity: an overview. Mol Immunol 40: 845-859.

Bhatia et al.: "Insulin Therapy for Patients With Type I Diabetes", Supplement of JAPI, vol. 55 (2007) pp. 29-40.

Bode, C. and Bode, J.C., Activation of the innate immune system and alcoholic liver disease: effects of ethanol per se or enhanced intestinal translocation of bacterial toxins induced by ethanol? Alcohol Clin Exp Res, 2005, 29(11 Suppl): p. 166S-71S.

Bode, J.G., Nimmesgern, A., Schmitz, J., Schaper, F., Schmitt, M., Frisch, W., Haussinger, D., Heinrich, P.C. and Graeve, L., LPS and TNFalpha induce SOCS3 mRNAand inhibit IL-induced activation of STATS in macrophages. FEBS Lett., 1999. 463(3): p. 365-70.

Bohrer H, Qiu F, Zimmermann T, Zhang Y, Jllmer T, Mannel D, et al. (1997) Role of NFkappaB in the mortality of sepsis. J Clin Invest 100: 972-985.

Boldin, M.P., Goncharov, T.M., Goltsev, Y.V. and Wallach, D., Involvement of MACH, a novel MORT1/FADD-interacting protease, in Fas/APO-1- and TNF receptor-induced cell death. Cell, 1996. 85(6): p. 803-15.

Bonizzi, G. and Karin, M., The two NF-kappaB activation pathways and their role in innate and adaptive immunity. Trends Immunol, 2004. 25(6): p. 280-8.

Buckley CD, Gilroy DW, Serhan CN (2014) Proresolving lipid mediators and mechanisms in the resolution of acute inflammation. Immunity 40: 315-327.

Butler et al.: "Beta-Cell Deficit and Increased Beta-Cell Apoptosis in Humans With Type-2 Diabetes", Diabetes, vol. 52 (2003) pp. 102-110.

Car, B.D., Eng, V.M., Schnyder, B., Ozmen, L, Huang, S., Gallay, P., Neumann, D., Aguet, M. and Ryffel, B., Interferon gamma receptor deficient mice are resistant to endotoxic shock. J Exp Med, 1994. 179(5): p. 1437-44.

Car, B.D., Eng, V.M., Schnyder, B., Ozmen, L., Huang, S., Gallay, P., Heumann, D., Aguet, M. and Ryffel, B., Interferon gamma receptor deficient mice are resistant to endotoxic shock. J. Exp. Med., 1994. 179(5): p. 1437-1444.

Carballo, E., Lai, W.S. and Blackshear, P.J., Feedback inhibition of macrophage tumor necrosis factoralpha production by tristetraprolin. Science, 1998. 281(5379) p. 1001-5.

Chang, Jui-Yoa. "Thrombin specificity: Requirement for apolar amino acids adjacent to the thrombin cleavage site of polypeptide substrate." European journal of biochemistry 151.2 (1985): 217-224.

Charalambous BM, Leung MH (2012) Pneumococcal sepsis and nasopharyngeal carriage. Curr Opin Pulm Med 18: 222-227.

Chedid, A., Mendenhall, C.L., Moritz, T.E., French, S.W., Chen, T.S., Morgan, T.R., Roselle, G.A., Nemchausky, B.A., Tamburro, C.H., Schiff, E.R. and et al., Cell-mediated hepatic injury in alcoholic liver disease. Veterans Affairs Cooperative Study Group 275. Gastroenterology, 1993.105(1): p. 254-66.

Chinnaiyan, A.M., O'Rourke, K., Tewari, M. and Dixit, V.M., FADD, a novel death domain-containing protein, interacts with the death domain of Fas and initiates apoptosis. Cell, 1995. 81(4): p. 505-12.

Cingolani G, Petosa C, Weis K, Müller CW. Structure of importin-beta bound to the IBB domain of importin-alpha. Nature. May 20, 1999;399(6733):221-9.

Cingolani Gl, Bednenko J, Gillespie MT, Gerace L. Molecular basis for the recognition of a nonclassical nuclear localization signal by importin beta. Mol Cell. Dec. 2002;10(6):1345-53.

Couillault, C., Pujol, N., Reboul, J., Sabatier, L., Guichou, J.F., Kohara, Y. and Ewbank, J.J., TLRindependent control of innate immunity in Caenorhabditis elegans by the TIR domain adaptor protein TIR-1, an ortholog of human SARM. Nat Immunol, 2004. 5(5): p. 488-94.

Croker, B.A., Krebs, D.L, Zhang, J.G., Wormald, S., Willson, T.A., Stanley, E.G., Robb, L, Greenhalgh, C.J., Forster, L, Clausen, B.E., Nicola, N.A., Metcalf, D., Hilton, D.J., Roberts, A.W. and Alexander, W.S., SOCS3 negatively regulates IL-6 signaling in vivo. Nat. Immunol., 2003. 4(6): p. 540-5.

Dąbek, Józefa, Andrzej Kulach, and Zbigniew Gąsior. "Nuclear factor kappa-light-chain-enhancer of activated B cells (NF-κB): a new potential therapeutic target in atherosclerosis?." Pharmacological reports 62.5 (2010): 778-783.

Danial, N.N. and Korsmeyer, S.J., Cell death: critical control points. Cell, 2004.116(2): p. 205-219.

(56) References Cited

OTHER PUBLICATIONS

Davis CE, Arnold K (1974) Role of meningococcal endotoxin in meningococcal purpura. J Exp Med 140: 159-171.
Deng M, Scott MJ, Loughran P, Gibson G, Sodhi C, Watkins S, et al. (2013) Lipopolysaccharide clearance, bacterial clearance, and systemic inflammatory responses are regulated by cell type-specific functions of TLR4 during sepsis. J Immunol 190: 5152-5160.
Dey, A. and Cederbaum, A.I., Alcohol and oxidative liver injury. Hepatology, 2006. 43(2 Suppl 1): p. S63-74.
DiGiandomenico A, Veach RA, Zienkiewicz J, Moore DJ, Wylezinski LS, Hutchens MA, et al. (2014) The "genomic storm" induced by bacterial endotoxin is calmed by a nuclear transport modifier that attenuates localized and systemic inflammation. PLoS One 9: e110183.
Doerschug, K., Sanlioglu, S., Flaherty, D.M., Wilson, R.L., Yarovinsky, T., Monick, M.M., Engelhardt, J.F. and Hunninghake, G.W., First-generation adenovirus vectors shorten survival time in a murine model of sepsis. J. Immunol., 2002.169(11): p. 6539-6545.
Donald, R., Ballard, D.W. and Hawiger, J., Proteolytic processing of NF-kappa B/1 kappa B in human monocytes. ATP-dependent induction by pro-inflammatory mediators. J Biol Chem, 1995. 270(1): p. 9-12.
Duerschmied D, Bode C, Ahrens I (2014) Immune functions of platelets. Thromb Haemost 112: 678-691.
Fan, H. and Cook, J.A., Molecular mechanisms of endotoxin tolerance. J Endotoxin Res, 2004.10(2): p. 71-84.
Fischer, Rainer, et al. "Break on through to the Other Side—Biophysics and Cell Biology Shed Light on Cell-Penetrating Peptides." ChemBioChem 6.12 (2005): 2126-2142.
Frazier WJ, Wang X, Wancket LM, Li XA, Meng X, Nelin LD, et al. (2009) Increased inflammation, impaired bacterial clearance, and metabolic disruption after gram-negative sepsis in Mkp-1-deficient mice. J Immunol 183: 7411-7419.
Fujita T, Sugiyama Y, Taketomi S, Sohda T, Kawamatsu Y, Iwatsuka H, Suzuoki Z. Reduction of insulin resistance in obese and/or diabetic animals by 5-[4-(1-methylcyclohexylmethoxy) benzyl]-thiazolidine-2, 4-dione (ADD-3878, U-63,287, ciglitazone), a new antidiabetic agent. Diabetes. Sep. 1, 1983;32(9):804-10.
Geles, K.G., Johnson, J.J., Jong, S. and Adam, S.A., A role for Caenorhabditis elegans importin IMA-2 in germ line and embryonic mitosis. Mol Biol Cell, 2002.13(9): p. 3138-47.
Ghosh, S. and Karin, M., Missing pieces in the NF-kappaB puzzle. Cell, 2002.109 Suppl: p. S81-96.
Gilmore, T., Gapuzan, M.E., Kalaitzidis, D. and Starczynowski, D., Rel/NF-kappa B/1 kappa B signal transduction in the generation and treatment of human cancer. Cancer Lett, 2002.181(1): p. 1-9.
Gorlich, D., Henklein, P., Laskey, R.A. and Hartmann, E., A 41 amino acid motif in importin-alpha confers binding to importin-beta and hence transit into the nucleus. Embo J, 1996.15(8): p. 1810-7.
Greenblatt article, available online at http://drhellengreenblatt.info/archives/1688, 3 pages (2014).
Han, Chang Yeop, et al. "Reciprocal and coordinate regulation of serum amyloid A versus apolipoprotein AI and paraoxonase-1 by inflammation in murine hepatocytes." Arteriosclerosis, thrombosis, and vascular biology 26.8 (2006): 1806-1813.
Haraldsen G, Kvale D, Lien B, Farstad IN, Brandtzaeg P (1996) Cytokine-regulated expression of E-selectin, intercellular adhesion molecule-1 (ICAM-1), and vascular cell adhesion molecule-1 (VCAM-1) in human microvascular endothelial cells. J Immunol 156: 2558-2565.
Hawiger et al., "Cellular import of functional peptides to block intracellular signaling," Current Opinion in Immunology 9:189-196 (1997).
Hawiger J, Musser JM (2011) How to approach genome wars in sepsis? Crit Care 15: 1007.
Hawiger J, Veach, RA, Zienkiewicz J (2015). New Paradigms in Sepsis: From Prevention to Protection of Failing Microcirculation J. Thromb. Haemost. 13(10): 1743-56.
Hawiger J, Zienkiewicz J (2019) Decoding Inflammation, Its Causes, Genomic Responses, and Emerging Countermeasures. Scand. J. Immunol. e12812.
Hawiger, "Lipopolysaccharide-induced signal transduction and gene transcription." In Endotoxin and the Lungs, K. Brigham, ed., Marcel Dekker, Inc., New York, Basel, Hong Kong, pp. 69-82 (1994).
Hawiger, J. (1999) Noninvasive intracellular delivery of functional peptides and proteins. Curr. Opin. Chem. Biol., 3:89-94.
Hawiger, J. (2001) Innate immunity and inflammation: a transcriptional paradigm. Immunol. Res., 23(2-3):99-109.
Hawiger, J. (2002) Peptide/protein delivery in Encyclopedia of Molecular Medicine, John Wiley and Sons, 2435-2438.
Hering et al.: "Single-Donor, Marginal-Dose Islet Transplantation in Patients With Type 1 Diabetes", Journal of the American Medical Society, vol. 293, No. 7 (2005) pp. 830-835.
Herwig MC, Tsokos M, Hermanns MI, Kirkpatrick CJ, Müller AM (2013) Vascular Endothelial Cadherin Expression in Lung Specimens of Patients with Sepsis-Induced Acute Respiratory Distress Syndrome and Endothelial Cell Cultures. Pathobiology 80: 245-251.
Ho, Y.S., Gargano, M., Cao, J., Branson, R.T., Heimler, I. and Hutz, R.J., Reduced fertility in female mice lacking copper-zinc superoxide dismutase. J Biol Chem, 1998. 273(13): p. 7765-9.
Hong, F., Jaruga, B., Kim, W.H., Radaeva, S., El-Assal, O.N., Tian, Z., Nguyen, V.A. and Gao, B., Opposing roles of STAT1 and STAT5 in T cell-mediated hepatitis: regulation by SOCS. J Clin Invest, 2002.110(10): p. 1503-13.
Hughes BJ, Kennel S, Lee R, Huang L. Monoclonal antibody targeting of liposomes to mouse lung in vivo. Cancer research. Nov. 15, 1989;49(22):6214-20.
Hui P, Cook DJ, Lim W, Fraser GA, Arnold DM (2011) The frequency and clinical significance of thrombocytopenia complicating critical illness: a systematic review. Chest 139: 271-278.
Ihle, J.N., STATs: signal transducers and activators of transcription. Cell, 1996. 84(3): p. 331-4.
Im, S.H. and Rao, A., Activation and deactivation of gene expression by Ca2+/calcineurin-NFATmediated signaling. Mol Cells, 2004. 18(1): p. 1-9.
Jaeger, John A., Douglas H. Turner, and Michael Zuker. "[17] Predicting optimal and suboptimal secondary structure for RNA." (1990): 281-306.
Jaeger, John A., Douglas H. Turner, and Michael Zuker. "Improved predictions of secondary structures for RNA." Proceedings of the National Academy of Sciences 86.20 (1989): 7706-7710.
Jaeschke, H., Gujral, U.S. and Bajt, M.L., Apoptosis and necrosis in liver disease. Liver Int, 2004. 24(2): p. 85-9.
Jäggi, Rainer D., et al. "Modulation of nuclear pore topology by transport modifiers." Biophysical journal 84.1 (2003): 665-670.
Janssens, S. and Beyaert, R., Functional diversity and regulation of different interleukin-1 receptorassociated kinase (IRAK) family members. Mol Cell, 2003.11(2): p. 293-302.
Jaruga, B., Hong, F., Kim, W.H. and Gao, B., IFN-gamma/STAT1 acts as a proinflammatory signal in T cell-mediated hepatitis via induction of multiple chemokines and adhesion molecules: a critical role of IRF-1. Am J Physiol Gastrointest Liver Physiol, 2004. 287(5): p. G1044-52.
Jo, D., Liu, D., Yao, S., Collins, R.D. and Hawiger, J., Intracellular protein therapy with SOCS3 inhibits inflammation and apoptosis. Nat Med, 2005.11(8): p. 892-8.
Jo, D., Nashabi, A., Doxsee, C., Lin, Q., Unutmaz, D., Chen, J. and Ruley, H.E., Epigenetic regulation of gene structure and function with a cell-permeable Cre recombinase. Nat. Biotechnol., 2001. 19(10): p. 929-33.
Johnston, J.A. and O'Shea, J.J., Matching SOCS with function. Nat Immunol, 2003. 4(6): p. 507-9.
Jones, Jeremy C., et al. "Identification of the minimal active sequence of an anti-influenza virus peptide." Antimicrobial agents and chemotherapy 55.4 (2011): 1810-1813.
Jung TW, Hwang HJ, Hong HC, Choi HY, Yoo HJ, Baik SH, et al. (2014) Resolvin D1 reduces ER stress-induced apoptosis and triglyceride accumulation through JNK pathway in HepG2 cells. Mol Cell Endocrinol 391: 30-40.
Kaneto H, Nakatani Y, Miyatsuka T, Kawamori D, Matsuoka TA, Matsuhisa M, Kajimoto Y, Ichijo H, Yamasaki Y, Hori M. Possible novel therapy for diabetes with cell-permeable JNK-inhibitory peptide. Nature medicine. Oct. 2004;10(10):1128-32.

(56) References Cited

OTHER PUBLICATIONS

Kelley, Joshua B., et al. "Karyopherin α7 (KPNA7), a divergent member of the importin α family of nuclear import receptors." BMC cell biology 11.1 (2010): 1-12.
Keshavarzian, A. and Fields, J., Alcoholic liver disease: is it an "extraintestinal" complication of alcohol induced intestinal injury? J Lab Clin Med, 2003.142(5): p. 285-7.
Kessova, I.G., Ho, Y.S., Thung, S. and Cederbaum, A.I., Alcohol-induced liver injury in mice lacking Cu, Zn-superoxide dismutase. Hepatology, 2003. 38(5): p. 1136-45.
Kim, Sunshin, et al. "NF-κB prevents β cell death and autoimmune diabetes in NOD mice." Proceedings of the National Academy of Sciences 104.6 (2007): 1913-1918.
Kishimoto TK, Jutila MA, Berg EL, Butcher EC (1989) Neutrophil Mac-1 and MEL-14 adhesion proteins inversely regulated by chemotactic factors. Science 245: 1238-1241.
Kobayashi, K., Hernandez, L.D., Galan, J.E., Janeway, C.A., Jr., Medzhitov, R. and Flavell, R.A., IRAK M is a negative regulator of Toll-like receptor signaling. Cell, 2002.110(2): p. 191-202.
Kobe B., Autoinhibition by an internal nuclear localization signal revealed by the crystal structure of mammalian importin alpha. Nat Struct Biol. Apr. 1999;6(4):388-97.
Kohler, M., Speck, C., Christiansen, M., Bischoff, F.R., Prehn, S., Haller, H., Gorlich, D. and Hartmann, E., Evidence for distinct substrate specificities of importin alpha family members in nuclear protein import. Mol Cell Biol, 1999. 19(11): p. 7782-91.
Kosugi, Shunichi, et al. "Design of peptide inhibitors for the importin α/β nuclear import pathway by activity-based profiling." Chemistry & biology 15.9 (2008): 940-949.
Koteish, A., Yang, S., Lin, H., Huang, X. and Diehl, A.M., Chronic ethanol exposure potentiates lipopolysaccharide liver injury despite inhibiting Jun N-terminal kinase and caspase 3 activation. J Biol Chem, 2002. 277(15): p. 13037-44.
Koziel, M.J., Cytokines in viral hepatitis. Semin Liver Dis, 1999. 19(2): p. 157-69.
Krebs, D.L. and Hilton, D.J., SOCS proteins: negative regulators of cytokine signaling. Stem Cells, 2001. 19(5): p. 378-87.
Krebs, D.L. and Hilton, D.J., SOCS: physiological suppressors of cytokine signaling. J. Cell Sci., 2000. 113(Pt16): p. 2813-9.
Kroger C, Kary SC, Schauer K, Cameron AD (2016) Genetic Regulation of Virulence and Antibiotic Resistance in Acinetobacter baumannii. Genes (Basel) 8.
Kubo, M., Hanada, T. and Yoshimura, A., Suppressors of cytokine signaling and immunity. Nat Immunol, 2003. 4(12): p. 1169-76.
Kumar A, Roberts D, Wood KE, Light B, Parrillo JE, Sharma S, et al. (2006) Duration of hypotension before initiation of effective antimicrobial therapy is the critical determinant of survival in human septic shock. Crit Care Med 34: 1589-1596.
Kumar, The Evolution of Cancer, Angiogenesis, and Anti-Angiogenic Treatment, Current Science Review, Issue 1, 9 pages (Jan. 1, 2015).
Kusters, S., Gantner, F., Kunstle, G. and Tiegs, G., Interferon gamma plays a critical role in T celldependent liver injury in mice initiated by concanavalin A. Gastroenterology, 1996.111(2): p. 462-71.
Lai, W.S., Carballo, E., Thorn, J.M., Kennington, E.A. and Blackshear, P.J., Interactions of CCCH zinc finger proteins with mRNA. Binding of tristetraprolin-related zinc finger proteins to Au-rich elements and destabilization of mRNA. J Biol Chem, 2000. 275(23): p. 17827-37.
Lang, R., Pauleau, A.L., Parganas, E., Takahashi, Y., Mages, J., Ihle, J.N., Rutschman, R. and Murray, P.J., SOCS3 regulates the plasticity of gp130 signaling. Nat Immunol, 2003. 4(6): p. 546-50.
Langley RJ, Tsalik EL, van Velkinburgh JC, Glickman SW, Rice BJ, Wang C, et al. (2013) An integrated clinico-metabolomic model improves prediction of death in sepsis. Sci Transl Med 5: 195ra195. 28.

Leeuwenberg JF, Smeets EF, Neefjes JJ, Shaffer MA, Cinek T, Jeunhomme TM, et al. (1992) E-selectin and intercellular adhesion molecule-1 are released by activated human endothelial cells in vitro. Immunology 77: 543-549.
Lehmann, U., Schmitz, J., Weissenbach, M., Sobota, R.M., Hortner, M., Friederichs, K., Behrmann, I., Tsiaris, W., Sasaki, A., Schneider-Mergener, J., Yoshimura, A., Neel, B.G., Heinrich, P.C. and Schaper, F., SHP2 and SOCS3 contribute to Tyr-759-dependent attenuation of interleukin-6 signaling through gp130. J Biol Chem, 2003. 278(1): p. 661-71.
Levy, D.E. and Darnell, J.E., Jr., Stats: transcriptional control and biological impact. Nat Rev Mol Cell Biol, 2002. 3(9): p. 651-62.
Ley K (2003) The role of selectins in inflammation and disease. Trends Mol Med 9: 263-268.
Ley K, Bullard DC, Arbones ML, Bosse R, Vestweber D, Tedder TF, et al. (1995) Sequential contribution of L- and P-selectin to leukocyte rolling in vivo. J Exp Med 181: 669-675.
Li, C., Zienkiewicz, J., Hawiger, J. Interactive sites in the MyD88 Toll/interleukin (IL) 1 receptor domain responsible for coupling to the IL1β signaling pathway. J Biol Chem. 2005, 280:26152-9.
Li, P., Nijhawan, D., Budihardjo, I., Srinivasula, S.M., Ahmad, M., Alnemri, E.S. and Wang, X., Cytochrome c and dATP-dependent formation of Apaf-1/caspase-9 complex initiates an apoptotic protease cascade. Cell, 1997. 91(4): p. 479-89.
Liberati, NT., Fitzgerald, K.A., Kim, D.H., Feinbaum, R., Golenbock, D.T. and Ausubel, F.M., Requirement for a conserved Toll/interleukin-1 resistance domain protein in the Caenorhabditis elegans immune response. Proc Natl Acad Sci USA, 2004.101(17): p. 6593-8.
Lin, H.Z., Yang, S.Q., Chuckaree, C., Kuhajda, F., Ronnet, G. and Diehl, A.M., Metformin reverses fatty liver disease in obese, leptin-deficient mice. Nat Med, 2000. 6(9): p. 998-1003.
Lin, Yao-Zhong, et al. "Inhibition of nuclear translocation of transcription factor NF-κB by a synthetic peptide containing a cell membrane-permeable motif and nuclear localization sequence." Journal of Biological Chemistry 270.24 (1995): 14255-14258.
Link, A.J., Eng, J., Schieltz, D.M., Carmack, E., Mize, G.J., Morris, D.R., Garvik, B.M. and Yates, I., J. R., Direct Analysis of protein complexes using mass spectrometry. Nature Biotechnology, 1999. 17: p. 676-682.
Litzinger and Huang, Biochimica et Biophysica Acta, 1104:179-187, (1992).
Liu D, Zienkiewicz J, DiGiandomenico A, Hawiger J. Suppression of Acute Lung Inflammation by intracellular peptide delivery of a nuclear transport inhibitor. Mol. Ther. 2009, 17(5):796-802.
Liu G, Ye X, Miller EJ, Liu SF (2014) NF-kappaB-to-AP-1 switch: a mechanism regulating transition from endothelial barrier injury to repair in endotoxemic mice. Sci Rep 4: 5543.
Liu Y, Major AS, Zienkiewicz J, Gabriel CL, Veach RA, Moore DJ, et al. (2013) Nuclear transport modulation reduces hypercholesterolemia, atherosclerosis, and fatty liver. J Am Heart Assoc 2: e000093.
Liu Y, Veach RA, Zienkiewicz J, Boyd KL, Smith TE, Xu XQ, Wylezinski L. and Hawiger J. Protection from Endotoxin Shock by Selective Targeting of Proinflammatory Signaling to the Nucleus Mediated by Importin Alpha 5. ImmunoHorizons 2019; 3 (9),440-446.
Liu, D., Li, C., Chen, Y., Burnett, C., Liu, X.Y., Downs, S., Collins, R.D. and Hawiger, J., Nuclear import of proinflammatory transcription factors is required for massive liver apoptosis induced by bacterial lipopolysaccharide. J. Biol. Chem., 2004. 279(46): p. 48434-42.
Liu, D., Liu, X.Y., Robinson, D., Burnett, C., Jackson, C., Seele, L., Veach, R.A., Downs, S., Collins, R.D., Ballard, D.W., and Hawiger, J. (2004) Suppression of *staphylococcal* enterotoxin B-induced toxicity by a nuclear import inhibitor. J. Biol. Chem., 279: 19239-46.
Liu, et al. "Identification of a functionally important sequence in the cytoplasmic tail of integrin beta 3 by using cell-permeable peptide analogs," Proceedings of the National Academy of Sciences, National Academy of Sciences, vol. 93, 1996, 11819-11824.

(56) References Cited

OTHER PUBLICATIONS

Liu, X.Y., Robinson, D., Veach, R.A., Liu, D., Timmons, S., Collins, R.D. and Hawiger, J., Peptide directed suppression of a pro-inflammatory cytokine response. J Biol Chem, 2000, 275(22): p. 16774-8.
Lott K, Cingolani G., The importin β binding domain as a master regulator of nucleocytoplasmic transport. Biochim Biophys Acta. Sep. 2011;1813(9):1578-92. doi: 10.1016/j.bbamcr.2010.10.012. Epub Oct. 26, 2010.
Lush CW, Cepinskas G, Sibbald WJ, Kvietys PR (2001) Endothelial E- and P-selectin expression in iNOS-deficient mice exposed to polymicrobial sepsis. Am J Physiol Gastrointest Liver Physiol 280: G291-297.
Madge, L.A. and Pober, J.S., TNF signaling in vascular endothelial cells. Exp Mol Pathol, 2001. 70(3): p. 317-25.
Mann RE, Smart RG, and Govoni R (2003) The Epidemiology of Alcoholic Liver Disease Alcohol Research& Health.
Mansell, A., Smith, R., Doyle, S.L., Gray, P., Fenner, J.E., Crack, P.J., Nicholson, S.E., Hilton, D.J., O'Neill, L.A. and Hertzog, P.J., Suppressor of cytokine signaling 1 negatively regulates Toll-like receptor signaling by mediating Mal degradation. Nat Immunol, 2006. 7(2): p. 148-55.
Marine, J.C., McKay, C., Wang, D., Topham, D.J., Parganas, E., Nakajima, H., Pendeville, H., Yasukawa, H., Sasaki, A., Yoshimura, A. and Ihle, J.N., SOCS3 is essential in the regulation of fetal liver erythropoiesis. Cell, 1999. 98(5): p. 617-27.
Martin, G.S., Mannino, D.M., Eaton, S. and Moss, M., The epidemiology of sepsis in the United States from 1979 through 2000. N Engl J Med, 2003. 348(16): p. 1546-54.
Matsui, H., Hikichi, Y., Tsuji, I., Yamada, T. and Shintani, Y., LIGHT, a member of the tumor necrosis factor ligand superfamily, prevents tumor necrosis factor-alpha-mediated human primary hepatocyte apoptosis, but not Fas-mediated apoptosis. J Biol Chem, 2002. 277(51): p. 50054-61.
McClain, C.J., Song, Z., Barve, S.S., Hill, D.B. and Deaciuc, I., Recent advances in alcoholic liver disease. IV. Dysregulated cytokine metabolism in alcoholic liver disease. Am J Physiol Gastrointest Liver Physiol, 2004. 287(3): p. G497-502.
McGettrick, A.F. and O'Neill, L.A., The expanding family of MyD88-like adaptors in Toll-like receptor signal transduction. Mol Immunol, 2004. 41(6-7): p. 577-82.
McMullen, M.R., Cocuzzi, E., Hatzoglou, M. and Nagy, I.E., Chronic ethanol exposure increases the binding of HuR to the TNFalpha 5'-untranslated region in macrophages. J Biol Chem, 2003. 278(40): p. 38333-41.
Medzhitov, R. and Janeway, C., Jr., Innate immunity. N Engl J Med, 2000. 343(5) p. 338-44.
Meier et al.: "Sustained Beta Cell Apoptosis in Patients With Long-Standing Type 1 Diabetes: Indirect Evidence for Islet Regeneration", Diabetologia, vol. 48 (2005) pp. 2221-2228.
Melen, K., Fagerlund, R., Franke, J., Kohler, M., Kinnunen, L. and Julkunen, I., Importin alpha nuclear localization signal binding sites for STAT1, STAT2, and influenza A virus nucleoprotein. J Biol Chem, 2003. 278(30): p. 28193-200.
Mink, M., Fogelgren, B., Olszewski, K., Maroy, P. and Csiszar, K., A novel human gene (SARM) at chromosome 17q11 encodes a protein with a SAM motif and structural similarity to Armadillo/betacatenin that is conserved in mouse, *Drosophila*, and Caenorhabditis elegans. Genomics, 2001. 74(2): p. 234-44.
Moore JD, Yang J, Truant R, Kornbluth S., Nuclear import of Cdk/cyclin complexes: identification of distinct mechanisms for import of Cdk2/cyclin E and Cdc2/cyclin B1, J Cell Biol. Jan. 25, 1999;144(2):213-24.
Moore, Daniel J., et al. "In vivo islet protection by a nuclear import inhibitor in a mouse model of type 1 diabetes." PLoS One 5.10 (2010): e13235.
Nagy, I.E., Molecular Aspects of Alcohol Metabolism: Transcription Factors Involved in Early Ethanol-Induced Liver Injury. Annu Rev Nutr, 2004. 24: p. 55-78.
Nagy, L.E., Recent insights into the role of the innate immune system in the development of alcoholic liver disease. Exp Biol Med (Maywood), 2003. 228(8): p. 882-90.
Naka, T., Matsumoto, T., Narazaki, M., Fujimoto, M., Morita, Y., Ohsawa, Y., Saito, H., Nagasawa, T., Uchiyama, Y. and Kishimoto, T., Accelerated apoptosis of lymphocytes by augmented induction of Bax in SSI-1 (STAT-induced STAT inhibitor-1) deficient mice. ProcNatlAcadSciUSA, 1998. 95(26): p. 15577-82.
Naka, T., Tsutsui, H., Fujimoto, M., Kawazoe, Y., Kohzaki, H., Morita, Y., Nakagawa, R., Narazaki, M., Adachi, K., Yoshimoto, T., Nakanishi, K. and Kishimoto, T., SOCS-1/SSI-1-deficient NKT cells participate in severe hepatitis through dysregulated cross-talk inhibition of IFN-gamma and IL-4 signaling in vivo. Immunity, 2001.14(5): p. 535-45.
Naveau, S., Chollet-Martin, S., Dharancy, S., Mathurin, P., Jouet, P., Piquet, M.A., Davion, T., Oberti, F., Broet, P. and Emilie, D., A double-blind randomized controlled trial of infliximab associated with prednisolone in acute alcoholic hepatitis. Hepatology, 2004. 39(5): p. 1390-7.
Needleman SB, Wunsch CD. A general method applicable to the search for similarities in the amino acid sequence of two proteins. Journal of molecular biology. Mar. 28, 1970;48(3):443-53.
Nordqvist, "Everything you need to know about inflammation", available online at https://www.medicalnewstoday.com/articles/248423.php, 12 pages (last updated Nov. 2017) (Year: 2017).
O'Neill, L.A., Fitzgerald, K.A. and Bowie, A.G., The Toll-IL-1 receptor adaptor family grows to five members. Trends Immunol, 2003. 24(6): p. 286-90.
Opal SM (2010) New perspectives on immunomodulatory therapy for bacteraemia and sepsis. Int J Antimicrob Agents 36 Suppl 2: S70-73.
Orange, J. S. et al.: "Cell penetrating peptide inhibitors of Nuclear Factor-kappa B", Cell. Mo!. Life Sci. 65, p. 3564-3591, 2008.
Pahl, H.L., Activators and target genes of Rel/NF-kappaB transcription factors. Oncogene, 1999. 18(49): p. 6853-6866.
Pearson WR, Lipman DJ. Improved tools for biological sequence comparison. Proceedings of the National Academy of Sciences. Apr. 1, 1988;85(8):2444-8.
Pfeffer, K., Matsuyama, T., Kundig, T.M., Wakeham, A., Kishihara, K., Shahinian, A., Wiegmann, K., Ohashi, P.S., Kronke, M. and Mak, T.W., Mice deficient for the 55 kd tumor necrosis factor receptor are resistant to endotoxic shock, yet succumb to L. monocytogenes infection. Cell, 1993. 73(3): p. 457-467.
Pieper et al.: "Activation of Nuclear Factor-[kappa]B in Cultured Endothelial Cells by Increased Glucose Concentration: Prevention by Calphostin C", Journal of Cardiovascular Pharmacology vol. 30(4): p. 528-532, 1997. https://pubmed.ncbi.nlm.nih.gov/9335415/.
Pietersz GA, McKenzie IF. Antibody conjugates for the treatment of cancer. Immunological reviews. Oct. 1992;129(1):57-80.
Qiu G, Wang C, Smith R, Harrison K, Yin K (2001) Role of IFN-gamma in bacterial containment in a model of intra-abdominal sepsis. Shock 16: 425-429.
Raper, S.E., Yudkoff, M., Chirmule, N., Gao, G.P., Nunes, F., Haskal, Z.J., Furth, E.E., Propert, K.J., Robinson, M.B., Magosin, S., Simoes, H., Speicher, L., Hughes, J., Tazelaar, J., Wivel, N.A., Wilson, J.M. and Batshaw, M.L., A pilot study of in vivo liver-directed gene transfer with an adenoviral vector in partial ornithine transcarbamylase deficiency. Hum. Gene Ther., 2002.13(1): p. 163-175.
Reddy RC, Chen GH, Newstead MW, Moore T, Zeng X, Tateda K, et al. (2001) Alveolar macrophage deactivation in murine septic peritonitis: role of interleukin 10. Infect Immun 69: 1394-1401.
Rizo et al., Annu. Rev. Biochem. 61:387-418 (1992).
Roberts, A.W., Robb, L, Rakar, S., Hartley, L, Cluse, L, Nicola, N.A., Metcalf, D., Hilton, D.J. and Alexander, W.S., Placental defects and embryonic lethality in mice Tlacking suppressor of cytokine signaling 3. Proc NatlAcad Sci USA, 2001. 98(16): p. 9324-9.
Roffler SR, Wang SM, Chern JW, Yeh MY, Tung E. Anti-neoplastic glucuronide prodrug treatment of human tumor cells targeted with a monoclonal antibody-enzyme conjugate. Biochemical pharmacology. Oct. 24, 1991;42(10):2062-5.

(56) References Cited

OTHER PUBLICATIONS

Rosati, O. and Martin, M.U., Identification and characterization of murine IRAK-M. Biochem Biophys Res Commun, 2002. 293(5): p. 1472-7.
Rothe, J., Lesslauer, W., Lotscher, H., Lang, Y., Koebel, P., Kontgen, F., Althage, A., Zinkernagel, R., Steinmetz, M. and Bluethmann, H., Mice lacking the tumour necrosis factor receptor 1 are resistant to TNF-mediated toxicity but highly susceptible to infection by Listeria monocytogenes. Nature, 1993. 364(6440): p. 798-802.
Sakiyama, Haruhiko, et al. "Regulation of Nuclear Import/Export of Carbohydrate Response Element-binding Protein (ChREBP) Interaction of An A-Helix Of Chrebp With The 14-3-3 Proteins And Regulation by Phosphorylation." Journal of Biological Chemistry 283.36 (2008): 24899-24908.
Schooley, K., Zhu, P., Dower, S.K. and Qwarnstrom, E.E., Regulation of nuclear translocation of nuclear factor-kappaB relA: evidence for complex dynamics at the single-cell level. Biochem J, 2003. 369(Pt2): p. 331-9.
Schroeder M, Brooks BD, Brooks AE (2017) The Complex Relationship between Virulence and Antibiotic Resistance. Genes (Basel) 8.
Schwarze, S.R. and Dowdy, S.F., In vivo protein transduction: intracellular delivery of biologically active proteins, compounds and DNA. Trends Pharmacol Sci, 2000. 21(2): p. 45-8.
Seino, K., Kayagaki, N., Takeda, K., Fukao, K., Okumura, K. and Yagita, H., Contribution of Fas ligand to T cell-mediated hepatic injury in mice. Gastroenterology, 1997. 113(4): p. 1315-22.
Senter PD, Su PC, Katsuragi T, Sakai T, Cosand WL, Hellstrom I, Hellstrom KE. Generation of 5-fluorouracil from 5-fluorocytosine by monoclonal antibody-cytosine deaminase conjugates. Bioconjugate chemistry. Nov. 1, 1991;2(6):447-51.
Senter PD, Wallace PM, Svensson HP, Vrudhula VM, Kerr DE, Hellstroem I, Hellstroem KE. Generation of cytotoxic agents by targeted enzymes. Bioconjugate chemistry. Jan. 1, 1993;4(1):3-9.
Shayakhmetov, D.M., Li, Z.Y., Ni, S. and Lieber, A., Analysis of adenovirus sequestration in the liver, transduction of hepatic cells, and innate toxicity after injection of fiber-modified vectors. J. Virol., 2004. 78(10): p. 5368-5381.
Shimano, Hitoshi. "Sterol regulatory element-binding proteins (SREBPs) transcriptional regulators of lipid synthetic genes." Progress in lipid research 40.6 (2001): 439-452.
Siegmund, S.V. and Brenner, D.A., Molecular pathogenesis of alcohol-induced hepatic fibrosis. Alcohol Clin Exp Res, 2005. 29(11 Suppl): p. 102S-109S.
Silverman, N. and Maniatis, T., NF-kappaB signaling pathways in mammalian and insect innate immunity. Genes Dev, 2001.15(18): p. 2321-42.
Simpson et al., BMC Neurology 14:15 (2014).
Smith et al., Nursing, pp. 37-42 (2014).
Smith TF, Waterman MS. Comparison of biosequences. Advances in applied mathematics. Dec. 1, 1981;2(4):482-9.
Soltani N, Qiu H, Aleksic M, Glinka Y, Zhao F, Liu R, Li Y, Zhang N, Chakrabarti R, Ng T, Jin T. GABA exerts protective and regenerative effects on islet beta cells and reverses diabetes. Proceedings of the National Academy of Sciences. Jul. 12, 2011;108(28):11692-7.
Song, E., Lee, S.K., Wang, J., Ince, N., Ouyang, N., Min, J., Chen, J., Shankar, P. and Lieberman, J., RNA interference targeting Fas protects mice from fulminant hepatitis. Nat Med, 2003. 9(3): p. 347-51.
Starr, R., Metcalf, D., Elefanty, A.G., Brysha, M., Willson, T.A., Nicola, N.A., Hilton, D.J. and Alexander, W.S., Liver degeneration and lymphoid deficiencies in mice lacking suppressor of cytokine signaling-1. Proc NatlAcad Sci USA, 1998. 95(24): p. 14395-9.
Steeber DA, Tang ML, Green NE, Zhang XQ, Sloane JE, Tedder TF (1999) Leukocyte entry into sites of inflammation requires overlapping interactions between the L-selectin and ICAM-1 pathways. J Immunol 163: 2176-2186.
Stevenson RW, Hutson NJ, Krupp MN, Volkmann RA, Holland GF, Eggler JF, Clark DA, McPherson RK, Hall KL, Danbury BH, Gibbs EM. Actions of novel antidiabetic agent englitazone in hyperglycemic hyperinsulinemic ob/ob mice. Diabetes. Oct. 1, 1990;39(10):1218-27.
Stoiber, D., Kovarik, P., Cohney, S., Johnston, J.A., Steinlein, P. and Decker, T., Lipopolysaccharide induces in macrophages the synthesis of the suppressor of cytokine signaling 3 and suppresses signal transduction in response to the activating factor IFN-gamma. J. Immunol., 1999.163(5): p. 2640-7.
Sun, Wei, et al. "Intramuscular transfer of naked calcitonin gene-related peptide gene prevents autoimmune diabetes induced by multiple low-dose streptozotocin in C57BL mice." European journal of immunology 33.1 (2003): 233-242.
Takahashi, Y., Carpino, N., Cross, J.C., Torres, M., Parganas, E. and Ihle, J.N., SOCS3: an essential regulator of LIF receptor signaling in trophoblast giant cell differentiation. Embo J, 2003. 22(3): p. 372-84.
Talcott B, Moore MS (1999) Getting across the nuclear pore complex. Trends Cell Biol 9: 312-318.
Thornberry, N.A. and Lazebnik, Y., Caspases: enemies within. Science, 1998. 281(5381): p. 1312-6.
Tiegs, G., Hentschel, J. and Wendel, A., A T cell-dependent experimental liver injury in mice inducible by concanavalin A. J Clin Invest, 1992. 90(1): p. 196-203.
Tilg, H. and Diehl, A.M., Cytokines in alcoholic and nonalcoholic steatohepatitis. N Engl J Med, 2000. 343(20): p. 1467-76.
Todd JF, Bloom SR. Incretins and other peptides in the treatment of diabetes. Diabetic medicine. Mar. 2007;24(3):223-32.
Torgerson TR, Colosia AD, Donahue JP, Lin YZ, Hawiger J (1998) Regulation of NF-kappa B, AP-1, NFAT, and STAT1 nuclear import in T lymphocytes by noninvasive delivery of peptide carrying the nuclear localization sequence of NF-kappa B p50. J Immunol 161: 6084-6092.
Torgerson, T.R., Colosia, A.D., Donahue, J.P., Lin, Y.Z. and Hawiger, J., Regulation of NF-kappa B, AP-1, NFAT, and STAT1 nuclear import in T lymphocytes by noninvasive delivery of peptide carrying the nuclear localization sequence of NF-kappa B p50. J Immunol, 1998. 161(11): p. 6084-92.
Trautwein, C., Rakemann, T., Malek, N.P., Plumpe, J., Tiegs, G. and Manns, M.P., Concanavalin A induced liver injury triggers hepatocyte proliferation. J Clin Invest, 1998.101(9): p. 1960-9.
Tuschl, H. and Schwab, C.E., Flow cytometric methods used as screening tests for basal toxicity of chemicals. Toxicol In Vitro, 2004. 18(4): p. 483-91.
Uesugi, T., Froh, M., Arteel, G.E., Bradford, B.U. and Thurman, R.G., Toll-like receptor 4 is involved in the mechanism of early alcohol-induced liver injury in mice. Hepatology, 2001. 34(1): p. 101-8.
Veach RA, Liu D, Yao S, Chen Y, Liu XY, Downs S, et al. (2004) Receptor/transporter-independent targeting of functional peptides across the plasma membrane. J Biol Chem 279: 11425-11431.
Veach RA, Zienkiewicz J, Collins RD, Hawiger J (2012) Lethality in a murine model of pulmonary anthrax is reduced by combining nuclear transport modifier with antimicrobial therapy. PLoS One 7: e30527.
Veach, R.A., Liu, D., Yao, S., Chen, Y., Liu, X.Y., Downs, S. and Hawiger, J., Receptor/transporter independent targeting of functional peptides across the plasma membrane. J. Biol. Chem., 2004. 279(12): p. 11425-31.
Venkatesh, N., Feng, Y., DeDecker, B., Yacono, P., Golan, D., Mitchison, T. and McKeon, F., Chemical genetics to identify NFAT inhibitors: potential of targeting calcium mobilization in immunosuppression. ProcNatlAcadSciUSA, 2004.101(24): p. 8969-74.
Vincent JL, Rello J, Marshall J, Silva E, Anzueto A, Martin CD, et al. (2009) International study of the prevalence and outcomes of infection in intensive care units. JAMA 302: 2323-2329.
Wajchenberg, B. L. "Beta-Cell Failure in Diabetes and Preservation by Clinical Treatment", Endocrine Reviews, vol. 28, No. 2 (2007) pp. 187-218.
Wallington J, Ning J, Titheradge MA (2008) The control of hepatic glycogen metabolism in an in vitro model of sepsis. Mol Cell Biochem 308: 183-192.
Weis K (2003) Regulating access to the genome. Nucleocytoplasmic transport throughout the cell cycle. Cell 112: 441-451.

(56) References Cited

OTHER PUBLICATIONS

Weis, K., Regulating access to the genome: nucleocytoplasmic transport throughout the cell cycle. Cell, 2003. 112(4): p. 441-451.
Wolff SM (1973) Biological effects of bacterial endotoxins in man. J Infect Dis 128: Suppl:259-264.
Wolter, K.G., Hsu, Y.T., Smith, C.L., Nechushtan, A., Xi, X.G. and Youle, R.J., Movement of Bax from the cytosol to mitochondria during apoptosis. J Cell Biol, 1997.139(5): p. 1281-92.
Wynn JL, Scumpia PO, Delano MJ, O'Malley KA, Ungaro R, Abouhamze A, et al. (2007) Increased mortality and altered immunity in neonatal sepsis produced by generalized peritonitis. Shock 28: 675-683.
Wynn JL, Wilson CS, Hawiger J, Scumpia PO, Marshall AF, Liu JH, et al. (2016) Targeting IL-17A attenuates neonatal sepsis mortality induced by IL-18. Proc Natl Acad Sci U S A 113: E2627-2635.
Xiao W, Mindrinos MN, Seok J, Cuschieri J, Cuenca AG, Gao H, et al. (2011) A genomic storm in critically injured humans. J Exp Med 208: 2581-2590.
Xue, Hui, et al. "The inhibitory effect of polypeptide cSN50 on alcoholic hepatic injuries through blocking the binding of NF-κB to importin α." Scandinavian journal of gastroenterology 46.7-8 (2011): 931-940.
Yang Z, Chen M, Carter JD, Nunemaker CS, Garmey JC, Kimble SD, Nadler JL. Combined treatment with lisofylline and exendin-4 reverses autoimmune diabetes. Biochemical and biophysical research communications. Jun. 9, 2006;344(3):1017-22.
Yasukawa, H., Ohishi, M., Mori, H., Murakami, M., Chinen, T., Aki, D., Hanada, T., Takeda, K., Akira, S., Hoshijima, M., Hirano, T., Chien, K.R. and Yoshimura, A., IL-6 induces an anti-inflammatory response in the absence of SOCS3 in macrophages. Nat Immunol, 2003. 4(6): p. 551-6.
Ye X, Ding J, Zhou X, Chen G, Liu SF (2008) Divergent roles of endothelial NF-kappaB in multiple organ injury and bacterial clearance in mouse models of sepsis. J Exp Med 205: 1303-1315.
Yoshimura, A., Mori, H., Ohishi, M., Aki, D. and Hanada, T., Negative regulation of cytokine signaling influences inflammation. CurrOpin Immunol, 2003.15(6): p. 704-8.
Zhang et al. "Preparation of functionally active cell-permeable peptides by single-step ligation of two peptide modules" PNAS Aug. 4, 1998 vol. 95 No. 16 9184-9189.
Zhang, J.G., Metcalf, D., Rakar, S., Asimakis, M., Greenhalgh, C.J., Willson, T.A., Starr, R., Nicholson, S.E., Carter, W., Alexander, W.S., Hilton, D.J. and Nicola, N.A., The SOCS box of suppressor of cytokine signaling-1 is important for inhibition of cytokine action in vivo. Proc. Natl. Acad. Sci. U. S. A., 2001.98(23): p. 13261-5.
Zienkiewicz J, Armitage A, Hawiger J (2013) Targeting nuclear import shuttles, importins/karyopherins alpha by a peptide mimicking the NFkappaB1/p50 nuclear localization sequence. J Am Heart Assoc 2: e000386.
Zima, T. and Kalousova, M., Oxidative stress and signal transduction pathways in alcoholic liver disease. Alcohol Clin Exp Res, 2005. 29(11 Suppl): p. 110S-115S.
Zonneveld R, Martinelli R, Shapiro NI, Kuijpers TW, Plotz FB, Carman CV (2014) Soluble adhesion molecules as markers for sepsis and the potential pathophysiological discrepancy in neonates, children and adults. Crit Care 18: 204.
Zuker M. On finding all suboptimal foldings of an RNA molecule. Science. Apr. 7, 1989;244(4900):48-52.

\* cited by examiner

```
                       SEQUENCE LISTING

<160> NUMBER OF SEQ ID NOS: 41

<210> SEQ ID NO 1
<211> LENGTH: 29
<212> TYPE: PRT
<213> ORGANISM: Artificial Sequence
<220> FEATURE:
<223> OTHER INFORMATION: Synthetic construct

<400> SEQUENCE: 1

Ala Ala Val Ala Leu Leu Pro Ala Val Leu Leu Ala Leu Leu Ala Pro
1               5                   10                  15

Cys Tyr Val Gln Arg Lys Arg Gln Lys Leu Met Pro Cys
            20                  25

<210> SEQ ID NO 2
<211> LENGTH: 28
<212> TYPE: PRT
<213> ORGANISM: Artificial Sequence
<220> FEATURE:
<223> OTHER INFORMATION: Synthetic construct

<400> SEQUENCE: 2

Ala Ala Val Ala Leu Leu Pro Ala Val Leu Leu Ala Leu Leu Ala Pro
1               5                   10                  15

Cys Val Gln Arg Lys Arg Gln Lys Leu Met Pro Cys
            20                  25

<210> SEQ ID NO 3
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (17)..(19)
<223> OTHER INFORMATION: Xaa can be any naturally occurring amino acid
<220> FEATURE:
```

```
<221> NAME/KEY: misc_feature
<222> LOCATION: (26)..(29)
<223> OTHER INFORMATION: Xaa can be any naturally occurring amino acid

<400> SEQUENCE: 3

Xaa Xaa Xaa Xaa Leu Leu Pro Xaa Xaa Leu Leu Ala Leu Leu Ala Pro
1               5                   10                  15

Xaa Xaa Xaa Gln Arg Lys Arg Gln Lys Xaa Xaa Xaa Xaa
            20                  25

<210> SEQ ID NO 4
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (17)..(19)
<223> OTHER INFORMATION: Xaa can be any naturally occurring amino acid
<220> FEATURE:
<221> NAME/KEY: misc_feature
<222> LOCATION: (26)..(29)
<223> OTHER INFORMATION: Xaa can be any naturally occurring amino acid

<400> SEQUENCE: 4

Xaa Xaa Xaa Xaa Leu Leu Pro Xaa Xaa Leu Leu Ala Leu Leu Ala Pro
1               5                   10                  15

Cys Xaa Xaa Gln Arg Lys Arg Gln Lys Xaa Xaa Xaa Cys
            20                  25

<210> SEQ ID NO 5
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (18)..(19)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (26)..(27)
<223> OTHER INFORMATION: Xaa can be any naturally occurring amino acid

<400> SEQUENCE: 5

Xaa Xaa Xaa Xaa Leu Leu Pro Xaa Xaa Leu Leu Ala Leu Leu Ala Pro
1               5                   10                  15

Cys Xaa Gln Arg Lys Arg Gln Lys Xaa Xaa Xaa Cys
            20                  25
```

```
<210> SEQ ID NO 6
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (17)..(19)
<223> OTHER INFORMATION: Xaa can be any naturally occurring amino acid
<220> FEATURE:
<221> NAME/KEY: misc_feature
<222> LOCATION: (26)..(29)
<223> OTHER INFORMATION: Xaa can be any naturally occurring amino acid

<400> SEQUENCE: 6

Xaa Xaa Xaa Xaa Leu Leu Pro Xaa Xaa Leu Leu Ala Val Leu Ala Pro
1               5                   10                  15

Xaa Xaa Xaa Gln Arg Lys Arg Gln Lys Xaa Xaa Xaa Xaa
            20                  25

<210> SEQ ID NO 7
<211> LENGTH: 28
<212> TYPE: PRT
<213> ORGANISM: Artificial Sequence
<220> FEATURE:
<223> OTHER INFORMATION: Synthetic construct

<400> SEQUENCE: 7

Ala Ala Val Ala Leu Leu Pro Ala Val Leu Leu Ala Val Leu Ala Pro
1               5                   10                  15

Cys Val Gln Arg Lys Arg Gln Lys Leu Met Pro Cys
            20                  25

<210> SEQ ID NO 8
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (17)..(19)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (26)..(29)
<223> OTHER INFORMATION: Xaa can be any naturally occurring amino acid

<400> SEQUENCE: 8
```

```
Xaa Xaa Xaa Xaa Leu Leu Pro Xaa Xaa Leu Leu Ala Leu Leu Ala Pro
1               5                   10                  15

Xaa Xaa Gln Arg Asp Glu Gln Lys Xaa Xaa Xaa Xaa
            20                  25
```

<210> SEQ ID NO 9
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (25)..(27)
<223> OTHER INFORMATION: Xaa can be any naturally occurring amino acid

<400> SEQUENCE: 9

```
Xaa Xaa Xaa Xaa Leu Leu Pro Xaa Xaa Leu Leu Ala Leu Leu Ala Pro
1               5                   10                  15

Cys Xaa Gln Arg Asp Glu Gln Lys Xaa Xaa Xaa Cys
            20                  25
```

<210> SEQ ID NO 10
<211> LENGTH: 10
<212> TYPE: PRT
<213> ORGANISM: Artificial Sequence
<220> FEATURE:
<223> OTHER INFORMATION: Synthetic construct

<400> SEQUENCE: 10

```
Val Gln Arg Lys Arg Gln Lys Leu Met Pro
1               5                   10
```

<210> SEQ ID NO 11
<211> LENGTH: 10
<212> TYPE: PRT
<213> ORGANISM: Artificial Sequence
<220> FEATURE:
<223> OTHER INFORMATION: Synthetic construct

<400> SEQUENCE: 11

```
Val Gln Arg Asp Glu Gln Lys Leu Met Pro
1               5                   10
```

<210> SEQ ID NO 12
<211> LENGTH: 12
<212> TYPE: PRT
<213> ORGANISM: Artificial Sequence
<220> FEATURE:
<223> OTHER INFORMATION: Synthetic construct

<400> SEQUENCE: 12

```
Cys Val Gln Arg Lys Arg Gln Lys Leu Met Pro Cys
1               5                   10
```

<210> SEQ ID NO 13

```
<211> LENGTH: 26
<212> TYPE: PRT
<213> ORGANISM: Artificial Sequence
<220> FEATURE:
<223> OTHER INFORMATION: Synthetic construct

<400> SEQUENCE: 13

Ala Ala Val Ala Leu Leu Pro Ala Val Leu Ala Leu Leu Ala Pro
1               5                   10                  15

Val Gln Arg Lys Arg Gln Lys Leu Met Pro
            20                  25

<210> SEQ ID NO 14
<211> LENGTH: 7
<212> TYPE: PRT
<213> ORGANISM: Artificial Sequence
<220> FEATURE:
<223> OTHER INFORMATION: Synthetic construct

<400> SEQUENCE: 14

Ala Ala Val Ala Leu Leu Pro
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic construct

<400> SEQUENCE: 15

Ala Val Leu Leu Ala Leu Leu Ala Pro
1               5

<210> SEQ ID NO 16
<211> LENGTH: 28
<212> TYPE: PRT
<213> ORGANISM: Artificial Sequence
<220> FEATURE:
<223> OTHER INFORMATION: Synthetic construct

<400> SEQUENCE: 16

Ala Ala Val Ala Leu Leu Pro Ala Val Leu Ala Leu Leu Ala Pro
1               5                   10                  15

Cys Val Gln Arg Asp Glu Gln Lys Leu Met Pro Cys
            20                  25

<210> SEQ ID NO 17
<211> LENGTH: 16
<212> TYPE: PRT
<213> ORGANISM: Artificial Sequence
<220> FEATURE:
<223> OTHER INFORMATION: Synthetic construct

<400> SEQUENCE: 17

Ala Ala Val Ala Leu Leu Pro Ala Val Leu Ala Leu Leu Ala Pro
1               5                   10                  15

<210> SEQ ID NO 18
<211> LENGTH: 32
<212> TYPE: PRT
<213> ORGANISM: Artificial Sequence
<220> FEATURE:
<223> OTHER INFORMATION: Synthetic construct

<400> SEQUENCE: 18
```

Ala Ala Val Ala Leu Leu Pro Ala Val Leu Leu Ala Leu Leu Ala Pro
1               5                   10                  15

Arg Arg Arg Arg Ile Glu Val Asn Val Glu Leu Arg Lys Ala Lys Lys
                20                  25                  30

<210> SEQ ID NO 19
<211> LENGTH: 34
<212> TYPE: PRT
<213> ORGANISM: Artificial Sequence
<220> FEATURE:
<223> OTHER INFORMATION: Synthetic construct

<400> SEQUENCE: 19

Ala Ala Val Ala Leu Leu Pro Ala Val Leu Leu Ala Leu Leu Ala Pro
1               5                   10                  15

Arg Arg Arg Arg Ile Glu Val Asn Val Glu Leu Arg Lys Ala Lys Lys
                20                  25                  30

Asp Asp

<210> SEQ ID NO 20
<211> LENGTH: 34
<212> TYPE: PRT
<213> ORGANISM: Artificial Sequence
<220> FEATURE:
<223> OTHER INFORMATION: Synthetic construct

<400> SEQUENCE: 20

Ala Ala Val Ala Leu Leu Pro Ala Val Leu Leu Ala Leu Leu Ala Pro
1               5                   10                  15

Arg Arg Gln Arg Asn Glu Val Val Val Glu Leu Arg Lys Asn Lys Arg
                20                  25                  30

Asp Glu

<210> SEQ ID NO 21
<211> LENGTH: 34
<212> TYPE: PRT
<213> ORGANISM: Artificial Sequence
<220> FEATURE:
<223> OTHER INFORMATION: Synthethic constrcut

<400> SEQUENCE: 21

Ala Ala Val Ala Leu Leu Pro Ala Val Leu Leu Ala Leu Leu Ala Pro
1               5                   10                  15

Arg Arg His Arg Asn Glu Val Thr Val Glu Leu Arg Lys Asn Lys Arg
                20                  25                  30

Asp Glu

<210> SEQ ID NO 22
<211> LENGTH: 34
<212> TYPE: PRT
<213> ORGANISM: Artificial Sequence
<220> FEATURE:
<223> OTHER INFORMATION: Synthetic construct

<400> SEQUENCE: 22

Ala Ala Val Ala Leu Leu Pro Ala Val Leu Leu Ala Leu Leu Ala Pro
1               5                   10                  15

Arg Arg Arg Arg Glu Glu Glu Gly Leu Gln Leu Arg Lys Gln Lys Arg
                20                  25                  30

Glu Glu

```
<210> SEQ ID NO 23
<211> LENGTH: 34
<212> TYPE: PRT
<213> ORGANISM: Artificial Sequence
<220> FEATURE:
<223> OTHER INFORMATION: Synthetic construct

<400> SEQUENCE: 23

Ala Ala Val Ala Leu Leu Pro Ala Val Leu Leu Ala Leu Leu Ala Pro
1               5                   10                  15

Arg Arg Arg Arg Glu Glu Glu Gly Ile Gln Leu Arg Lys Gln Lys Arg
            20                  25                  30

Glu Gln

<210> SEQ ID NO 24
<211> LENGTH: 28
<212> TYPE: PRT
<213> ORGANISM: Artificial Sequence
<220> FEATURE:
<223> OTHER INFORMATION: Synthetic construct

<400> SEQUENCE: 24

Ala Ala Val Ala Leu Leu Pro Ala Val Leu Leu Ala Leu Leu Ala Pro
1               5                   10                  15

Cys Thr Glu Met Arg Arg Arg Arg Ile Glu Val Cys
            20                  25

<210> SEQ ID NO 25
<211> LENGTH: 37
<212> TYPE: PRT
<213> ORGANISM: Artificial Sequence
<220> FEATURE:
<223> OTHER INFORMATION: Synthetic construct

<400> SEQUENCE: 25

Ala Ala Val Ala Leu Leu Pro Ala Val Leu Leu Ala Leu Leu Ala Pro
1               5                   10                  15

Val Glu Leu Arg Lys Ala Lys Lys Asp Asp Gln Met Leu Lys Arg Arg
            20                  25                  30

Asn Val Ser Ser Phe
        35

<210> SEQ ID NO 26
<211> LENGTH: 37
<212> TYPE: PRT
<213> ORGANISM: Artificial Sequence
<220> FEATURE:
<223> OTHER INFORMATION: Synthetic construct

<400> SEQUENCE: 26

Ala Ala Val Ala Leu Leu Pro Ala Val Leu Leu Ala Leu Leu Ala Pro
1               5                   10                  15

Val Glu Leu Arg Lys Asn Lys Arg Asp Glu His Leu Leu Lys Arg Arg
            20                  25                  30

Asn Val Pro His Glu
        35

<210> SEQ ID NO 27
<211> LENGTH: 37
<212> TYPE: PRT
<213> ORGANISM: Artificial Sequence
<220> FEATURE:
<223> OTHER INFORMATION: Synthetic construct
```

```
<400> SEQUENCE: 27

Ala Ala Val Ala Leu Leu Pro Ala Val Leu Leu Ala Leu Leu Ala Pro
1               5                   10                  15

Val Glu Leu Arg Lys Asn Lys Arg Asp Glu His Leu Leu Lys Lys Arg
            20                  25                  30

Asn Val Pro Gln Glu
        35

<210> SEQ ID NO 28
<211> LENGTH: 37
<212> TYPE: PRT
<213> ORGANISM: Artificial Sequence
<220> FEATURE:
<223> OTHER INFORMATION: Synthetic construct

<400> SEQUENCE: 28

Ala Ala Val Ala Leu Leu Pro Ala Val Leu Leu Ala Leu Leu Ala Pro
1               5                   10                  15

Leu Gln Leu Arg Lys Gln Lys Arg Glu Glu Gln Leu Phe Lys Arg Arg
            20                  25                  30

Asn Val Ala Thr Ala
        35

<210> SEQ ID NO 29
<211> LENGTH: 37
<212> TYPE: PRT
<213> ORGANISM: Artificial Sequence
<220> FEATURE:
<223> OTHER INFORMATION: Synthetic construct

<400> SEQUENCE: 29

Ala Ala Val Ala Leu Leu Pro Ala Val Leu Leu Ala Leu Leu Ala Pro
1               5                   10                  15

Ile Gln Leu Arg Lys Gln Lys Arg Glu Gln Gln Leu Phe Lys Arg Arg
            20                  25                  30

Asn Val Glu Leu Ile
        35

<210> SEQ ID NO 30
<211> LENGTH: 29
<212> TYPE: PRT
<213> ORGANISM: Artificial Sequence
<220> FEATURE:
<223> OTHER INFORMATION: Synthetic construct

<400> SEQUENCE: 30

Ala Ala Val Ala Leu Leu Pro Ala Val Leu Leu Ala Leu Leu Ala Pro
1               5                   10                  15

Cys Val Glu Leu Arg Lys Ala Lys Lys Asp Asp Gln Cys
            20                  25

<210> SEQ ID NO 31
<211> LENGTH: 29
<212> TYPE: PRT
<213> ORGANISM: Artificial Sequence
<220> FEATURE:
<223> OTHER INFORMATION: Synthetic construct

<400> SEQUENCE: 31

Ala Ala Val Ala Leu Leu Pro Ala Val Leu Leu Ala Leu Leu Ala Pro
1               5                   10                  15

Cys Val Glu Leu Arg Lys Asn Lys Arg Asp Glu His Cys
```

20                  25

<210> SEQ ID NO 32
<211> LENGTH: 29
<212> TYPE: PRT
<213> ORGANISM: Artificial Sequence
<220> FEATURE:
<223> OTHER INFORMATION: Synthetic construct

<400> SEQUENCE: 32

Ala Ala Val Ala Leu Leu Pro Ala Val Leu Leu Ala Leu Leu Ala Pro
1               5                   10                  15

Cys Leu Gln Leu Arg Lys Gln Lys Arg Glu Glu Gln Cys
            20                  25

<210> SEQ ID NO 33
<211> LENGTH: 29
<212> TYPE: PRT
<213> ORGANISM: Artificial Sequence
<220> FEATURE:
<223> OTHER INFORMATION: Synthetic construct

<400> SEQUENCE: 33

Ala Ala Val Ala Leu Leu Pro Ala Val Leu Leu Ala Leu Leu Ala Pro
1               5                   10                  15

Cys Ile Gln Leu Arg Lys Gln Lys Arg Glu Gln Gln Cys
            20                  25

<210> SEQ ID NO 34
<211> LENGTH: 29
<212> TYPE: PRT
<213> ORGANISM: Artificial Sequence
<220> FEATURE:
<223> OTHER INFORMATION: Synthetic construct

<400> SEQUENCE: 34

Ala Ala Val Ala Leu Leu Pro Ala Val Leu Leu Ala Leu Leu Ala Pro
1               5                   10                  15

Cys Gln Met Leu Lys Arg Arg Asn Val Ser Ser Phe Cys
            20                  25

<210> SEQ ID NO 35
<211> LENGTH: 29
<212> TYPE: PRT
<213> ORGANISM: Artificial Sequence
<220> FEATURE:
<223> OTHER INFORMATION: Synthetic construct

<400> SEQUENCE: 35

Ala Ala Val Ala Leu Leu Pro Ala Val Leu Leu Ala Leu Leu Ala Pro
1               5                   10                  15

Cys His Leu Leu Lys Arg Arg Asn Val Pro His Glu Cys
            20                  25

<210> SEQ ID NO 36
<211> LENGTH: 29
<212> TYPE: PRT
<213> ORGANISM: Artificial Sequence
<220> FEATURE:
<223> OTHER INFORMATION: Synthetic construct

<400> SEQUENCE: 36

Ala Ala Val Ala Leu Leu Pro Ala Val Leu Leu Ala Leu Leu Ala Pro
1               5                   10                  15

```
Cys His Leu Leu Lys Lys Arg Asn Val Pro Gln Glu Cys
            20                  25

<210> SEQ ID NO 37
<211> LENGTH: 29
<212> TYPE: PRT
<213> ORGANISM: Artificial Sequence
<220> FEATURE:
<223> OTHER INFORMATION: Synthetic construct

<400> SEQUENCE: 37

Ala Ala Val Ala Leu Leu Pro Ala Val Leu Leu Ala Leu Leu Ala Pro
1               5                   10                  15

Cys Gln Leu Phe Lys Arg Arg Asn Val Ala Thr Ala Cys
            20                  25

<210> SEQ ID NO 38
<211> LENGTH: 29
<212> TYPE: PRT
<213> ORGANISM: Artificial Sequence
<220> FEATURE:
<223> OTHER INFORMATION: Synthetic construct

<400> SEQUENCE: 38

Ala Ala Val Ala Leu Leu Pro Ala Val Leu Leu Ala Leu Leu Ala Pro
1               5                   10                  15

Cys Gln Leu Phe Lys Arg Arg Asn Val Glu Leu Ile Cys
            20                  25

<210> SEQ ID NO 39
<211> LENGTH: 37
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: Xaa can be any naturally occurring amino acid

<400> SEQUENCE: 39

Ala Ala Val Ala Leu Leu Pro Ala Val Xaa Leu Ala Xaa Xaa Ala Pro
1               5                   10                  15

Val Glu Leu Arg Lys Asn Lys Arg Asp Glu His Leu Leu Lys Arg Arg
            20                  25                  30

Asn Val Pro His Glu
        35

<210> SEQ ID NO 40
<211> LENGTH: 28
<212> TYPE: PRT
<213> ORGANISM: Artificial Sequence
<220> FEATURE:
<223> OTHER INFORMATION: Synthetic construct

<400> SEQUENCE: 40

Ala Ala Val Ala Leu Leu Pro Ala Val Leu Leu Ala Leu Leu Ala Pro
1               5                   10                  15

Cys Val Gln Arg Asp Glu Gln Lys Leu Met Pro Cys
            20                  25
```

```
<210> SEQ ID NO 41
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: Xaa can be any naturally occurring amino acid

<400> SEQUENCE: 41

Ala Ala Val Ala Leu Leu Pro Ala Val Xaa Leu Ala Xaa Xaa Ala Pro
1               5                   10                  15

Cys Val Gln Arg Lys Arg Gln Lys Leu Met Pro Cys
            20                  25
```

METHODS AND COMPOSITIONS FOR TREATING ALCOHOLIC LIVER DISEASE

This Application is a continuation-in-part of International PCT Application No. PCT/US19/51005, filed on Sep. 13, 2019, which claims the benefit of U.S. Provisional Application No. 62/733,997, filed on Sep. 20, 2018 and U.S. Provisional Application No. 62/731,394, filed on Sep. 14, 2018; a continuation-in-part of U.S. application Ser. No. 16/622,469, filed Dec. 13, 2019, which is a national stage application filed under 35 U.S.C. § 371 of PCT/US2018/037993, filed Jun. 18, 2018, which claims the benefit of U.S. Provisional Patent Application No. 62/521,159, filed on Jun. 16, 2017; and a continuation-in-part of U.S. application Ser. No. 16/799,350, filed on Feb. 24, 2020, which is a divisional of and claims priority to U.S. application Ser. No. 15/297,996, filed on Oct. 19, 2016, now U.S. Pat. No. 10,568,928, which is a divisional of U.S. application Ser. No. 14/251,135, filed on Apr. 11, 2014, now U.S. Pat. No. 9,492,544, which claims the benefit of U.S. provisional application No. 61/810,939, filed Apr. 11, 2013, applications which are incorporated herein by reference in their entirety.

I. BACKGROUND

Alcoholic liver disease (ALD) afflicts an estimated 2 million patients in the US with an astounding 65% mortality rate over a 4-year period. Acute or chronic alcohol abuse alters homeostatic balance that exists between intracellular mediators and suppressors of proinflammatory signaling. This signaling culminates in genomic reprogramming of the liver cells manifested by expression of proinflammatory and proapoptotic mediators. ALD represents an example of metabolic inflammation caused by excessive and chronic use of ethanol-containing beverages.

Inflammation represents a fundamental mechanism of diseases caused by microbial, autoimmune, autoinflammatory, metabolic, and physical insults. Millions of people in the United States and globally suffer from inflammatory diseases. Inflammation is the body's response to harmful stimuli, and when limited, is beneficial and helps the body heal. However, when inflammation is unchecked it can lead to tissue destruction, necrosis, and fibrosis. For example, the action of microbial insults on microvascular endothelial cells in severe microbial infections evolving into their end stage, septic shock, leads to endothelial dysfunction that contributes to major organ failure, disseminated intravascular coagulation (DIC) involving liver microcirculation, acute respiratory distress syndrome (ARDS), acute kidney injury, and acute brain injury. Similarly, autoimmune factors targeting the body's own cells and organs develop into rampant inflammation, destroying skin and joints in psoriasis, lupus, and rheumatoid arthritis, and insulin-producing beta cells in Type 1 diabetes. Microbial and metabolic inflammation leads to insulin resistance, which underlies Type 2 diabetes. Chronic microbial inflammation caused by the oral microbiota of periodontitis, and bronchitis contribute to coronary heart disease while Hepatitis C virus infecting 200 million people worldwide contributes to fatty liver (steatosis), cirrhosis and, ultimately liver cancer.

Unfortunately, many inflammatory diseases are not adequately treated using conventional therapeutics. Steroidal anti-inflammatory drugs (e.g., hydrocortisone, prednisone, and methylprednisolone) have significant side effects increasing blood glucose, blood lipids and body fat distribution, skin thinning and delayed wound healing, muscle weakness, osteoporosis, increased susceptibility to infections, cataract, increased in eye pressure, stomach ulcers, and psychiatric disturbances. Methotrexate therapy is associated gastrointestinal and liver toxicity. Non-steroidal anti-inflammatory drugs (e.g., aspirin, ibuprofen, naproxen, celebrex) may cause fluid retention leading to edema, kidney failure (primarily with chronic use), liver failure, ulcers and prolonged bleeding after an injury or surgery. Inhibitors of kinases that target Bruton Tyrosine kinase (ibrutinib, acalabrutinib) and the JAK family of kinases may cause serious opportunistic infections with *Mycobacterium tuberculosis*, *Herpes zoster*, *Cytomegalovirus*, and *Pneumocystis jirovecii* pneumonia. Finally, monoclonal antibodies such as anti-TNFα monoclonal antibody carry the risk of the reactivation of latent infection with *Mycobacterium tuberculosis* and the monoclonal antibody natalizumab carries the risk of JC virus-caused progressive multifocal leukoencephalopathy in patients with multiple sclerosis. Thus, there is a need for more effective therapeutics for preventing and treating inflammation-mediated diseases.

II. SUMMARY

Disclosed are methods and compositions related to treating an inflammatory disorder.

In one aspect, disclosed herein are methods of treating/inhibiting/reducing an alcoholic liver disease in a subject comprising administering to the subject a therapeutically effective amount of a composition comprising one or more Nuclear Transport Modifier (NTM) such as, for example, an NTM that comprises the sequence set forth in SEQ ID NO: 1, SEQ ID NO: 2, SEQ ID NO: 3; SEQ ID NO: 4; SEQ ID NO: 5; SEQ ID NO: 6, SEQ ID NO: 7, SEQ ID NO: 8, SEQ ID NO: 9, SEQ ID NO: 11, SEQ ID NO: 13, SEQ ID NO: 16, SEQ ID NO: 17, SEQ ID NO: 18, SEQ ID NO: 19; SEQ ID NO: 20; SEQ ID NO: 21; SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29; SEQ ID NO: 30; SEQ ID NO: 31; SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39; SEQ ID NO: 40; and/or SEQ ID NO: 41.

III. BRIEF DESCRIPTION OF THE DRAWINGS

The accompanying drawings, which are incorporated in and constitute a part of this specification, illustrate several embodiments and together with the description illustrate the disclosed compositions and methods.

FIG. 1 displays proinflammatory signaling to the nucleus mediated by Stress-Responsive Transcription Factors (SRTFs).

Figure 4:
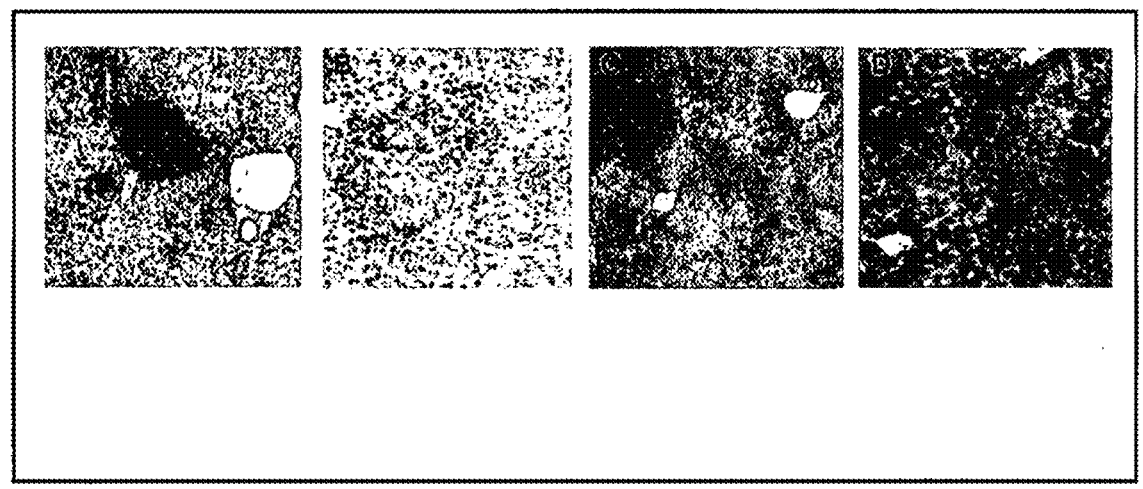

FIG. 4 shows liver sections from pair-fed control mouse that received a low dose of ConA. Single focus of necrosis is present. (Panel A, lower power; Panel B high power). Liver section from EtOH-fed mouse that received a low dose of Con A. Many foci of necrosis are present. Hematoxylin and eosin stain. (Panel C, low power; Panel D, high power).

Figure 5:
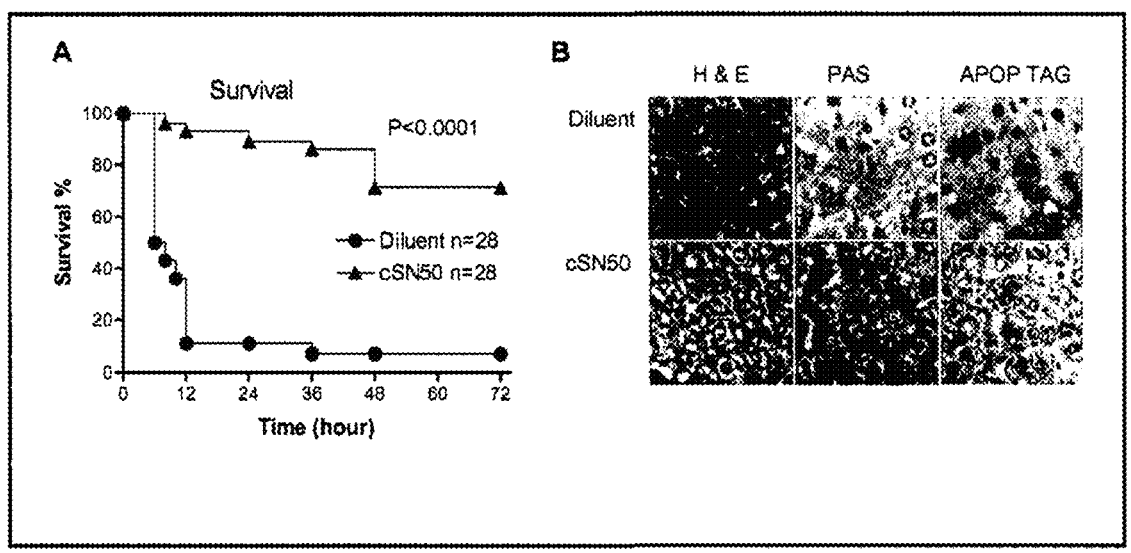

FIG. 5 shows LPS-Induced Liver injury: survival and liver apoptosis accompanied by hemorrhagic necrosis in control mice as compared to the cSN50 peptide-treated mice.

Figure 6:
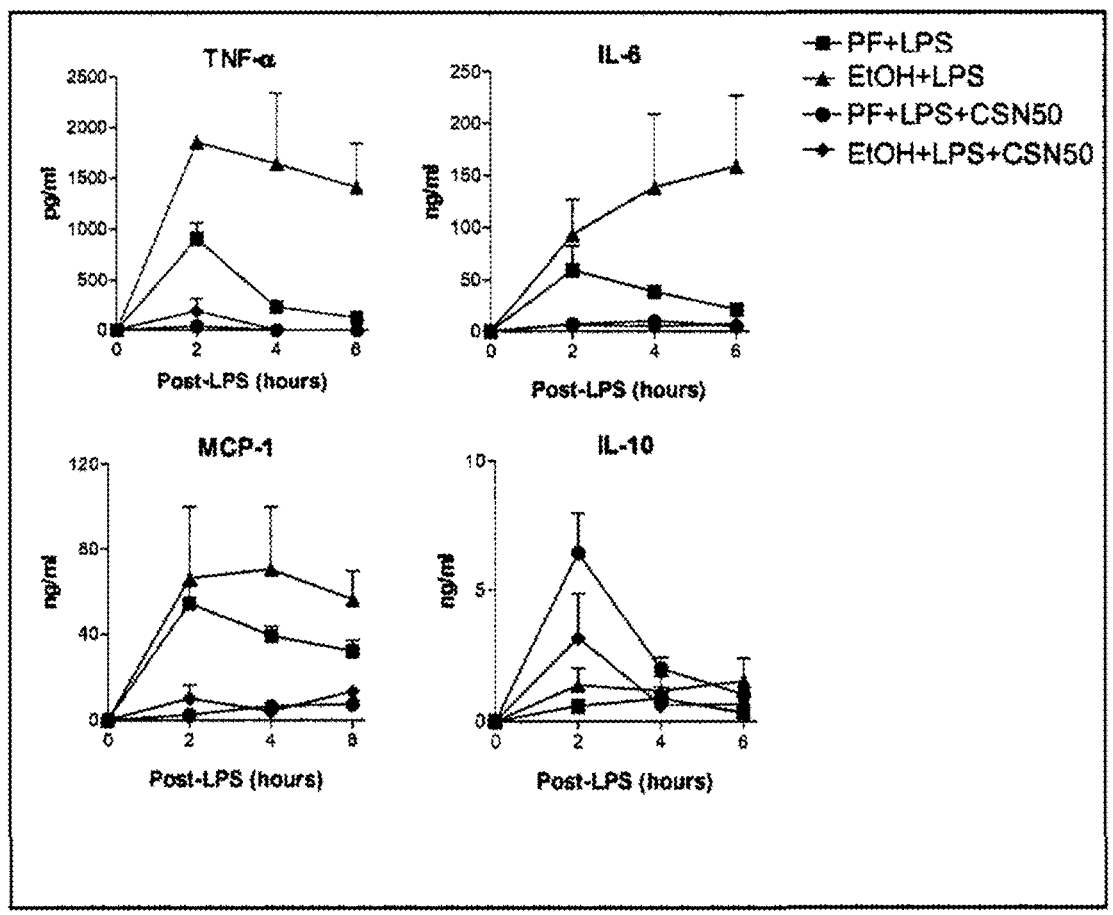

FIG. 6 shows ethanol (EtOH)-enhanced liver injury caused by LPS is suppressed by nuclear import inhibitor (cSN50peptide). PF=pair-fed control.

Figure 7:
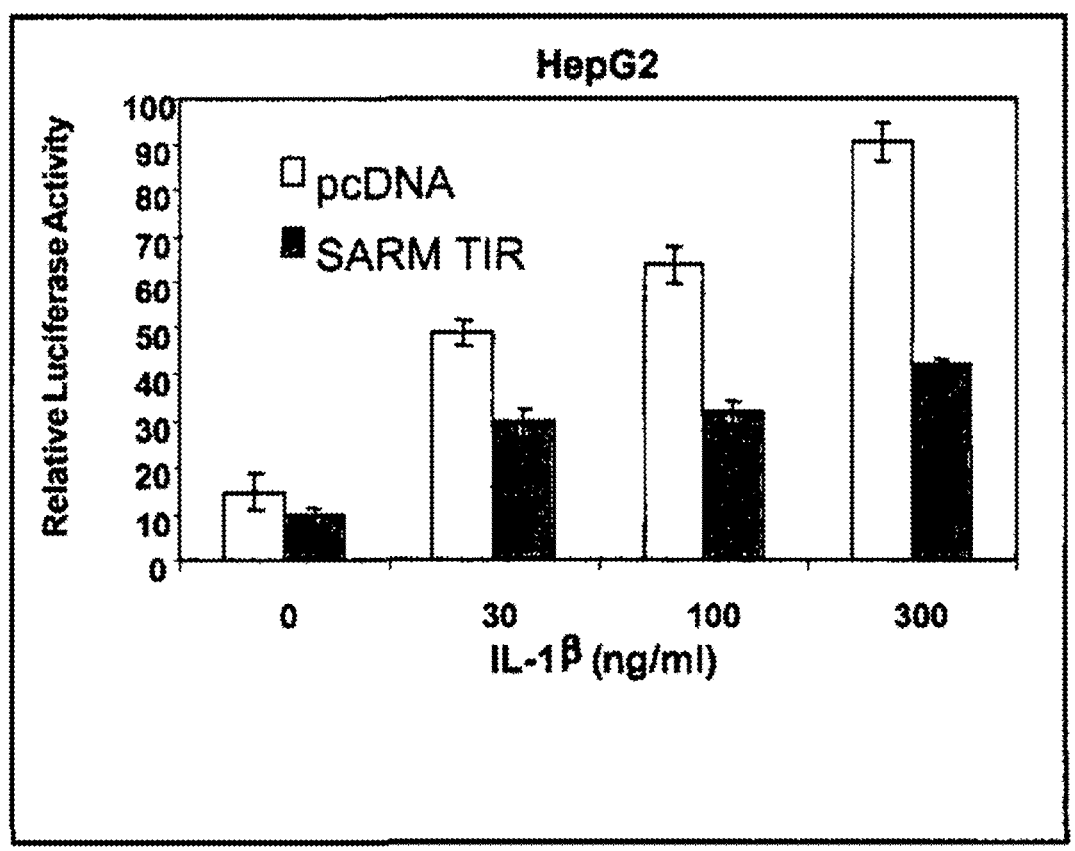

FIG. 7 shows that forced expression of SARM TIR domain inhibits IL-beta-induced NK-κB reporter gene activity in HepG2 cells.

IV. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. DEFINITIONS

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims, which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

The terms "patient," "subject" and "individual" are used interchangeably herein, and mean an animal (e.g., mammalian (such as human, equine, bovine, ovine, porcine, canine, etc.), reptilian, piscine, etc.) to be treated, diagnosed and/or to obtain a biological sample from.

As used herein, "bind," "binds," or "interacts with" means that one molecule recognizes and attaches/adheres to a particular second molecule in a sample or organism but does not substantially recognize or attaches/adhere to other structurally unrelated molecules in the sample. Generally, a first molecule that "specifically binds" a second molecule has a binding affinity greater than about $10^8$ to $10^{12}$ moles/liter for that second molecule and involves precise "hand-in-a-glove" docking interactions that can be covalent and non-covalent (hydrogen bonding, hydrophobic, ionic, and van der Waals).

By the phrase "nuclear transport modifier" and "NTM" is meant a cell-penetrating peptide that is capable of modulating entry of transcription factors into the nucleus. An example of a nuclear transport modifier is a 26-29 amino acid peptide derived from human nuclear factor kappa B1 nuclear localization sequence and from human Fibroblast Growth Factor 4 signal sequence hydrophobic region. This phrase is used interchangeably with the phrase "nuclear import inhibitor."

In an NTM as described herein, any of the amino acid residues in the NTM sequence can be mutated and/or modified, i.e. to form mimetics or stapled peptides to stabilize their conformation (Moiola M et al 2019) so long as the modifications do not affect the cell membrane translocating function of the peptide. Thus, the word "peptide" includes mimetics and the word "amino acid" includes modified amino acids, unusual amino acids, D-form amino acids, etc.

By the phrases "importin alpha-selective Nuclear Transport Modifier (NTM)" also known as "Importin alpha inhibitor" and "importin alpha-selective NTM" also known as importin alpha-selective inhibitor" is meant any NTM that binds to major and/or minor binding pockets of one or more of importins alpha that recognize their own autoinhibitory regions or other proteins that bear a nuclear localization sequence (NLS) and are larger than approximately 45 kD (e.g., proinflammatory Stress-Responsive Transcription Factors and metabolic transcription factors) and that modulate nuclear transport of at least one intracellular protein, e.g., an intracellular protein that regulates cell responses to proinflammatory and metabolic stimuli. Typically, the importin alpha 5-selective NTM is the sequence of or a sequence derived from AAVALL-PAVXLAXXAPCVQRKRQKLMPC (SEQ ID NO: 41), where X represents any amino acid from the group of hydrophobic or special amino acids (e.g., cysteine, glycine, and proline, non-natural amino acids) (e.g., cSN50.1 peptide).

By the phrases "importin beta-selective Nuclear Transport Modifier (NTM)" also known as "Importin beta inhibitor" and "importin beta-selective NTM" also known as importin beta-selective inhibitor" is meant any NTM that binds to importin beta 1 and modifies its nuclear transport function while sparing a similar function of importins alpha and that modulates nuclear transport of at least one intracellular protein, e.g., an intracellular protein that regulates cell responses to metabolic and proinflammatory stimuli. Typically, the importin beta-selective NTM includes a peptide sequence that includes an SSHR domain derived from Signal Sequence Hydrophobic Region of Fibroblast Growth Factor 4 and a hydrophilic segment to counterbalance hydrophobic properties of SSHR.

As used herein, the phrases "nuclear import adaptor" and "nuclear transport adaptor", or "nuclear transport shuttle" mean a cell component capable of mediating transport of a protein usually larger than 45 kD (e.g., a transcription factor) or a complex of two proteins (e.g. a dimer comprising transcription factors cFos and cJun) into the nucleus. An example of a nuclear transport adaptor is an importin also known as karyopherin.

As used herein, "protein" and "polypeptide" are used synonymously to mean any peptide-linked chain of amino acids, regardless of length or post-translational modification, e.g., glycosylation or phosphorylation.

By the term "gene" is meant a nucleic acid molecule that codes for a particular protein, or in certain cases, a functional or structural RNA molecule.

As used herein, a "nucleic acid" or a "nucleic acid molecule" means a chain of two or more nucleotides such as RNA (ribonucleic acid) and DNA (deoxyribonucleic acid).

The term "labeled," with regard to a nucleic acid, protein, probe or antibody, is intended to encompass direct labeling of the nucleic acid, protein, probe or antibody by coupling (i.e., physically or chemically linking) a detectable substance (detectable agent) to the nucleic acid, protein, probe or antibody.

As used herein, the terms "therapeutic," and "therapeutic agent" are used interchangeably, and are meant to encompass any molecule, chemical entity, composition, drug, cell(s), therapeutic agent, chemotherapeutic agent, or biological agent capable of preventing, ameliorating, or treating a disease or other medical condition. The term includes small molecule compounds, antisense reagents, siRNA reagents, antibodies, enzymes, peptides organic or inorganic molecules, cells, natural or synthetic compounds and the like.

As used herein, the term "treatment" is defined as the application or administration of a therapeutic agent to a patient or subject, or application or administration of the therapeutic agent to an isolated tissue or cell line from a patient or subject, who has a disease, a symptom of disease or a predisposition toward a disease, with the purpose to cure, heal, alleviate, relieve, alter, remedy, ameliorate, improve or affect the disease, the symptoms of disease, or the predisposition toward disease.

A "decrease" can refer to any change that results in a smaller amount of a symptom, disease, composition, condition, or activity. A substance is also understood to decrease the genetic output of a gene when the genetic output of the gene product with the substance is less relative to the output of the gene product without the substance. Also, for example, a decrease can be a change in the symptoms of a disorder such that the symptoms are less than previously observed. A decrease can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% decrease so long as the decrease is statistically significant.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

An "increase" can refer to any change that results in a greater amount of a symptom, disease, composition, condition or activity. An increase can be any individual, median, or average increase in a condition, symptom, activity, composition in a statistically significant amount. Thus, the increase can be a 1, 2, 3, 4, 5, 6, 7, 8, 9, 10, 15, 20, 25, 30, 35, 40, 45, 50, 55, 60, 65, 70, 75, 80, 85, 90, 95, or 100% increase so long as the increase is statistically significant. Increases can also be referenced in terms of fold increases. For example, an increase can comprise a 2, 3, 4, 5, 6, 7, 8, 9, 10, 15, 20, 30, 40, 50, 60, 70, 80, 90, 100, 200, 300, 400, 500, 600, 700, 800, 900, $10^3$, $10^4$, $10^5$, $10^6$, $10^7$, $10^8$, $10^9$, $10^{10}$-fold increase.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular nuclear transport modifier (NTM) is disclosed and discussed and a number of modifications that can be made to a number of molecules including the NTM are discussed, specifically contemplated is each and every combination and permutation of NTM and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

B. METHODS OF USE

Although compositions, kits, cells, and methods similar or equivalent to those described herein can be used in the practice or testing of the present invention, suitable compositions, kits, cells, and methods are described below. All publications, patent applications, and patents mentioned herein are incorporated by reference in their entirety. U.S. patent application Ser. No. 14/349,918, and U.S. Pat. No. 7,553,929, for example, are incorporated by reference in their entireties. In the case of conflict, the present specification, including definitions, will control. The particular embodiments discussed below are illustrative only and not intended to be limiting.

Small transcription factors (<40 kD), usually those regulating the housekeeping genes that encode cell survival factors, have free passage from the cytoplasm to the nucleus. In contrast, once activated, nuclear transport of transcription factors larger than 40 kD, such as Stress-Responsive Transcription Factors (SRTFs) in monomeric or dimeric form, are translocated to the nucleus by a family of adaptors termed importins/karyopherins. This nuclear import machinery recognizes nuclear localization sequence (NLS) exposed on SRTFs. NLSs are then recognized by nuclear transport adaptor proteins, importins/karyopherins alpha (Imp α) (see FIG. 1). The stimulus-induced formation of SRTF and importins α complexes also encompasses importin beta 1 (Imp β1), which is recognized by nuclear pore proteins to allow translocation of the cargo to the nucleus. Once access to the nucleus is permitted, SRTFs activate a myriad of genes that encode cytokines, chemokines, cell adhesion molecules, signal transducers, and other mediators of inflammation and apoptosis. In turn these mediators evoke leukocyte migration, cell adhesion, and tissue injury. Metabolic transcription factors, such as SREBP1 and SREBP2 are solely transported to the nucleus by importin β1 that recognizes highly conserved basic-helix-loop-helix that forms a dimer and binds to this nuclear transport shuttle (see FIG. 2).

Until recently, nuclear transport has been targeted through the forced expression of genes that encode inhibitors of proinflammatory SRTFs, such as the degradation-resistant inhibitor of NF-κB termed IκBα. However, NF-κB is only one of multiple SRTFs that mediate signaling to the nucleus in response to infection. Other SRTFs, such as AP-1, STAT1 and NFAT, are also transported to the nucleus during the inflammatory response yet their nuclear transport is not impeded by IκBα; contrarily, the AP-1 pathway is enhanced (Hawiger and Zienkiewicz 2019 Scand. J. Immunol). Targeting nuclear transport, a pivotal checkpoint integrating translocation of multiple transcription factors to the nucleus, can be a more efficient strategy than targeting signaling pathways of individual transcription factors. This concept was proven by design and development of Nuclear Transport Modifiers (NTMs).

These advances open up the ability to apply cell penetrating peptides as innovative tools for treatment of inflammatory liver injury caused by ethanol (EtOH). EtOH-enhanced production of proinflammatory cytokines and chemokines with attendant liver apoptosis/necrosis caused by concanavalin A, a T cell polyclonal mitogen, can be suppressed by a new class of cell-penetrating peptides and proteins. Results from these studies establish proof-of-concept for intracellular peptide/protein therapy of ethanol-induced liver injury.

NTMs target the nuclear transport shuttles, Imp α5 and Imp β1, that translocate SRTFs to the nucleus and control signal transduction pathways, which culminate in genomic reprogramming NTMs target nuclear transport adaptors. NTMs modulate signaling to the nucleus mediated by transcription factors that include but are not limited to NF-κB, AP-1, NFAT, STAT1, NRF2, and Carbohydrate Responsive Element-Binding Proteins (ChREBPs) that utilize importins alpha and beta heterodimer, SREBP1a, SREBP1c, and SREBP2, that utilize solely importin beta 1 for nuclear transport whereas ChREBP can utilize both importins alpha and beta for nuclear translocation. SRTFs such as NF-κB, AP-1, NFAT, STAT1 and STATS are transported to the nucleus in response to proinflammatory stimuli. In the nucleus, SRTFs activate genes that encode mediators of inflammation. Examples of NTMs include SN50, cSN50 and cSN50.1 described in more detail in the following paragraphs, as well as the sequences set forth in Table 1.

Figure 1:
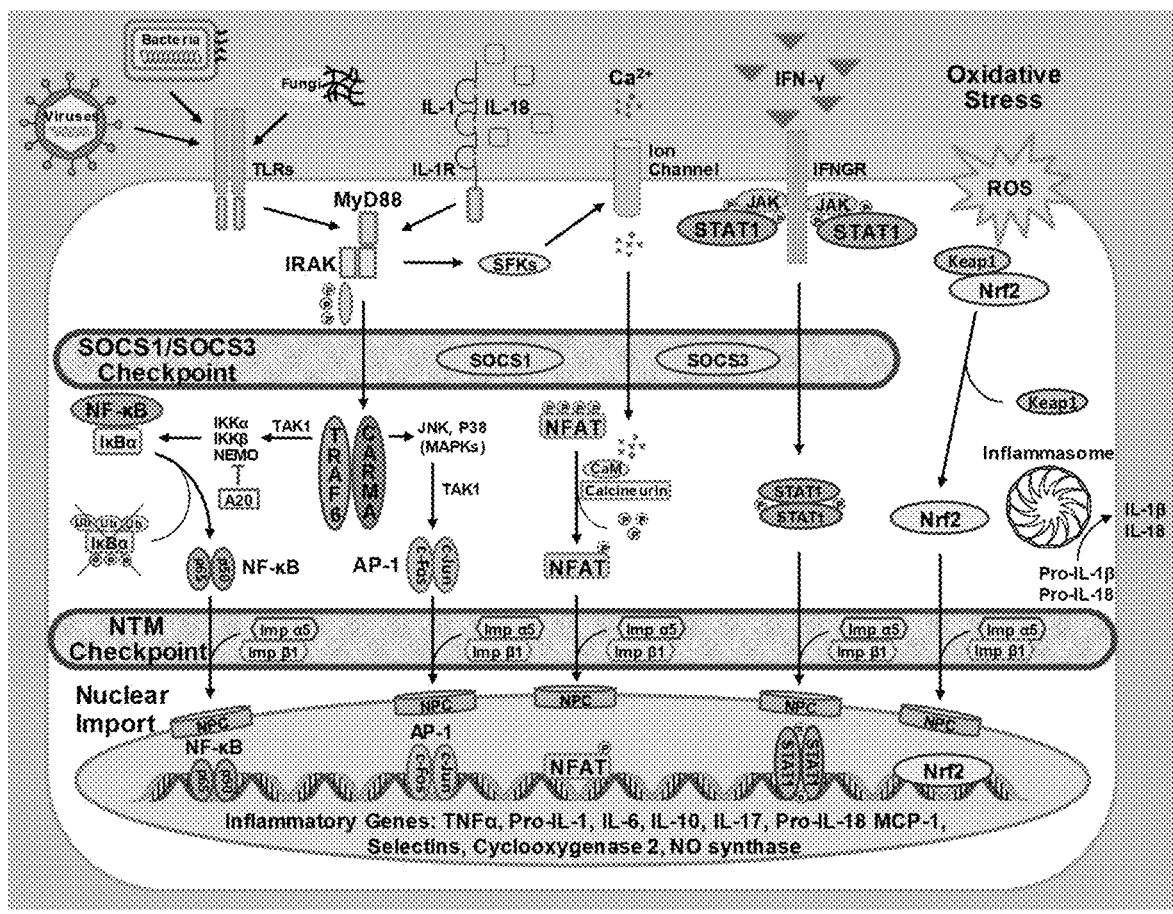
Figure 2:
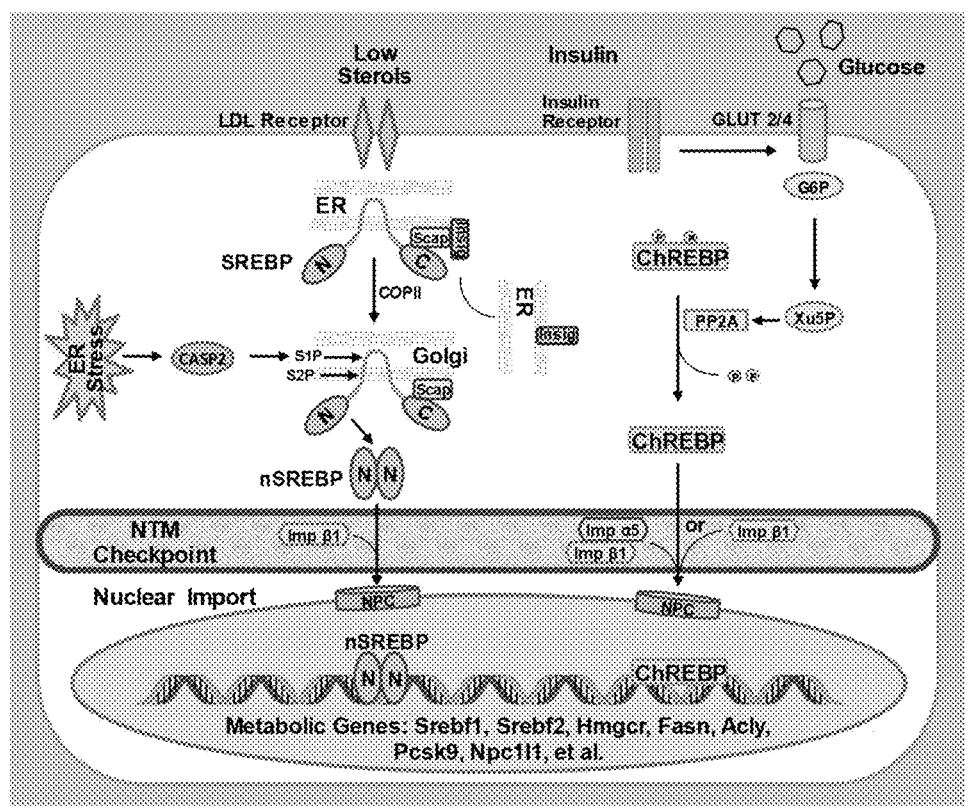
FIG. 2 shows metabolic signaling to the nucleus mediated by metabolic transcription factors that comprise Sterol Regulatory Element-Binding Proteins (SREBPs) and Carbohydrate-Responsive Element-Binding Proteins (ChREBPs).

SN50, cSN50, cSN50.1 and their derivatives inhibit nuclear import of SRTFs by binding to their target, importin alpha 5 (Imp α5) known also as karyopherin α1 (KPNA1, SRP1). Adaptor proteins targeted by these peptides constitute a recognition arm of nuclear import machinery. They recognize nuclear localization sequence (NLS) on SRTFs, ChREBPs or other transcription factors, e.g. NRF2, and carry this cargo across the nuclear pore. Imp α5 (KPNA1/SRP1) forms a complex with importin β1 (Imp β1) which docks at the cytoplasmic rim of the nuclear pore (FIG. 1).

SN50, cSN50, and cSN50.1 and their derivatives also bind Imp β1 and compete with its transporting of SREBP 1 and 2 to the nucleus. As these transcription factors do not display NLS recognized by importins α, their transport is independent of Imp α5. The latter recognizes NLS motif on SRTFs and ChREBPs.

In recent preclinical studies, a highly soluble cell-penetrating NTM (cSN50.1), with dual specificity was used. This NTM has segments that bind both Imp α5, which recognizes NLS derived from NF-κB1, and Imp κ1, which recognizes the signal-sequence hydrophobic region (SSHR) derived from Fibroblast Growth Factor 4. SSHR also serves as a membrane translocating motif (MTM) to enable intracellular delivery of peptides and proteins through an ATP- and endocytosis-independent mechanism. This and other NTMs have been shown to inhibit nuclear translocation of SRTFs and metabolic transcription factors, Sterol Regulatory Element-Binding Proteins (SREBPs) and Carbohydrate-Responsive Element-Binding Proteins (ChREBPs). Thus, these NTMs reduced inflammatory responses, microvascular injury, apoptosis and hemorrhagic necrosis of the liver and other organs as well as metabolic derangements with a concomitant gain in survival, in models of lethal shock induced by bacterial toxins in normal diet fed animals and in metabolic syndrome induced in the High Fat Diet ("Western Diet")-fed animals.

A novel form of immunotherapy that targets nuclear import as described herein can arrest inflammation-driven destruction of microbe-infected tissue and surrounding area of a given organ. With respect to inflammation (such as, for example, acute inflammation, subacute inflammation, chronic inflammation, organ-specific inflammation, systemic inflammation, and/or the end stage of microbial inflammation, sepsis and septic shock), pro-inflammatory signaling initiated through stimulation of the principal receptors of innate immunity, Toll-like receptors (TLRs), is one mechanism that activates non-immune and immune cells. Non-immune cells comprise skin keratinocytes, mucosal epithelial cells, and vascular endothelial cells. They serve as an organ-specific barrier while acting as the first line sentinels. Along with polymorphonuclear leukocytes (neutrophils, eosinophils, basophils) and strategically deployed macrophages, dendritic cells, Natural Killer (NK) cells and group 1,2, and 3 innate lymphoid cells (ILC), non-immune cells alert immune system to the activity of inflammation-causing irritants while they modulate the inflammatory response. Inhibiting nuclear transport at a common "checkpoint" located downstream of TLRs and cytokine receptors globally suppresses expression of inflammatory genes thereby calming the genomic storm and averting multiple organ injury (FIG. 1). Reprograming of gene regulatory networks in response to a multitude of microbial, autoimmune, allergic, metabolic, and physical insults, as well as constitutional factors (inborn errors of immunity), is dependent on signaling to the host cell's nucleus comprising a fundamental process of inflammation (see FIG. 1 for a depiction).

Accordingly, in one aspect, disclosed herein are methods of reducing levels of a Stress-Responsive Transcription Factor (SRTF) and metabolic transcription factors, Sterol Regulatory Element-Binding Proteins (SREBPs) as well as Carbohydrate-Responsive Element-Binding Proteins (ChREBP) in a cell's nucleus at a site of inflammation in a subject with an infection, causing microbial inflammation, or in a subject with an overeating High Fat Diet known as Western Diet rich in fats, carbohydrates, and salt, or a subject consuming ethanol, both causing metabolic inflammation, e.g. non-alcoholic or alcoholic liver disease, comprising administering to the subject a therapeutically effective amount of a composition comprising one or more Nuclear Transport Modifiers (NTMs).

It is understood and herein contemplated that by reducing the levels of SRTF and metabolic transcription factors, Sterol Regulatory Element-Binding Proteins (SREBPs) and Carbohydrate-Responsive Element-Binding Proteins (ChREBPs), in a cell's nucleus, the disclosed NTM can reduce, inhibit, and/or prevent inflammation causing genomic reprogramming (such as, for example, acute inflammation, subacute inflammation, chronic inflammation, organ-specific inflammation, systemic inflammation, and/or end stage of microbial inflammation, sepsis), and consequently, the occurrence of endothelial dysfunction, multi-organ failure and ultimately fatal septic shock associated with sepsis, as the end-stage of microbial inflammation. Accordingly, described herein is a method of treating, inhibiting, reducing, and/or preventing inflammation (such as, for example, acute inflammation, subacute inflammation, chronic inflammation, organ-specific inflammation, systemic inflammation, and/or the end-stage of microbial inflammation, sepsis and septic shock) including, but not limited to microbial disease, liver injury (such as, for example, alcoholic liver disease), autoimmune disease, allergic disease, autoinflammatory disorder, metabolic disorder, neoplastic disorder, inflammatory skin disorder, and/or physical insults (such as trauma, burns, radiation), comprising administering to the subject with the inflammation a composition comprising NTM. In some aspects the NTM can be administered in combination with one or more anti-microbial agents and/or one or more anti-inflammatory agents.

In one aspect, the method for reducing levels of SRTF, SREBPs (such as, for example, SREBP1a, SREBP1c, SREBP2) and ChREBPs (such as ChREBPα and ChREBPβ) in a cell, methods treating, inhibiting, reducing, and/or preventing diseases mediated by inflammation (such as, for example, microbial, allergic, autoimmune, metabolic, physical, and constitutive inflammation in their acute, subacute, chronic stages or organ-specific, systemic inflammation, and/or sepsis as the end-stage of microbial inflammation) include administering a therapeutically effective amount of a composition comprising one or more nuclear transport modifier (NTM) to the mammalian subject. Administration of the composition decreases inflammation by attenuating expression of at least one Stress-Responsive Transcription Factor-regulated gene and/or at least one Sterol-Regulatory Element Binding Proteins (SREBPs)-regulated gene, and/or at least one Carbohydrate-Responsive Element-Binding Proteins (ChREBPs)-regulated gene. Thus, the effective dose is an amount effective for reducing importin alpha-mediated nuclear translocation of at least one stress response Stress-Responsive Transcription Factors (SRTF) or one metabolic transcription factor, Carbohydrate-Responsive Element-Binding Proteins (ChREBPs), and reducing inflammation caused by infection and/or metabolic insult in the mammalian subject. Similarly, the effective dose is an amount effective for reducing importin beta-mediated nuclear translocation of at least one metabolic transcription factors, Sterol-Regulatory Element Binding Protein (SREBP) and reducing inflammation caused by infection and/or metabolic insult in the mammalian subject. The NTM may bind to importin alpha, to importin beta, or to both importin alpha and importin beta.

An important aspect of the Nuclear Transport Modifier exemplified by cSN50.1 peptide and its congeners is their ability to reach the site of inflammation caused by an infectious agent, i.e. the infected host cell, as well as cells in other myeloid, lymphoid, and non-lymphoid organs. The mechanism of intracellular delivery of this class of cell-penetrating peptides has been elucidated as an endocytosis-independent process of crossing the plasma membrane mediated by the membrane-translocating motif (MTM), which is based on the signal sequence hydrophobic region (SSHR) derived from Kaposi FGF (Veach et al. (2004) J Biol Chem 279: 11425-11431). The amphipathic helix-based structure of SSHR facilitates its insertion directly into the plasma membrane and the tilted transmembrane orientation permits the translocation of the Nuclear Transport Modifier through the phospholipid bilayer of the plasma membrane directly to the interior of the cell without perturbing membrane integrity. This mechanism explains the efficient delivery of SSHR-guided cargo across the plasma membrane of multiple cell types involved in microbial, allergic, autoimmune, metabolic, physical, and constitutive inflammation (Hawiger J and Zienkiewicz J (2019) Scand. J. Immunology,00:e12812).

The NTMs disclosed herein are derived from N50-containing NTMs (SN50, cSN50, and cSN50.1) that are comprised of a hydrophilic N50 motif patterned on the nuclear localization sequence (NLS) region of the NF-κB1/p50 subunit (see Table 1) fused to a motif from the signal sequence hydrophobic region (SSHR) of human fibroblast growth factor 4. The SSHR allows peptides to cross the plasma membrane by an ATP- and endosome-independent mechanism, and the N50 motif was designed to bind to importins α during stimulus-initiated signaling and thereby limit docking of NLS-bearing SRTFs to their adaptor proteins and reduce nuclear import of activated STRFs. Any mimetics, derivatives, or homologs of SN50, cSN50, and cSN50.1 may be used in the compositions, methods, and kits disclosed herein.

TABLE 1

Amino Acid Sequences of Peptides Used
Peptide Sequences

| NTM | SSHR | NLS | SEQ ID NO: |
|---|---|---|---|
| N50 | | VQRKRQKLMP | 10 |
| SN50M | AAVALLPAVLLALLAP | VQRDEQKLMP | 11 |
| cN50.1 | | CVQRKRQKLMPC | 12 |
| SN50 | AAVALLPAVLLALLAP | VQRKRQKLMP | 13 |

TABLE 1-continued

Amino Acid Sequences of Peptides Used
Peptide Sequences

| NTM | SSHR | NLS | SEQ ID NO: |
|---|---|---|---|
| SSHR-1 | AAVALLP | | 14 |
| SSHR-2 | AVLLALLAP | | 15 |

N50-sequence derived from the NLS region of NF-κB1/p50;
SN50M-sequence of control peptide with KR to DE mutation (bold faced); cN50.1-sequence of cyclized version of N50 just as cSN50.1 is a cyclized version of SN50. Hydrophobic regions of the SSHR domain are distinguished from the cluster of basic amino acids (NLS). NTM indicates nuclear transport modifier; SSHR, signal sequence hydrophobic region; NLS, nuclear localization sequence.

SN50 is a fragment-linked peptide combining the signal sequence hydrophobic region (SSHR) of the Kaposi fibroblast growth factor (K-FGF) and the nuclear localization signal (NLS) of the p50 subunit of NF-κB1. Any mimetics, derivatives, or homologs of SN50 may be used in the compositions, methods, and kits disclosed herein. The sequence of SN50 is AAVALLPAVLLAL-LAPVQRKRQKLMP (SEQ ID NO: 13). Generation and use of SN50 is described in U.S. Pat. Nos. 6,495,518 and 7,553,929.

cSN50 is a fragment-designed cyclic peptide combining the hydrophobic region of the Kaposi fibroblast growth factor signal sequence with the nuclear localization signal (NLS) of the p50-NFKB1 and inserting a cysteine on each side of the NLS to form an intrachain disulfide bond. The amino acid sequence of cSN50 is AAVALLPAVLLAL-LAPCYVQRKRQKLMPC (SEQ ID NO: 1). Any mimetics, derivatives, or homologs of cSN50 may be used in the compositions, methods, and kits disclosed herein. Methods of making and using cSN50 are described, for example, in U.S. Pat. Nos. 8,324,148 and 9,044,433. These patents are incorporated herein by reference in their entireties.

cSN50.1 is a cyclized peptide having the sequence of cSN50 with the exception that the tyrosine at position 18 of cSN50, adjacent to the first cysteine, has been removed. Methods of making and using cSN50.1 are described, for example, in U.S. Pat. Nos. 8,932,559 and 9,370,549. The amino acid sequence of cSN50.1 is AAVALLPAVLLAL-LAPCVQRKRQKLMPC (SEQ ID NO: 2). The tyrosine at position 18 was removed from the sequence of cSN50 to increase solubility. cSN50 is soluble at levels of ranging from 2.0 mg/mL to 40 mg/mL depending on the method of synthesis and purification whereas cSN50.1 is soluble at levels of at least 100 mg/ml. Any mimetics, derivatives, or homologs of cSN50.1 may be used in the compositions, methods, and kits disclosed herein. cSN50.1 is also encompassed by SEQ ID NO: 3, SEQ ID NO: 4 and SEQ ID NO: 5. Additional examples of NTMs include fragment-designed and synthesized peptides in which cargo is incorporated as two, rather than one, modules or cargos derived from intracellular proteins other than NF-κB 1. Such additional examples include the sequences of SEQ ID NO: 6, SEQ ID NO: 7, SEQ ID NO: 8, and SEQ ID NO: 9.

Accordingly, the Nuclear Transport Modifier (NTM) for use in the disclosed methods of treating, inhibiting, reducing, and/or preventing inflammation-mediated diseases (such as, for example, allergic, autoimmune, metabolic, microbial, physical, and constitutive inflammation comprising organ-specific or systemic inflammation, such as sepsis as the end stage microbial inflammation) including, but not limited to liver injury (such as, for example, alcoholic liver disease), may be, for example, an NTM having the sequence Xaa Xaa Xaa Xaa Leu Leu Pro Xaa Xaa Leu Leu Ala Leu Leu Ala Pro Xaa Xaa Xaa Xaa Gln Arg Lys Arg Gln Lys Xaa Xaa Xaa Xaa (SEQ ID NO: 3), wherein Xaa is any amino acid or is absent. For example, the Nuclear Transport Modifier can have the sequence Xaa Xaa Xaa Xaa Leu Leu Pro Xaa Xaa Leu Leu Ala Leu Leu Ala Pro Cys Xaa Xaa Gln Arg Lys Arg Gln Lys Xaa Xaa Xaa Cys, where Xaa is any amino acid or is absent (SEQ ID NO: 4). As another example, the Nuclear Transport Modifier can have the sequence Xaa Xaa Xaa Xaa Leu Leu Pro Xaa Xaa Leu Leu Ala Leu Leu Ala Pro Cys Xaa Gln Arg Lys Arg Gln Lys Xaa Xaa Xaa Cys, where Xaa is any amino acid or is absent (SEQ ID NO: 5). In one embodiment, the Nuclear Transport Modifier is cSN50.1 having the sequence set forth in SEQ ID NO: 2. In another example of an NTM, the NTM has the sequence Xaa Xaa Xaa Xaa Leu Leu Pro Xaa Xaa Leu Leu Ala Val Leu Ala Pro Xaa Xaa Xaa Gln Arg Lys Arg Gln Lys Xaa Xaa Xaa Xaa, where Xaa is any amino acid or is absent (SEQ ID NO: 6). In yet another example, the NTM has the sequence Ala Ala Val Ala Leu Leu Pro Ala Val Leu Leu Ala Val Leu Ala Pro Cys Val Gln Arg Lys Arg Gln Lys Leu Met Pro Cys (SEQ ID NO: 7). In a further example, the NTM has the sequence Xaa Xaa Xaa Xaa Leu Leu Pro Xaa Xaa Leu Leu Ala Leu Leu Ala Pro Xaa Xaa Gln Arg Asp Glu Gln Lys Xaa Xaa Xaa Xaa, where Xaa is any amino acid or is absent (SEQ ID NO: 8). In another example, the NTM has the sequence Xaa Xaa Xaa Xaa Leu Leu Pro Xaa Xaa Leu Leu Ala Leu Leu Ala Pro Cys Xaa Gln Arg Asp Glu Gln Lys Xaa Xaa Xaa Cys (SEQ ID NO: 9).

1. Compositions for Treating Diseases and Disorders Mediated by Inflammation in a Subject Compositions (e.g., pharmaceutical compositions) described herein for treating diseases mediated by inflammation (including, but not limited to acute inflammation, subacute inflammation, chronic inflammation, organ-specific inflammation, systemic inflammation, and/or sepsis), said diseases including, but not limited to microbial disease, liver injury (such as, for example, alcoholic liver disease), autoimmune disease, allergies, autoinflammatory disorder, metabolic disorder, neoplastic disorder, inflammatory skin disorder, and/or physical insults include a pharmaceutically acceptable carrier and at least one importin beta-selective and/or at least one importin alpha-selective NTM in an amount effective for modifying (e.g., decreasing) entry into the nucleus of at least one transcription factor that includes but is not limited to NF-κB, AP-1, NFAT, STAT1, STAT5, SREBP1a, SREBP1c, and SREBP2, and ChREBPs that utilize importins alpha and/or beta for nuclear transport, and treating or preventing the disease. For example, entry of at least one SREBP into the nucleus is reduced. As mentioned above, NTMs modulate signaling to the nucleus mediated by transcription factors that include but are not limited to NF-κB, AP-1, NFAT, STAT1, STAT5, that utilize importins alpha and beta heterodimer, SREBP1a, SREBP1c, and SREBP2, that utilize solely importin beta for nuclear transport whereas ChREBP can utilize both importins alpha and beta for nuclear translocation. In this example, the importin beta-selective NTM reduces nuclear translocation of the nuclear forms of SREBP1a, SREBP1c, SREBP2, and partially ChREBPs. Any suitable importin beta-selective NTM may be used. Examples of importin beta-selective NTMs include but are not limited to peptide sequences that include an SSHR domain listed in Table 2 below and a cargo listed in Table 1 below. One example of such an importin beta-selective NTM is AAVALLPAVLLALLAPVQRDEQKLMP (SEQ ID NO: 11) as listed in Table 1 above. Additional examples of peptides designed to inhibit interaction of importin alpha with importin beta necessary for the formation of their heterodimer include AAVALLPAVLLALLAPRRRRIEVNVELRKAKK (SEQ ID NO: 18) (referred to as SIBB in Table 2), AAVALLPAVLLALLAPRRRRIEVNVELRKAKKDD (SEQ ID NO: 19) (referred to as SI-1 in Table 2). AAVALLPAVLLALLAPRRQRNEVVVELRKNKRDE (SEQ ID NO: 20) (referred to as SI-3 in Table 2), AAVALLPAVLLALLAPRRHRNEVTVELRKNKRDE (SEQ ID NO: 21) (referred to as SI-4 in Table 1), AAVALLPAVLLALLAPRRRREEEGLQLRKQKREE (SEQ ID NO: 22) (referred to as SI-5 in Table 2), AAVALLPAVLLALLAPRRRREEEGIQLRKQKREQ (SEQ ID NO: 23) (referred to as SI-7 in Table 2) and AAVALLPAVLLALLAPCTEMRRRRIEVC (SEQ ID NO: 24) (referred to as cSIB in Table 2). The examples of peptides designed to be specific inhibitors of importins alpha include AAVALLPAVLLALLAPVELRKAKKDDQMLKRRNVSSF (SEQ ID NO: 25) (referred to as SAR1 in Table 2), AAVALLPAVLLALLAPVELRKNKRDEHLLKRRNVPHE (SEQ ID NO: 26) (referred to as SAR3 in Table 2), AAVALLPAVLLALLAPVELRKNKRDEHLLKKRNVPQE (SEQ ID NO: 27) (referred to as SAR4 in Table 2), AAVALLPAVLLALLAPLQLRKQKREEQLFKRRNVATA (SEQ ID NO: 28) (referred to as SARS in Table 2), AAVALLPAVLLALLAPIQLRKQKREQQLFKRRNVELI (SEQ ID NO: 29) (referred to as SAR7 in Table 2), AAVALLPAVLLALLAPCVELRKAKKDDQC (SEQ ID NO: 30) (referred to as cSAR1-C in Table 2), AAVALLPAVLLALLAPCVELRKNKRDEHC (SEQ ID NO: 31) (referred to as cSAR3-C in Table 2), AAVALLPAVLLALLAPCLQLRKQKREEQC (SEQ ID NO: 32) (referred to as cSAR5-C in Table 2), AAVALLPAVLLALLAPCIQLRKQKREQQC (SEQ ID NO: 33) (referred to as cSAR7-C in Table 2), AAVALLPAVLLALLAPCQMLKRRNVSSFC (SEQ ID NO: 34) (referred to as cSAR1-N in Table 2), AAVALLPAVLLALLAPCHLLKRRNVPHEC (SEQ ID NO: 35) (referred to as cSAR3-N in Table 2), AAVALLPAVLLALLAPCHLLKKRNVPQEC (SEQ ID NO: 36) (referred to as cSAR4-N in Table 2), AAVALLPAVLLALLAPCQLFKRRNVATAC (SEQ ID NO: 37) (referred to as cSAR5-N in Table 2), and AAVALLPAVLLALLAPCQLFKRRNVELIC (SEQ ID NO: 38) (referred to as cSAR7-N in Table 2). It is to be understood that any derivatives and/or analogues of these sequences are encompassed by the invention.

In one embodiment, an NTM as described herein has the sequence AAVALLPAVXLAXXAPVELRKNKRDEHLLKRRNVPHE (SEQ ID NO: 39). Additional NTMs include SEQ ID NOs: 1-9, 13, and 16-41. It is to be understood that any derivatives and/or analogues of these sequences are encompassed by the invention.

An NTM as described herein may be an inhibitor of an importin alpha 3 interaction with importin beta.

The SI-3 sequence (see Table 2) is designed to block an interaction between importin alpha and importin beta. Hence, this peptide is a cell-penetrating inhibitor of an importin alpha and importin beta interaction. It is to be understood that any derivatives and/or analogues of this sequence is encompassed by the invention.

TABLE 2

| Peptide sequences | | | | |
|---|---|---|---|---|
| | SSHR[§] | Cargo | SEQ ID NO: | Comments |
| SM12 | AAVALLPAVLLALLAP | VQRDEQKLMP | 11 | Importin beta-selective inhibitor (binding studies) |
| SIBB | AAVALLPAVLLALLAP | RRRRIEVNVELRKAKK | 18 | Inhibitor of Imp alpha 1-importin beta interaction |
| SI-1 | AAVALLPAVLLALLAP | RRRRIEVNVELRKAKKDD | 19 | Inhibitor of Imp alpha 1-importin beta interaction |
| SI-3 | AAVALLPAVLLALLAP | RRQRNEVVVELRKNKRDE | 20 | Inhibitor of Imp alpha 3-importin beta interaction |
| SI-4 | AAVALLPAVLLALLAP | RRHRNEVTVELRKNKRDE | 21 | Inhibitor of Imp alpha 4-importin beta interaction |
| SI-5 | AAVALLPAVLLALLAP | RRRREEEGLQLRKQKREE | 22 | Inhibitor of Imp alpha 5-importin beta interaction |
| SI-7 | AAVALLPAVLLALLAP | RRRREEEGIQLRKQKREQ | 23 | Inhibitor of Imp alpha 7-importin beta interaction |
| SAR1 | AAVALLPAVLLALLAP | VELRKAKKDDQMLKRRNVSSF | 25 | Imp alpha 1-specific |
| SAR3 | AAVALLPAVLLALLAP | VELRKNKRDEHLLKRRNVPHE | 26 | Imp alpha 3-specific |

TABLE 2-continued Peptide sequences

| | SSHR[§] | Cargo | SEQ ID NO: | Comments |
|---|---|---|---|---|
| SAR4 | AAVALLPAVLLALLAP | VELRKNKRDEHLLKKRNVPQE | 27 | Imp alpha 4-specific |
| SAR5 | AAVALLPAVLLALLAP | LQLRKQKREEQLFKRRNVATA | 28 | Imp alpha 5-specific |
| SAR7 | AAVALLPAVLLALLAP | IQLRKQKREQQLFKRRNVELI | 29 | Imp alpha 7-specific |
| cSN50.1 | AAVALLPAVXLAXXAP | CVQRKRQKLMPC | 2 | Imp alpha 5-selective |
| cSM12 | AAVALLPAVLLALLAP | CVQRDEQKLMPC | 40 | Imp beta-selective (cell culture and preclinical studies) |
| cSIB | AAVALLPAVLLALLAP | CTEMRRRRIEVC | 24 | Inhibitor of Imp alpha 1-importin beta interaction |
| cSAR1-C | AAVALLPAVLLALLAP | CVELRKAKKDDQC | 30 | Imp alpha 1-specific Proximal to C-terminal |
| cSAR3-C | AAVALLPAVLLALLAP | CVELRKNKRDEHC | 31 | Imp alpha 3-specific Proximal to C-terminal |
| cSAR5-C | AAVALLPAVLLALLAP | CLQLRKQKREEQC | 32 | Imp alpha 5-specific Proximal to C-terminal |
| cSAR7-C | AAVALLPAVLLALLAP | CIQLRKQKREQQC | 33 | Imp alpha 7-specific Proximal to C-terminal |
| cSAR1-N | AAVALLPAVLLALLAP | CQMLKRRNVSSFC | 34 | Imp alpha 1-specific Proximal to N-terminal |
| cSAR3-N | AAVALLPAVLLALLAP | CHLLKRRNVPHEC | 35 | Imp alpha 3-specific Proximal to N-terminal |
| cSAR4-N | AAVALLPAVLLALLAP | CHLLKKRNVPQEC | 36 | Imp alpha 4-specific Proximal to N-terminal |
| cSAR5-N | AAVALLPAVLLALLAP | CQLFKRRNVATAC | 37 | Imp alpha 5-specific Proximal to N-terminal |
| cSAR7-N | AAVALLPAVLLALLAP | CQLFKRRNVELIC | 38 | Imp alpha 7-specific Proximal to N-terminal |

[§]Signal Sequence Hydrophobic Region (SSHR)

"Cargo" comprises sequences of functionally active hydrophilic motifs (fragments) listed as linear or cyclized peptides through addition of cysteine at the amino- and carboxy-termini of respective linear peptides. Both linear and cyclized sequences are fused to hydrophobic membrane translocation motif denoted SSHR.

In one aspect disclosed herein are methods of treating, inhibiting, reducing, and/or preventing diseases mediated by inflammation (such as, for example, acute inflammation, subacute inflammation, chronic inflammation, organ-specific inflammation, systemic inflammation, and/or sepsis) said diseases including, but not limited to microbial disease, liver injury (such as, for example, alcoholic liver disease), autoimmune disease, autoinflammatory disorder, metabolic disorder, neoplastic disorder, inflammatory skin disorder, and/or physical insults in a subject comprising administering to the subject an anti-microbial agent and a composition comprising one or more NTMs including, but not limited to SN50 having the sequence set forth in SEQ ID NO: 1 or cSN50.1 having the sequence set forth in SEQ ID NO: 2, cSN50.1 beta having the sequence set forth in SEQ ID NO: 40, or any of the NTMs disclosed herein having the amino acid sequence set forth in SEQ ID NO: 3; SEQ ID NO: 4; SEQ ID NO: 5; SEQ ID NO: 6, SEQ ID NO: 7, SEQ ID NO: 8, SEQ ID NO: 9, SEQ ID NO: 11, SEQ ID NO: 13, SEQ ID NO: 17, SEQ ID NO: 18, SEQ ID NO: 19; SEQ ID NO: 20; SEQ ID NO: 21; SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29; SEQ ID NO: 30; SEQ ID NO: 31; SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, and/or SEQ ID NO: 41. In one aspect the NTM can be cSN50.1 beta comprising the amino acid sequence AAVALLPAVLLAL-LAPCVQRDEQKLMPC (SEQ ID NO: 40). cSN50.1 beta is a cyclized peptide having the sequence of cSN50.1 with the exception that the lysine at the position 21 has been replaced by aspartic acid and the arginine residue at the position of 22 has been replaced by glutamic acid.

As noted above, the methods disclosed herein can be used in treating, inhibiting, reducing, and/or preventing diseases mediated by inflammation (such as, for example, acute inflammation, subacute inflammation, chronic inflammation, organ-specific inflammation, systemic inflammation, and/or sepsis) said diseases including, but not limited to microbial disease, liver injury (such as, for example, alcoholic liver disease), autoimmune disease, autoinflammatory disorder, metabolic disorder, neoplastic disorder, inflammatory skin disorder, and/or physical insults. In one aspect, disclosed herein are methods of treating, inhibiting, reducing, and/or preventing diseases mediated by inflammation (such as, for example, acute inflammation, subacute inflammation, chronic inflammation, organ-specific inflammation, systemic inflammation, and/or sepsis) said diseases including, but not limited to microbial disease, liver injury (such as, for example, alcoholic liver disease), autoimmune disease, autoinflammatory disorder, metabolic disorder, neoplastic disorder, inflammatory skin disorder, and/or physical insults in a subject comprising administering to a subject a therapeutically effective amount of an anti-microbial agent and a composition comprising one or more NTM (such as, for example, SEQ ID NO: 1, SEQ ID NO: 2, SEQ ID NO: 3; SEQ ID NO: 4; SEQ ID NO: 5; SEQ ID NO: 6, SEQ ID NO: 7, SEQ ID NO: 8, SEQ ID NO: 9, SEQ ID NO: 11, SEQ ID NO: 13, SEQ ID NO: 16, SEQ ID NO: 17, SEQ ID NO: 18, SEQ ID NO: 19; SEQ ID NO: 20; SEQ ID NO: 21; SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29; SEQ ID NO: 30; SEQ ID NO: 31; SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39; SEQ ID NO: 40; and/or SEQ ID NO: 41).

It is understood and herein contemplated that one of the deleterious effects of inflammation (such as, for example, allergic, autoimmune, metabolic, microbial, physical, and constitutive inflammation comprising organ-specific or systemic inflammation exemplified by sepsis as the end stage of microbial inflammation) including, but not limited to liver injury (such as, for example, alcoholic liver disease) at different stages of a disease (acute, subacute, and chronic) including microbial disease, autoimmune disease, autoinflammatory disorder, metabolic disorder, neoplastic disorder, inflammatory skin disorder, and/or physical insults. As a result of inflammation (such as, for example, allergic, autoimmune, metabolic, microbial, physical, and constitutive inflammation comprising organ-specific or systemic inflammation exemplified by sepsis as the end stage of microbial inflammation) including, but not limited to liver injury (such as, for example, alcoholic liver disease), at different stages of a disease (acute, subacute, and chronic) including, but not limited to microbial disease, liver injury (such as, for example, alcoholic liver disease), autoimmune disease, autoinflammatory disorder, metabolic disorder, neoplastic disorder, inflammatory skin disorder, and/or physical insults, many pro- and anti-inflammatory cytokines are produced resulting in the microvascular endothelial injury that evokes activation and deposition of blood platelets thereby resulting in their "consumption" manifested by a decreased platelet count in the blood (thrombocytopenia). This process is accompanied by generation of clotting enzyme, thrombin, but also results in production of plasminogen activator that leads to formation of fibrinolytic enzyme, plasmin. Thus, fibrinogen can be depleted and both uncontrolled thrombi formation and bleeding may occur while circulating platelets are depleted, a process known as thrombocytopenia without or with Disseminated Intravascular Coagulation. Typical platelet counts for adults is between 150,000 and 400,000/µL, but these numbers can be less 80,000/µL due to microvascular endothelial injury. In one aspect, it is understood that by treating the microvascular endothelial dysfunction in the subject displaying the inflammation, the thrombocytopenia is ameliorated. Therefore, disclosed herein are methods of treating/inhibiting/reducing thrombocytopenia associated with inflammation (such as, for example, acute inflammation, subacute inflammation, chronic inflammation, organ-specific inflammation, systemic inflammation, and/or sepsis) including, but not limited to microbial disease, liver injury (such as, for example, alcoholic liver disease), autoimmune disease, autoinflammatory disorder, metabolic disorder, neoplastic disorder, inflammatory skin disorder, and/or physical insults in a subject comprising administering to the subject a therapeutically effective amount of a composition comprising one or more NTM (such as, for example, SEQ ID NO: 1, SEQ ID NO: 2, SEQ ID NO: 3; SEQ ID NO: 4; SEQ ID NO: 5; SEQ ID NO: 6, SEQ ID NO: 7, SEQ ID NO: 8, SEQ ID NO: 9, SEQ ID NO: 11, SEQ ID NO: 13, SEQ ID NO: 16, SEQ ID NO: 17, SEQ ID NO: 18, SEQ ID NO: 19; SEQ ID NO: 20; SEQ ID NO: 21; SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29; SEQ ID NO: 30; SEQ ID NO: 31; SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39; SEQ ID NO: 40; and/or SEQ ID NO: 41). It is understood and herein contemplated that the disclosed methods of treating, inhibiting, or reducing thrombocytopenia can further comprise the addition of an anti-microbial agent and/or an anti-inflammatory agent.

It is also understood and herein contemplated that proinflammatory signaling to the nucleus has also been implicated in rapid glycogen depletion in the liver during inflammation (such as, for example, during microbial inflammation or alcoholic liver disease). However, as shown herein, NTM treatment prevented glycogenolysis that is dependent on the nuclear transport of metabolic transcription factors ChREBPs and leads to the increase of blood glucose (hyperglycemia) and triglycerides (hypertriglyceridemia). Thus, in one aspect, disclosed herein are methods of reducing/inhibiting/preventing metabolic derangements mediated by inflammation (including, but not limited to acute inflammation, subacute inflammation, chronic inflammation, organ-specific inflammation, systemic inflammation, and/or sepsis), said diseases including, but not limited to microbial disease, liver injury (such as, for example, alcoholic liver disease), autoimmune disease, allergies, autoinflammatory disorder, metabolic disorder, neoplastic disorder, inflammatory skin disorder, and/or physical insults in a subject comprising administering to the subject an NTM (such as, for example, SEQ ID NO: 1, SEQ ID NO: 2, SEQ ID NO: 3; SEQ ID NO: 4; SEQ ID NO: 5; SEQ ID NO: 6, SEQ ID NO: 7, SEQ ID NO: 8, SEQ ID NO: 9, SEQ ID NO: 11, SEQ ID NO: 13, SEQ ID NO: 16, SEQ ID NO: 17, SEQ ID NO: 18, SEQ ID NO: 19; SEQ ID NO: 20; SEQ ID NO: 21; SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29; SEQ ID NO: 30; SEQ ID NO: 31; SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39; SEQ ID NO: 40; and/or SEQ ID NO: 41). In one aspect, the methods of reducing/inhibiting/preventing inflammation associated liver glycogenolysis can further comprise the administration of an anti-microbial agent or additional anti-inflammatory agent.

Accordingly, described herein is a composition for treating an inflammatory disease or disorder (e.g., autoimmune, microbial, metabolic, neoplastic, posttraumatic, and autoinflammatory disease) in a subject. The composition includes a pharmaceutically acceptable carrier and at least one (e.g., one, two, three, etc.) importin beta-selective NTM including an SSHR domain and a cargo that does not bind to any importin alpha, or at least one (e.g., one, two, three, etc.) importin alpha-selective NTM, in an amount effective for modifying entry of at least one (e.g., one, two, three, etc.) transcription factor (e.g., NF-κB, AP-1, NFAT, STAT1, SREBP1a, SREBP1c, and SREBP2, and ChREBP) into a cell's (e.g., a mammalian cell's) nucleus and for treating the inflammatory disease or disorder. The at least one importin alpha-selective NTM is a peptide or compound that binds to one or more binding pockets of an importin alpha and that modulates nuclear transport of at least one intracellular protein. Modifying entry of at least one transcription factor into a cell's nucleus includes inhibiting entry of the at least one transcription factor into the cell's nucleus. The at least one importin beta-selective NTM can have an amino acid sequence AAVALLPAVLLALLAPVQRDEQKLMP (SEQ ID NO: 11). The at least one importin alpha-selective NTM can have, for example, the amino acid sequence AAVALL-PAVXLAXXAPCVQRKRQKLMPC (SEQ ID NO: 41). The composition can be administered with a corticosteroid or a non-steroidal anti-inflammatory agent. In another embodiment, the composition can further include a corticosteroid or a non-steroidal anti-inflammatory agent. The non-steroidal anti-inflammatory agent can be, for example, acetaminophen or ibuprofen.

Also described herein is a method of treating or preventing inflammation in a mammalian subject (e.g., a human subject having an autoimmune, allergic, metabolic, microbial, posttraumatic, autoinflammatory or neoplastic disease). The method includes administering a composition including a pharmaceutically acceptable carrier and at least one importin beta-selective NTM including an SSHR domain and a cargo to the mammalian subject in an amount effective for modifying entry of at least one transcription factor (e.g., SREBP1a, SREBP1c, and SREBP2, and ChREBP) into a cell's nucleus and for treating or preventing inflammation in the mammalian subject. In the method, the at least one importin beta-selective NTM binds to and inhibits the activity of at least one importin beta. Modifying entry of at least one transcription factor into a cell's nucleus includes inhibiting entry of the at least one transcription factor into the cell's nucleus. Administration of the composition generally results in inhibition of at least one signaling pathway associated with the inflammation. The at least one importin beta-selective NTM can have an amino acid sequence from the NTM sequences disclosed herein. The composition can be administered by any suitable route, e.g., topically, intranasally, orally, intravenously, or subcutaneously.

Further described herein is a method of treating or preventing inflammation in a mammalian subject. The method includes administering a composition including a pharmaceutically acceptable carrier and at least one importin alpha-selective NTM to the mammalian subject in an amount effective for modifying entry of at least one transcription factor into a cell's nucleus and for treating or preventing inflammation in the mammalian subject. The at least one important alpha-selective NTM is a peptide or compound that binds to one or more binding pockets of an importin alpha and that modulates nuclear transport of at least one intracellular protein. The at least one importin alpha-selective NTM can be an importin alpha 5-specific NTM or importin alpha 1-specific or importin alpha3-specific NTM or importin alpha 4-specific and an importin alpha 7-specific NTM. The at least one importin alpha-selective NTM can have the amino acid sequence AAVALL-PAVXLAXXAPCVQRKRQKLMPC (SEQ ID NO: 41). The at least one importin alpha-selective NTM binds to and inhibits the activity of the at least one importin alpha. Modifying entry of at least one transcription factor into a cell's nucleus includes inhibiting entry of the at least one transcription factor into the cell's nucleus. The at least one importin alpha-selective NTM can be specific for importin alpha 5, for example. In some embodiments, the at least one importin alpha-selective NTM includes an Importin Alpha Diversity Region 1 or 2 sequence. The composition can be administered with a corticosteroid or a non-steroidal anti-inflammatory agent. In another embodiment, the composition can further include a corticosteroid or a non-steroidal anti-inflammatory agent. The non-steroidal anti-inflammatory agent can be, for example, acetaminophen or ibuprofen.

Yet further described herein is a method of treating or preventing inflammation in a mammalian subject. The method includes administering a composition including a pharmaceutically acceptable carrier and at least one agent that inhibits an interaction between at least one importin alpha (e.g., importin alpha 1, importin alpha 3, importin alpha 4, importin alpha 5 and importin alpha 7), and at least one importin beta and that modulates nuclear transport of at least one intracellular protein, to the mammalian subject in an amount effective for modifying entry of at least one transcription factor into a cell's nucleus and for treating or preventing inflammation in the mammalian subject. Typically, the at least one agent binds specifically to the at least one importin alpha and is an importin alpha-selective inhibitor.

2. Alcohol Abuse and Liver Injury.

Alcoholic liver disease (ALD) encompasses fatty liver, alcoholic hepatitis, and cirrhosis. Liver cirrhosis was the 12$^{th}$ leading cause of death in 2000 (Mann R E, Smart R G, and Govoni R (2003) Alcohol Research & Health). It affects an estimated 2 million persons in the US. Among these cases, the combination of liver cirrhosis and alcoholic hepatitis contributes to an astounding 65% mortality rate over a 4-year period, a toll greater than many oncologic diseases. The mechanism of ALD progression is vested in inflammation and apoptosis which are tightly linked to innate and adaptive immunity. Whereas adaptive immunity plays a role in some autoimmune disorders of the liver, innate immunity contributes to inflammation by overstimulation of highly conserved Toll-like Receptors (TLRs). TLRs enable phagocytes, exemplified by Kupffer cells in the liver, to prospect their microenvironment for LPS, lipoteichoic acids, viral RNA, and/or bacterial DNA, which provide the source for proinflammatory cues. In turn, these cues evoke intracellular signaling to the nucleus to reset the genome to proinflammatory and proapoptotic program. Thus, TLRs contribute to the development of hepatitis induced by a wide range of microbial agents. This process is intensified when the gut epithelial-blood barrier is compromised by alcohol and the flow of LPS and other microbial products from the gut to the liver is increased. Persistent signaling to the nucleus through TLRs on Kupffer cells leads to the activation of genes that encode cytokines, chemokines, signal transducers (COX2, iNOS), cell adhesion molecules, and other mediators of inflammation. Some of these mediators contribute to the generation of oxygen and nitrogen-reactive intermediates which contribute to EtOH-induced tissue injury. Depending on the potency and duration of this response, direct and/or collateral liver damage can occur, physiologic suppressors of inflammation/apoptosis are overwhelmed, and the continuing injury leads to apoptosis/necrosis of hepatocytes. Due to the glaring lack of anti-inflammatory and cytoprotective drugs that can effectively control this response, alcoholic liver disease now represents the fourth leading cause of death among city dwellers in the US.

Inflammatory liver injury is mediated by cytokines and chemokines, which are produced primarily by mononuclear phagocytes such as Kupffer cells in the liver and other macrophages in extrahepatic sites. Moreover, Innate Lymphoid Cells (ILC) and the subsets of T lymphocytes including NK-T cells are contributory. In response to proinflammatory microbial cues sensed by their TLRs and/or cytokine receptors, these cells send intracellular signals to Stress-Responsive Transcription Factor (SRTFs; see FIG. 1). SRTFs encompass Nuclear Factor-κB (NF-κB), Activator Protein (AP1) comprised of c-Fos and c-Jun, Nuclear Factor of Activated T cells (NFAT) and Signal Transduction and Transcription (STAT) 1 and 3. SRTFs are regulated by kinases, phosphatases, and ubiquitinating enzymes. For example, NF-κB is kept in check by 1κB inhibitory proteins, which are targeted for phosphorylation, ubiquitination, and proteasome-mediated degradation during an inflammatory response. In contrast to NF-κB, NFAT is activated via dephosphorylation involving the phosphatase calcineurin. Calcineurin is regulated by Ca++, calmodulin, and cyclophilins, targeted by cyclosporin and other immunosuppressants.

Proinflammatory cytokines TNFα and IFNγ play a key role in experimentally produced inflammatory injury of the liver that culminates in massive apoptosis and necrosis. This injury is ablated in mice lacking cognate receptors for these cytokines. As shown herein, TNFα responds almost immediately to proinflammatory inducers, LPS and superantigen SEB, in two distinct models of inflammatory liver injury mediated by macrophages (Kupffer cells) and T cells, respectively. Its rapid rise at 90 min is followed by a steep decline due to negative regulation of transcript stability through the 3' untranslated region. Ethanol counteracts this destabilizing process. TNFα interacts with its cognate receptors, TNFR1 and TNFR2. Trimerization of the TNFR1 that bears death domain in its cytoplasmic tail attracts the death domain of a cytoplasmic adaptor protein called TRADD. Further interaction of TRADD with TRAF2 initiates signaling cascades for the activation of caspases, JNK, and/or NF-κB. The nuclear import machinery, importin α5/importin γ1 complex (that is targeted by NTM peptides) translocates NF-κB to the nucleus. Nuclear transport of NF-κB culminates in transcriptional activation of genes encoding multiple mediators and suppressors of inflammation. Upon binding to its cognate receptor, INFγ induces the activation of Janus Protein Tyrosine Kinases (JAK) 1 and 2. A phosphotyrosine-docking site is formed for binding of STAT-1 through its SH2 domain. STAT-1 is phosphorylated on a critical tyrosine residue, prompting the formation of a STAT-1 dimer. The nuclear import machinery, importin α5/importin β1 complex (that is targeted by NTM peptides) translocates the STAT-1 dimer to the nucleus, where it interacts with regulatory elements in the promoter of multiple IFNγ responsive genes. These genes encode cytokines, proapoptotic factors, signal transducers (NADPH oxidase complex generating Reactive Oxygen Intermediates), MHC molecules, antiviral and antibacterial inhibitors. While IFN gamma signaling through its cognate receptor and STAT1 is very important for raising the level of immune response toward intracellular pathogens, e.g. mycobacteria and some viruses, its excessive signaling contributes to apoptosis and necrosis of metabolically-compromised liver challenged with pathogen-derived agonists such as LPS and superantigen SEB. Importantly, apoptosis of hepatocytes can occur in fulminant hepatitis, an inflammatory process that is caused by viral and non-viral agents. For example, gene therapy approaches to correct an inborn error of metabolism led to fulminant liver failure due to the inflammatory response to viral vectors for delivered genes. This inflammation-related complication of gene therapy impedes broader application of viral vectors. The sequence of intracellular signaling events that lead to ultimately fatal liver apoptosis in fulminant liver inflammation remains incompletely understood.

In one aspect, disclosed herein are methods of treating/inhibiting/reducing inflammatory liver injury in a subject comprising administering to the subject a therapeutically effective amount of a composition comprising a Nuclear Transport Modifier (NTM) such as, for example, an NTM that comprises the sequence set forth in SEQ ID NO: 1, SEQ ID NO: 2, SEQ ID NO: 3; SEQ ID NO: 4; SEQ ID NO: 5; SEQ ID NO: 6, SEQ ID NO: 7, SEQ ID NO: 8, SEQ ID NO: 9, SEQ ID NO: 11, SEQ ID NO: 13, SEQ ID NO: 16, SEQ ID NO: 17, SEQ ID NO: 18, SEQ ID NO: 19; SEQ ID NO: 20; SEQ ID NO: 21; SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29; SEQ ID NO: 30; SEQ ID NO: 31; SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39; SEQ ID NO: 40; and/or SEQ ID NO: 41. In one aspect, the inflammatory liver disease is caused by ethanol such as in alcoholic liver disease.

3. Methods of Treating Skin Disorders

In one aspect, disclosed herein are methods of treating/inhibiting/reducing an inflammatory skin disorder (such as, for example, a skin disorder caused by microbial disease, autoimmune disease, autoinflammatory disorder, metabolic disorder, neoplastic disorder, and/or physical insults that are mediated by inflammation) or inflammatory symptoms caused by a skin disorder in a subject comprising administering to the subject a therapeutically effective amount of a composition comprising one or more Nuclear Transport Modifier (NTM) such as, for example, an NTM that comprises the sequence set forth in SEQ ID NO: 1, SEQ ID NO: 2, SEQ ID NO: 3; SEQ ID NO: 4; SEQ ID NO: 5; SEQ ID NO: 6, SEQ ID NO: 7, SEQ ID NO: 8, SEQ ID NO: 9, SEQ ID NO: 11, SEQ ID NO: 13, SEQ ID NO: 16, SEQ ID NO: 17, SEQ ID NO: 18, SEQ ID NO: 19; SEQ ID NO: 20; SEQ ID NO: 21; SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29; SEQ ID NO: 30; SEQ ID NO: 31; SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39; SEQ ID NO: 40; and/or SEQ ID NO: 41.

As noted herein, inflammatory skin disorders can be caused by any number on insults including, but not limited to a skin disorder caused by a microbial infection (i.e, microbial inflammation). It is understood and herein contemplated that inflammation is a mechanism of disease caused by infection ("microbial insult"). An inflammatory skin disorder caused by a microbial insult evolves from innate immune response to an infection due to a microbe such as, for example, a virus, bacterium, fungus, or parasite. Thus, the microbial injury caused by microbial virulence factors is aggravated by the host-produced inflammatory mediators that impede the clearance of invading microbes and add insult to organ's injury. It is understood and herein contemplated that the inflammation and its end stage, sepsis, can result from any microbial insult elicited by known (or unknown) virulence factors and microbial antigens. Accordingly, in one aspect, disclosed herein are methods of treating an inflammatory skin disorder; wherein the inflammatory skin disorder is caused by a microbial disease such as, for example, a virus, bacterium, fungus, and/or parasite.

In one aspect, disclosed herein are methods of treating an inflammatory skin disorder; wherein the inflammatory skin disorder is caused by a viral infection, such as, for example, an infection with a virus selected from the group consisting of Herpes Simplex virus-1, Herpes Simplex virus-2, Varicella-Zoster virus, Epstein-Barr virus, Cytomegalovirus, Human Herpes virus-6, Variola virus, Vesicular stomatitis virus, Hepatitis A virus, Hepatitis B virus, Hepatitis C virus, Hepatitis D virus, Hepatitis E virus, Rhinovirus, Coronavirus, Influenza virus A, Influenza virus B, Measles virus, Polyomavirus, Human Papillomavirus, Respiratory syncytial virus, Adenovirus, Coxsackie virus, Dengue virus, Mumps virus, Poliovirus, Rabies virus, Rous sarcoma virus, Reovirus, Yellow fever virus, Zika virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Simian Immunodeficiency virus, Human T-cell Leukemia virus type-1, Hantavirus, Rubella virus, Simian Immunodeficiency virus, Human Immunodeficiency virus type-1, and Human Immunodeficiency virus type-2.

Also disclosed herein are methods of treating an inflammatory skin disorder; wherein the inflammatory skin disorder is caused by a bacterial infection, wherein the bacterial infection is an infection with a bacteria selected from the group consisting of *Mycobacterium tuberculosis, Mycobacterium bovis, Mycobacterium bovis* strain BCG, BCG substrains, *Mycobacterium avium, Mycobacterium intracellular, Mycobacterium africanum, Mycobacterium kansasii, Mycobacterium marinum, Mycobacterium ulcerans, Mycobacterium avium* subspecies *paratuberculosis, Nocardia asteroides*, other *Nocardia* species, *Legionella pneumophila*, other *Legionella* species, *Bacillus anthracis, Acetinobacter baumanii, Salmonella typhi, Salmonella enterica*, other *Salmonella* species, *Shigella boydii, Shigella dysenteriae, Shigella sonnei, Shigella flexneri*, other *Shigella* species, *Yersinia pestis, Pasteurella haemolytica, Pasteurella multocida*, other *Pasteurella* species, *Actinobacillus pleuropneumoniae, Listeria monocytogenes, Listeria ivanovii, Brucella abortus*, other *Brucella* species, *Cowdria ruminantium, Borrelia burgdorferi, Bordetella avium, Bordetella pertussis, Bordetella bronchiseptica, Bordetella trematum, Bordetella hinzii, Bordetella pteri, Bordetella parapertussis, Bordetella ansorpii* other *Bordetella* species, *Burkholderia mallei, Burkholderia psuedomallei, Burkholderia cepacian, Chlamydia pneumoniae, Chlamydia trachomatis, Chlamydia psittaci, Coxiella burnetii, Rickettsial* species, *Ehrlichia* species, *Staphylococcus aureus, Staphylococcus epidermidis, Streptococcus pneumoniae, Streptococcus pyogenes, Streptococcus agalactiae, Escherichia coli, Vibrio cholerae, Campylobacter* species, *Neiserria meningitidis, Neiserria gonorrhea, Pseudomonas aeruginosa*, other *Pseudomonas* species, *Haemophilus influenzae, Haemophilus ducreyi*, other *Hemophilus* species, *Clostridium tetani*, other *Clostridium* species, *Yersinia enterolitica*, and other *Yersinia* species. In some instances, the bacteria causing the bacterial infection is not *Bacillus anthracis.*

In one aspect, disclosed herein are methods of treating an inflammatory skin disorder; wherein the inflammatory skin disorder is caused by a fungal infection, wherein the fungal infection is an infection with a fungi selected from the group consisting of *Candida albicans, Cryptococcus neoformans, Histoplasma capsulatum, Aspergillus fumigatus, Coccidioides immitis, Paracoccidioides brasiliensis, Blastomyces dermatidis, Pneumocystis carinii, Penicillium marneffi*, and *Alternaria alternata.*

Also disclosed herein are methods of treating an inflammatory skin disorder; wherein the inflammatory skin disorder is caused by a parasitic infection, wherein the parasitic infection is an infection with a parasite selected from the group consisting of *Toxoplasma gondii, Plasmodium falciparum, Plasmodium vivax, Plasmodium malariae*, other *Plasmodium* species, *Entamoeba histolytica, Naegleria fowleri, Rhinosporidium seeberi, Giardia lamblia, Enterobius vermicularis, Enterobius gregorii, Ascaris lumbricoides, Ancylostoma duodenale, Necator americanus, Cryptosporidium* spp., *Trypanosoma brucei, Trypanosoma cruzi, Leishmania major*, other *Leishmania* species, *Diphyllobothrium latum, Hymenolepis nana, Hymenolepis diminuta, Echinococcus granulosus, Echinococcus multilocularis, Echinococcus vogeli, Echinococcus oligarthrus, Diphyllobothrium latum, Clonorchis sinensis; Clonorchis viverrini, Fasciola hepatica, Fasciola gigantica, Dicrocoelium dendriticum, Fasciolopsis bush, Metagonimus yokogawai, Opisthorchis viverrini, Opisthorchis felineus, Clonorchis sinensis, Trichomonas vaginalis, Acanthamoeba* species, *Schistosoma intercalatum, Schistosoma haematobium, Schistosoma japonicum, Schistosoma mansoni*, other *Schistosoma* species, *Trichobilharzia regenti, Trichinella spiralis, Trichinella britovi, Trichinella nelsoni, Trichinella nativa*, and *Entamoeba histolytica.*

It is understood and herein contemplated that while addressing the inflammatory skin disorder may alleviate symptoms of inflammatory disorder or alleviate the skin disorder caused by the microbial infection, the methods and NTMs disclosed herein will not remove the causative microbe (although such clearance could be driven by a properly regulated host immune response). It is understood and herein contemplated that any method of treating an inflammatory skin disorder comprising administering a composition comprising any of the NTM disclosed herein can further comprise the administration of an anti-microbial agent. Examples of anti-microbial agents include any antibiotics, antibodies, small molecules, and functional nucleic acids (siRNA, RNAi, anti-sense oligonucleotides), that directly attack the infecting microbe or alter host conditions rendering the host system inhospitable to the microbe. Such agents include, but are not limited to Abacavir, Acyclovir, Adefovir, Amantadine, Amprenavir, Ampligen, Arbidol, Atazanavir, Atripla, Balavir, Cidofovir, Combivir, Dolutegravir, Darunavir, Delavirdine, Didanosine, Docosanol, Edoxudine, Efavirenz, Emtricitabine, Enfuvirtide, Entecavir, Ecoliever, Famciclovir, Fomivirsen, Fosamprenavir, Foscarnet, Fosfonet, Ganciclovir, Ibacitabine, Imunovir, Idoxuridine, Imiquimod, Indinavir, Inosine, Lamivudine, Lopinavir, Loviride, Maraviroc, Moroxydine, Methisazone, Nelfinavir, Nevirapine, Nexavir, Nitazoxanide, Norvir, Oseltamivir, Peginterferon alfa-2a, Penciclovir, Peramivir, Pleconaril, Podophyllotoxin, Raltegravir, Ribavirin, Rimantadine, Ritonavir, Pyramidine, Saquinavir, Sofosbuvir, Stavudine, Telaprevir, Tenofovir, Tenofovir disoproxil, Tipranavir, Trifluridine, Trizivir, Tromantadine, Truvada, Valaciclovir, Valganciclovir, Vicriviroc, Vidarabine, Viramidine, Zalcitabine, Zanamivir, Zidovudine, Clofazimine; Dapsone; Capreomycin; Cycloserine; Ethambutol(Bs); Ethionamide; Isoniazid; Pyrazinamide; Rifampicin; Rifabutin; Rifapentine; Streptomycin; Arsphenamine; Chloramphenicol(Bs); Fosfomycin; Fusidic acid; Metronidazole; Mupirocin; Platensimycin; Quinupristin/Dalfopristin; Thiamphenicol; Tigecycline(Bs); Tinidazole; Trimethoprim(Bs); aminoglycosides such as, for example, Amikacin, Gentamicin, Kanamycin, Meropenem, Neomycin, Netilmicin, Tobramycin, Paromomycin, Streptomycin, Spectinomycin, Nitazoxanide, Melarsoprol Eflornithine, Metronidazole, Tinidazole, Miltefosine, Mebendazole, Pyrantel pamoate, Thiabendazole, Diethylcarbamazine, Ivermectin, Niclosamide, Praziquantel, Albendazole, Praziquantel, Rifampin, Amphotericin B, Fumagillin, Amphotericin B, Candicidin, Filipin, Hamycin, Natamycin, Nystatin, Rimocidin, Bifonazole, Butoconazole, Clotrimazole, Econazole, Fenticonazole, Isoconazole, Ketoconazole, Luliconazole, Miconazole, Omoconazole, Oxiconazole, Sertaconazole, Sulconazole, Tioconazole, Albaconazole, Efinaconazole, Epoxiconazole, Fluconazole, Isavuconazole, Itraconazole, Posaconazole, Propiconazole, Ravuconazole, Terconazole, Voriconazole, Abafungin, Anidulafungin, Caspofungin, Micafungin, Aurones, Benzoic acid, Ciclopirox, Flucytosine, Griseofulvin, Haloprogin, Tolnaftate, Undecylenic acid, Crystal violet, Balsam of Peru, Orotomide, Miltefosine, ansamycins, such as, for example, geldanamycin, rifaximin, herbimycin; Carbapenems, such as, for example, Ertapenem, Doripenem, Imipenem/Cilastatin, and Meropenem; Cephalosporins, such as, for example, Cefadroxil, Cefazolin, Cephradine, Cephapirin, Cephalothin, Cefalexin, Cefaclor, Cefoxitin, Cefotetan, Cefamandole, Cefmetazole, Cefonicid, Loracarbef, Cefprozil, Cefuroxime, Cefixime, Cefdinir, Cefditoren, Cefoperazone, Cefotaxime, Cefpodoxime, Ceftazidime, Ceftibuten, Ceftizoxime, Moxalactam, Ceftriaxone, Cefepime, Ceftaroline fosamil, and Ceftobiprole; Glycopeptides, such as, for example Teicoplanin, Vancomycin, Telavancin, Dalbavancin, and Oritavancin; Lincosamides(Bs), such as, for example, Clindamycin and Lincomycin; Lipopeptides, such as, for example, Daptomycin; Macrolides (Bs), such as, for example, Azithromycin, Clarithromycin, Erythromycin, Roxithromycin, Telithromycin, and Spiramycin; Monobactams, such as, for example, Aztreonam; Nitrofurans, such as, for example, Furazolidone and Nitrofurantoin(Bs); Oxazolidinones(Bs), such as, for example, Linezolid, Posizolid, Radezolid, and Torezolid; Penicillins, such as, for example, Amoxicillin, Ampicillin, Azlocillin, Dicloxacillin, Flucloxacillin, Mezlocillin, Methicillin, Nafcillin, Oxacillin, Penicillin G, Penicillin V, Piperacillin, Penicillin G, Temocillin, and Ticarcillin; Polypeptides, such as, for example, Bacitracin, Colistin, and Polymyxin B; Quinolones/Fluoroquinolones, such as, for example, Ciprofloxacin, Enoxacin, Gatifloxacin, Gemifloxacin, Levofloxacin, Lomefloxacin, Moxifloxacin, Nadifloxacin, Nalidixic acid, Norfloxacin, Ofloxacin, Trovafloxacin, Grepafloxacin, Sparfloxacin, and Temafloxacin; Sulfonamides(Bs), such as, for example, Mafenide, Sulfacetamide, Sulfadiazine, Silver sulfadiazine, Sulfadimethoxine, Sulfamethizole, Sulfamethoxazole, Sulfanilimide (archaic), Sulfasalazine, Sulfisoxazole, Trimethoprim-Sulfamethoxazole (Co-trimoxazole) (TMP-SMX), and Sulfonamidochrysoidine (archaic); Tetracyclines(Bs), such as, for example, Demeclocycline, Doxycycline, Metacycline, Minocycline, Oxytetracycline, and Tetracycline; monoclonal antibodies such as, for example, Actoxumab, Atidortoxumab, Berlimatoxumab, Bezlotoxumab, Cosfroviximab, Edobacomab, Felvizumab, Firivumab, Foravirumab, Larcaviximab, Motavizumab, Navivumab, Panobacumab, Palivizumab, Porgaviximab, CR6261, Rafivirumab, Pagibaximab, Obiltoxaximab, Ibalizumab, Regavirumab, Rmab, Sevirumab, Rivabazumab pegol, Tefibazumab, Suvratoxumab, and Tuvirumab; and checkpoint inhibitors; Pembrolizumab, Nivolumab, Atezolizumab, Avelumab, Durvalumab, pidilizumab, AMP-224, AMP-514, PDR001, cemiplimab, and Ipilimumab.

In one aspect, it is understood and herein contemplated that the inflammatory skin disorder treated using the methods and NTMs disclosed herein can be caused by an autoimmune disease. Autoimmune diseases are set of diseases, disorders, or conditions resulting from an adaptive immune response (T cell and/or B cell response) against the host organism. In such conditions, either by way of mutation or other underlying cause, the host T cells and/or B cells and/or antibodies are no longer able to distinguish host cells from non-self-antigens and attack host cells bearing an antigen for which they are specific. Examples of autoimmune diseases that can cause an inflammatory skin disorder include, but are not limited to Achalasia, Acute disseminated encephalomyelitis, Acute motor axonal neuropathy, Addison's disease, Adiposis dolorosa, Adult Still's disease, Agammaglobulinemia, Alopecia areata, Alzheimer's disease, Amyloidosis, Ankylosing spondylitis, Anti-GBM/Anti-TBM nephritis, Antiphospholipid syndrome, Aplastic anemia, Autoimmune angioedema, Autoimmune dysautonomia, Autoimmune encephalomyelitis, Autoimmune enteropathy, Autoimmune hemolytic anemia, Autoimmune hepatitis, Autoimmune inner ear disease (AIED), Autoimmune myocarditis, Autoimmune oophoritis, Autoimmune orchitis, Autoimmune pancreatitis, Autoimmune polyendocrine syndrome, Autoimmune retinopathy, Autoimmune urticaria, Axonal & neuronal neuropathy (AMAN), Baló disease, Behcet's disease, Benign mucosal pemphigoid, Bickerstaff's encephalitis, Bullous pemphigoid, Castleman disease (CD), Celiac disease, Chagas disease, Chronic fatigue syndrome, Chronic inflammatory demyelinating polyneuropathy (CIDP), Chronic recurrent multifocal osteomyelitis (CRMO), Churg-Strauss Syndrome (CSS), Eosinophilic Granulomatosis (EGPA), Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Diabetes mellitus type 1, Discoid lupus, Dressler's syndrome, Endometriosis, Enthesitis, Eosinophilic esophagitis (EoE), Eosinophilic fasciitis, Erythema nodosum, Essential mixed cryoglobulinemia, Evans syndrome, Felty syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis, Graves' disease, Guillain-Barre syndrome, Hashimoto's encephalopathy, Hashimoto's thyroiditis, Hemolytic anemia, Henoch-Schonlein purpura (HSP), Herpes gestationis or pemphigoid gestationis (PG), Hidradenitis Suppurativa (HS) (Acne Inversa), Hypogammalglobulinemia, IgA Nephropathy, IgG4-related sclerosing disease, Immune thrombocytopenic purpura (ITP), Inclusion body myositis (IBM), Interstitial cystitis (IC), Inflamatory Bowel Disease (IBD), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus nephritis, Lupus vasculitis, Lyme disease chronic, Meniere's disease, Microscopic polyangiitis (MPA), Mixed connective tissue disease (MCTD), Mooren's ulcer, Mucha-Habermann disease, Multifocal Motor Neuropathy (MMN) or MMNCB, Multiple sclerosis, Myasthenia gravis, Myositis, Narcolepsy, Neonatal Lupus, Neuromyelitis optica, Neutropenia, Ocular cicatricial pemphigoid, Optic neuritis, Ord's thyroiditis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonnage-Turner syndrome, Pemphigus, Peripheral neuropathy, Perivenous encephalomyelitis, Pernicious anemia (PA), POEMS syndrome, Polyarteritis nodosa, Polyglandular syndromes type I, II, III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Rheumatoid vasculitis, Sarcoidosis, Schmidt syndrome, Schnitzler syndrome, Scleritis, Scleroderma, Sjögren's syndrome, Sperm & testicular autoimmunity, Stiff person syndrome (SPS), Subacute bacterial endocarditis (SBE), Susac's syndrome, Sydenham chorea, Sympathetic ophthalmia (SO), Systemic Lupus Erythematosus, Systemic scleroderma, Takayasu's arteritis, Temporal arteritis/Giant cell arteritis, Thrombocytopenic purpura (TTP), Tolosa-Hunt syndrome (THS), Transverse myelitis, Type 1 diabetes, Ulcerative colitis (UC), Undifferentiated connective tissue disease (UCTD), Urticaria, Urticarial vasculitis, Uveitis, Vasculitis, Vitiligo, Vogt-Koyanagi-Harada Disease, and Wegener's granulomatosis (or Granulomatosis with Polyangiitis (GPA)).

It is understood that not all inflammatory skin disorders resulting from attack by the host immune system involve the adaptive immune response. In some instances, the innate immune response (i.e., NK cells, macrophage) attack the host cells. Diseases where the host innate immune response attacks host cells is referred to as an "autoinflammatory disease." In one aspect, disclosed herein are methods of treating an inflammatory skin disorder in a subject comprising administering to the subject a therapeutically effective amount of a composition comprising a Nuclear Transport Modifier (NTM); wherein the inflammatory skin disorder is caused by an autoinflammatory disorder. Examples of autoinflammatory, autoimmune, and allergic disorders that can cause the inflammatory skin diseases treated by the disclosed methods include, but are not limited to asthma, graft versus host disease, allergy, transplant rejection, Familial Cold Autoinflammatory Syndrome (FCAS), Muckle-Wells Syndrome (MWS), Neonatal-Onset Multisystem Inflammatory Disease (NOMID) (also known as Chronic Infantile Neurological Cutaneous Articular Syndrome (CINCA)), Familial Mediterranean Fever (FMF), Tumor Necrosis Factor (TNF)—Associated Periodic Syndrome (TRAPS), TNFRSF11A-associated hereditary fever disease (TRAPS11), Hyperimmunoglobulinemia D with Periodic Fever Syndrome (HIDS), Mevalonate Aciduria (MA), Mevalonate Kinase Deficiencies (MKD), Deficiency of Interleukin-1β (IL-1β) Receptor Antagonist (DIRA) (also known as Osteomyelitis, Sterile Multifocal with Periostitis Pustulosis), Majeed Syndrome, Chronic Nonbacterial Osteomyelitis (CNO), Early-Onset Inflammatory Bowel Disease, Diverticulitis, Deficiency of Interleukin-36-Receptor Antagonist (DITRA), Familial Psoriasis, Pustular Psoriasis, Pyogenic Sterile Arthritis, Pyoderma Gangrenosum, and Acne Syndrome (PAPA), Congenital sideroblastic anemia with immunodeficiency, fever, and developmental delay (SIFD), Pediatric Granulomatous Arthritis (PGA), Familial Behçets-like Autoinflammatory Syndrome, NLRP12-Associated Periodic Fever Syndrome, Proteasome-associated Autoinflammatory Syndromes (PRAAS), Spondyloenchondrodysplasia with immune dysregulation (SPENCDI), STING-associated vasculopathy with onset in infancy (SAVI), Aicardi-Goutieres syndrome, Acute Febrile Neutrophilic Dermatosis, X-linked familial hemophagocytic lymphohistiocytosis, and Lyn kinase-associated Autoinflammatory Disease (LAID).

In one aspect, it is understood and herein contemplated that metabolic disorders can underly the inflammation that results in an inflammatory skin disorder or inflammatory signs of the disorder. Accordingly, disclosed herein are methods of treating an inflammatory skin disorder, wherein the inflammatory skin disorder is caused by a metabolic disorder. In one aspect, the metabolic disorder can be selected from the group consisting of metabolic syndrome, diabetes mellitus, obesity, Gaucher's disease, Phenylketonuria (PKU), Maple syrup urine disease (MSUD), fatty liver, hypercholesterolemia, hypertriglyceridemia, hyperthyroidism, hypothyroidism, dyslipidemia, hypolipidemia, galactosemia, an seborrhoic acne.

It is understood and herein contemplated that inflammation and, in particular, inflammatory skin disorders can be caused by uncontrolled proliferation (i.e., neoplastic disorders and cancers). Thus, for example, disclosed herein are methods of treating inflammatory skin disorder comprising administering to a subject with an inflammatory skin disorder a therapeutically effective amount of a composition comprising an NTM, wherein the inflammatory skin disorder is caused by uncontrolled proliferation (such as, for example, a neoplastic disorder or cancer such as proliferative T-cell disorders). In one aspect, disclosed herein are methods of treating an inflammatory skin disorder associated with a neoplastic disorder or a cancer, wherein the neoplastic disorder or cancer is selected from the group consisting of lymphoma, PTEN hamartoma syndrome, Familial adenomatous polyposis, Tuberous sclerosis complex, Von Hippel-Lindau disease, ovarian teratomas, meningiomas, osteochondromas, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, lung cancers such as small cell lung cancer and non-small cell lung cancer, neuroblastoma/glioblastoma, ovarian cancer, skin cancer, liver cancer, melanoma, squamous cell carcinomas of the mouth, throat, larynx, and lung, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon cancer, rectal cancer, prostatic cancer, and pancreatic cancer.

It is well established that physical insult through abrasion, puncture, laceration, contusion, blunt force trauma, ischemia, hemorrhagic stroke, surgery, transplant, sunburn, chemical burn, high temperature burn, low temperature burn, and post-radiation burn can produce an inflammatory response. Some of these responses can either result in inflammation that manifests on the skin or an inflammatory skin disorder. Accordingly, disclosed herein are methods of treating an inflammatory skin disorder comprising administering to a subject with an inflammatory skin disorder a therapeutically effective amount of a composition comprising an NTM, wherein the inflammatory skin disorder is caused by physical injury. In one aspect, the physical injury can be selected from the group consisting of abrasion, puncture, laceration, contusion, blunt force trauma, ischemia, hemorrhagic stroke, surgery, transplant, sunburn, chemical burn, high temperature burn, low temperature burn.

The methods disclosed herein involve treating inflammatory skin disorders or symptoms from other inflammatory insults on the skin. It is understood and herein contemplated that many inflammatory conditions treatments will involve the treatment of a wound. Thus, in one aspect, disclosed herein are methods of treating a wound comprising contacting the wound with a therapeutically effective amount of a composition comprising a Nuclear Transport Modifier (NTM) such as, for example, an NTM that comprises the sequence set forth in SEQ ID NO: 1, SEQ ID NO: 2, SEQ ID NO: 3; SEQ ID NO: 4; SEQ ID NO: 5; SEQ ID NO: 6, SEQ ID NO: 7, SEQ ID NO: 8, SEQ ID NO: 9, SEQ ID NO: 11, SEQ ID NO: 13, SEQ ID NO: 16, SEQ ID NO: 17, SEQ ID NO: 18, SEQ ID NO: 19; SEQ ID NO: 20; SEQ ID NO: 21; SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29; SEQ ID NO: 30; SEQ ID NO: 31; SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39; SEQ ID NO: 40; and/or SEQ ID NO: 41. It is further understood, that by treating a wound with a therapeutically effective amount of a composition comprising a Nuclear Transport Modifier (NTM) not only will the wound be treated, but the time needed for the healing process can be reduced compared to untreated wounds. Thus, disclosed herein are methods of reducing the healing time of a wound comprising contacting the wound with a therapeutically effective amount of a composition comprising a Nuclear Transport Modifier (NTM) such as, for example, an NTM that comprises the sequence set forth in SEQ ID NO: 1, SEQ ID NO: 2, SEQ ID NO: 3; SEQ ID NO: 4; SEQ ID NO: 5; SEQ ID NO: 6, SEQ ID NO: 7, SEQ ID NO: 8, SEQ ID NO: 9, SEQ ID NO: 11, SEQ ID NO: 13, SEQ ID NO: 16, SEQ ID NO: 17, SEQ ID NO: 18, SEQ ID NO: 19; SEQ ID NO: 20; SEQ ID NO: 21; SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29; SEQ ID NO: 30; SEQ ID NO: 31; SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39; SEQ ID NO: 40; and/or SEQ ID NO: 41.

In one aspect, it is understood and herein contemplated that one way to treat a wound is through administration of the NTM subcutaneously, intramuscularly, intravenously, topically (such as, for example, through the use of salves, creams, and/or ointments), but also by impregnating bandages, dressing, sutures, drapes, surgical adhesive, and/or staples with the NTM. Thus, in one aspect, disclosed herein are medicated adhesive bandages, wound dressings, surgical drapes, sutures, salves, creams, or wound adhesives comprising a therapeutically effective amount of a composition comprising a Nuclear Transport Modifier (NTM) such as, for example, an NTM that comprises the sequence set forth in SEQ ID NO: 1, SEQ ID NO: 2, SEQ ID NO: 3; SEQ ID NO: 4; SEQ ID NO: 5; SEQ ID NO: 6, SEQ ID NO: 7, SEQ ID NO: 8, SEQ ID NO: 9, SEQ ID NO: 11, SEQ ID NO: 13, SEQ ID NO: 16, SEQ ID NO: 17, SEQ ID NO: 18, SEQ ID NO: 19; SEQ ID NO: 20; SEQ ID NO: 21; SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29; SEQ ID NO: 30; SEQ ID NO: 31; SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39; SEQ ID NO: 40; and/or SEQ ID NO: 41. It is understood and herein contemplated that the medicated adhesive bandages, wound dressings, surgical drapes, staples, sutures, salves, creams, or wound adhesives disclosed herein can be used in conjunction with any of the disclosed methods of treatment. Thus, in one aspect, disclosed herein are methods of treating/inhibiting/reducing an inflammatory skin disorder (including, but not limited to inflammatory skin disorders caused by microbial disease, autoimmune disease, autoinflammatory disorder, metabolic disorder, neoplastic disorder, and/or physical insults that are mediated by inflammation), treating a wound, and/or reducing the healing time of a wound comprising administering to a subject with a skin disorder and/or wound the medicated adhesive bandages, wound dressings, surgical drapes, staples, sutures, salves, creams, or wound adhesives disclosed herein.

4. Methods of Treating Autoimmune Diseases

As noted above, the NTMs disclosed herein can target the nuclear transport shuttles, Imp α5 and Imp β1, that translocate SRTFs to the nucleus and control signal transduction pathways, which culminate in genomic reprogramming Thus, the novel forms of immunotherapy disclosed herein that targets nuclear import as described herein can arrest inflammation-driven destruction associated with diseases including autoimmune diseases. As used herein, "autoimmune disease" refers to a set of diseases, disorders, or conditions resulting from an adaptive immune response (T cell and/or B cell response) against the host organism. In such conditions, either by way of mutation or other underlying cause, the host T cells and/or B cells and/or antibodies are no longer able to distinguish host cells from non-self-antigens and attack host cells bearing an antigen for which they are specific. Examples of autoimmune diseases include, but are not limited to graft versus host disease, transplant rejection, Achalasia, Acute disseminated encephalomyelitis, Acute motor axonal neuropathy, Addison's disease, Adiposis dolorosa, Adult Still's disease, Agammaglobulinemia, Alopecia areata, Alzheimer's disease, Amyloidosis, Ankylosing spondylitis, Anti-GBM/Anti-TBM nephritis, Antiphospholipid syndrome, Aplastic anemia, Autoimmune angioedema, Autoimmune dysautonomia, Autoimmune encephalomyelitis, Autoimmune enteropathy, Autoimmune hemolytic anemia, Autoimmune hepatitis, Autoimmune inner ear disease (AIED), Autoimmune myocarditis, Autoimmune oophoritis, Autoimmune orchitis, Autoimmune pancreatitis, Autoimmune polyendocrine syndrome, Autoimmune retinopathy, Autoimmune urticaria, Axonal & neuronal neuropathy (AMAN), Baló disease, Behcet's disease, Benign mucosal pemphigoid, Bickerstaff's encephalitis, Bullous pemphigoid, Castleman disease (CD), Celiac disease, Chagas disease, Chronic fatigue syndrome, Chronic inflammatory demyelinating polyneuropathy (CIDP), Chronic recurrent multifocal osteomyelitis (CRMO), Churg-Strauss Syndrome (CSS), Eosinophilic Granulomatosis (EGPA), Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Diabetes mellitus type 1, Discoid lupus, Dressler's syndrome, Endometriosis, Enthesitis, Eosinophilic esophagitis (EoE), Eosinophilic fasciitis, Erythema nodosum, Essential mixed cryoglobulinemia, Evans syndrome, Felty syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis, Graves' disease, Guillain-Barre syndrome, Hashimoto's encephalopathy, Hashimoto's thyroiditis, Hemolytic anemia, Henoch-Schonlein purpura (HSP), Herpes gestationis or pemphigoid gestationis (PG), Hidradenitis Suppurativa (HS) (Acne Inversa), Hypogammalglobulinemia, IgA Nephropathy, IgG4-related sclerosing disease, Immune thrombocytopenic purpura (ITP), Inclusion body myositis (IBM), Interstitial cystitis (IC), Inflamatory Bowel Disease (IBD), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus nephritis, Lupus vasculitis, Lyme disease chronic, Meniere's disease, Microscopic polyangiitis (MPA), Mixed connective tissue disease (MCTD), Mooren's ulcer, Mucha-Habermann disease, Multifocal Motor Neuropathy (MMN) or MMNCB, Multiple sclerosis, Myasthenia gravis, Myositis, Narcolepsy, Neonatal Lupus, Neuromyelitis optica, Neutropenia, Ocular cicatricial pemphigoid, Optic neuritis, Ord's thyroiditis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonnage-Turner syndrome, Pemphigus, Peripheral neuropathy, Perivenous encephalomyelitis, Pernicious anemia (PA), POEMS syndrome, Polyarteritis nodosa, Polyglandular syndromes type I, II, III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Rheumatoid vasculitis, Sarcoidosis, Schmidt syndrome, Schnitzler syndrome, Scleritis, Scleroderma, Sjögren's syndrome, Sperm & testicular autoimmunity, Stiff person syndrome (SPS), Susac's syndrome, Sydenham chorea, Sympathetic ophthalmia (SO), Systemic Lupus Erythematosus, Systemic scleroderma, Takayasu's arteritis, Temporal arteritis/Giant cell arteritis, Thrombocytopenic purpura (TTP), Tolosa-Hunt syndrome (THS), Transverse myelitis, Type 1 diabetes, Ulcerative colitis (UC), Undifferentiated connective tissue disease (UCTD), Urticaria, Urticarial vasculitis, Uveitis, Vasculitis, Vitiligo, Vogt-Koyanagi-Harada Disease, and Wegener's granulomatosis (or Granulomatosis with Polyangiitis (GPA)). In one aspect, disclosed herein are methods of treating autoimmune diseases or inflammatory symptoms associated with an autoimmune disease administering to a subject with an autoimmune disease comprising administering to the subject a therapeutically effective amount of a composition comprising a Nuclear Transport Modifier (NTM) such as, for example, an NTM that comprises the sequence set forth in SEQ ID NO: 1, SEQ ID NO: 2, SEQ ID NO: 3; SEQ ID NO: 4; SEQ ID NO: 5; SEQ ID NO: 6, SEQ ID NO: 7, SEQ ID NO: 8, SEQ ID NO: 9, SEQ ID NO: 11, SEQ ID NO: 13, SEQ ID NO: 16, SEQ ID NO: 17, SEQ ID NO: 18, SEQ ID NO: 19; SEQ ID NO: 20; SEQ ID NO: 21; SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29; SEQ ID NO: 30; SEQ ID NO: 31; SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39; SEQ ID NO: 40; and/or SEQ ID NO: 41.

5. Methods of Treating Autoinflammatory Diseases

The compositions comprising NTM disclosed herein (such as, for example, NTM that comprises the sequence set forth in SEQ ID NO: 1, SEQ ID NO: 2, SEQ ID NO: 3; SEQ ID NO: 4; SEQ ID NO: 5; SEQ ID NO: 6, SEQ ID NO: 7, SEQ ID NO: 8, SEQ ID NO: 9, SEQ ID NO: 11, SEQ ID NO: 13, SEQ ID NO: 16, SEQ ID NO: 17, SEQ ID NO: 18, SEQ ID NO: 19; SEQ ID NO: 20; SEQ ID NO: 21; SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29; SEQ ID NO: 30; SEQ ID NO: 31; SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39; SEQ ID NO: 40; and/or SEQ ID NO: 41) are not limited in treatment of inflammation resulting from adaptive immune responses, but are also effective in arresting inflammation-driven destruction associated with the inborn errors of innate immune responses (i.e. Constitutive inflammation that underlies autoinflammatory diseases). As used herein "autoinflammatory diseases refer to disorders where the innate immune response attacks host cells. Examples of autoinflammatory disorders include, Familial Cold Autoinflammatory Syndrome (FCAS), Muckle-Wells Syndrome (MWS), Neonatal-Onset Multisystem Inflammatory Disease (NOMID) (also known as Chronic Infantile Neurological Cutaneous Articular Syndrome (CINCA)), Familial Mediterranean Fever (FMF) and other cryopyrin-associated periodic syndromes (CAPS), Tumor Necrosis Factor (TNF)—Associated Periodic Syndrome (TRAPS), TNFRSF11A-associated hereditary fever disease (TRAPS11), Hyperimmunoglobulinemia D with Periodic Fever Syndrome (HIDS), Mevalonate Aciduria (MA), Mevalonate Kinase Deficiencies (MKD), Deficiency of Interleukin-1β (IL-1β) Receptor Antagonist (DIRA) (also known as Osteomyelitis, Sterile Multifocal with Periostitis Pustulosis), Majeed Syndrome, Chronic Nonbacterial Osteomyelitis (CNO), Early-Onset Inflammatory Bowel Disease, Diverticulitis, Deficiency of Interleukin-36-Receptor Antagonist (DITRA), Familial Psoriasis (PSORS2), Pustular Psoriasis (15), Pyogenic Sterile Arthritis, Pyoderma Gangrenosum, and Acne Syndrome (PAPA), Congenital sideroblastic anemia with immunodeficiency, fevers, and developmental delay (SIFD), Pediatric Granulomatous Arthritis (PGA), Familial Behçets-like Autoinflammatory Syndrome, NLRP12-Associated Periodic Fever Syndrome, Proteasome-associated Autoinflammatory Syndromes (PRAAS), Spondyloenchondrodysplasia with immune dysregulation (SPENCDI), STING-associated vasculopathy with onset in infancy (SAVI), Aicardi-Goutieres syndrome and other Type 1 Interferonopathies, Acute Febrile Neutrophilic Dermatosis, X-linked familial hemophagocytic lymphohistiocytosis, Lyn kinase-associated Autoinflammatory Disease (LAID), and intestinal and skin inflammatory disorders caused by deletion mutation of the carboxy-terminal segment of the NF-κB essential modulator (NEMO). In one aspect, disclosed herein are methods of treating an autoinflammatory disorder or inflammatory symptoms associated with an autoinflammatory disorder comprising administering to a subject with an autoinflammatory disease comprising administering to the subject a therapeutically effective amount of a composition comprising a Nuclear Transport Modifier (NTM) such as, for example, an NTM that comprises the sequence set forth in SEQ ID NO: 1, SEQ ID NO: 2, SEQ ID NO: 3; SEQ ID NO: 4; SEQ ID NO: 5; SEQ ID NO: 6, SEQ ID NO: 7, SEQ ID NO: 8, SEQ ID NO: 9, SEQ ID NO: 11, SEQ ID NO: 13, SEQ ID NO: 16, SEQ ID NO: 17, SEQ ID NO: 18, SEQ ID NO: 19; SEQ ID NO: 20; SEQ ID NO: 21; SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29; SEQ ID NO: 30; SEQ ID NO: 31; SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39; SEQ ID NO: 40; and/or SEQ ID NO: 41.

6. Methods of Treating a Metabolic Disorder

As noted throughout this specification, NTMs target the nuclear transport shuttles, Imp α5 and Imp β1, that translocate SRTFs, ChREBPs, and SREBPs to the nucleus and control signal transduction pathways, which culminate in genomic reprogramming. The novel forms of immunotherapy that targets nuclear import as described herein can arrest inflammation-driven organ injury, including damage resulting from metabolic disorders, such as, for example, metabolic syndrome that encompasses fatty liver, hypercholesterolemia, hypertriglyceridemia, diabetes mellitus, and obesity. Furthermore, Gaucher's disease, Phenylketonuria (PKU), Maple syrup urine disease (MSUD), hyperuricemia (gout), calcium pyrophosphate deposition disease (pseudogout), hyperthyroidism, hypothyroidism, dyslipidemia, hypolipidemia, and galactosemia). Thus in one aspect, disclosed herein are methods of treating metabolic disease or metabolic disease mediated by inflammation comprising administering to a subject with an autoimmune disease comprising administering to the subject a therapeutically effective amount of a composition comprising a NTM (such as, for example, an NTM that comprises the sequence set forth in SEQ ID NO: 1, SEQ ID NO: 2, SEQ ID NO: 3; SEQ ID NO: 4; SEQ ID NO: 5; SEQ ID NO: 6, SEQ ID NO: 7, SEQ ID NO: 8, SEQ ID NO: 9, SEQ ID NO: 11, SEQ ID NO: 13, SEQ ID NO: 16, SEQ ID NO: 17, SEQ ID NO: 18, SEQ ID NO: 19; SEQ ID NO: 20; SEQ ID NO: 21; SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29; SEQ ID NO: 30; SEQ ID NO: 31; SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39; SEQ ID NO: 40; and/or SEQ ID NO: 41).

7. Methods of Treating Neoplastic Disorders

In one aspect, it is understood and herein contemplated that the immune response to any disease where uncontrolled cellular proliferation occurs such as metaplasia, dysplasia, cancers (i e, malignant neoplasms) and benign neoplastic disorder can evolve from chronic inflammation and result in a significant organ injury mediated by inflammation. Many types of cancer evolve from chronic inflammation that leads to cancer in chronic viral hepatitis, papilloma viruses-caused precancerous lesions of the cervix, Helicobacter pylori-induced stomach cancer and HTLV-1 associated T-cell leukemia/lymphoma. As noted above, the NTMs disclosed herein can target the nuclear transport shuttles, Imp α5 and Imp β1, that translocate SRTFs, ChREBPs, and SREBPs to the nucleus and control signal transduction pathways, which culminate in genomic reprogramming Thus, the novel forms of immunotherapy disclosed herein that targets nuclear import as described herein can arrest inflammation-driven carcinogenesis associated with these conditions. Thus, in one aspect disclosed herein are methods of treating an uncontrolled cellular proliferation including neoplastic conditions or cancers in a subject comprising administering to the subject a therapeutically effective amount of a composition comprising an NTM. As used herein more examples of neoplastic disorders and cancers that can be treated using the disclosed methods include but are not limited to lymphoma, PTEN hamartoma syndrome, Familial adenomatous polyposis, Tuberous sclerosis complex, Von Hippel-Lindau disease, ovarian teratomas, ovarian clear cell carcinoma, meningiomas, osteochondromas, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, lung cancers such as small cell lung cancer and non-small cell lung cancer, neuroblastoma/glioblastoma, ovarian cancer, skin cancer, liver cancer, melanoma, squamous cell carcinomas of the mouth, throat, larynx, and lung, cervical cancer, breast cancer, and epithelial cancer, renal cancer, genitourinary cancer, lung cancer, esophageal carcinoma, head and neck carcinoma, large bowel cancer, hematopoietic cancers; testicular cancer; colon cancer, rectal cancer, prostatic cancer, and pancreatic cancer. Accordingly, disclosed herein are methods of treating chronic inflammation caused by microbial and chemical carcinogens causing uncontrolled cellular proliferation (such as, for example, metaplasia, dysplasia, cancers and benign neoplastic disorders) comprising administering to a subject with uncontrolled cellular proliferation a therapeutically effective amount of a NTM (such as, for example, an NTM that comprises the sequence set forth in SEQ ID NO: 1, SEQ ID NO: 2, SEQ ID NO: 3; SEQ ID NO: 4; SEQ ID NO: 5; SEQ ID NO: 6, SEQ ID NO: 7, SEQ ID NO: 8, SEQ ID NO: 9, SEQ ID NO: 11, SEQ ID NO: 13, SEQ ID NO: 16, SEQ ID NO: 17, SEQ ID NO: 18, SEQ ID NO: 19; SEQ ID NO: 20; SEQ ID NO: 21; SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29; SEQ ID NO: 30; SEQ ID NO: 31; SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39; SEQ ID NO: 40; and/or SEQ ID NO: 41).

It is understood and herein contemplated that in the treatment of neoplastic disorders or cancers comprising the administration of any NTM composition disclosed herein can further comprise the administration of any chimeric antigen receptor (CAR) T cell, CAR NK cell, tumor infiltrating lymphocyte (TIL), immune checkpoint inhibitor or anti-cancer agent known in the art. Examples of immune checkpoint inhibitor include, but are not limited to PD-1 inhibitors, PD-L1 inhibitors, or CTLA-4 inhibitors (such as, for example, nivolumab, pembrolizumab, pidilizumab, BMS-936559, Atezolizumab, Durvalumab, or Avelumab). Anti-cancer agent for use in the disclosed methods include any anti-cancer agent known in the art, the including, but not limited to Abemaciclib, Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Afatinib Dimaleate, Afinitor (Everolimus), Akynzeo (Netupitant and Palonosetron Hydrochloride), Aldara (Imiquimod), Aldesleukin, Alecensa (Alectinib), Alectinib, Alemtuzumab, Alimta (Pemetrexed Disodium), Aliqopa (Copanlisib Hydrochloride), Alkeran for Injection (Melphalan Hydrochloride), Alkeran Tablets (Melphalan), Aloxi (Palonosetron Hydrochloride), Alunbrig (Brigatinib), Ambochlorin (Chlorambucil), Amboclorin Chlorambucil), Amifostine, Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase Erwinia chrysanthemi, Atezolizumab, Avastin (Bevacizumab), Avelumab, Axitinib, Azacitidine, Bavencio (Avelumab), BEACOPP, Becenum (Carmustine), Beleodaq (Belinostat), Belinostat, Bendamustine Hydrochloride, BEP, Besponsa (Inotuzumab Ozogamicin), Bevacizumab, Bexarotene, Bexxar (Tositumomab and Iodine I 131 Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Brigatinib, BuMel, Busulfan, Busulfex (Busulfan), Cabazitaxel, Cabometyx (Cabozantinib-S-Malate), Cabozantinib-S-Malate, CAF, Campath (Alemtuzumab), Camptosar, (Irinotecan Hydrochloride), Capecitabine, CAPDX, Carac (Fluorouracil-Topical), Carboplatin, CARBOPLATIN-TAXOL, Carfilzomib, Carmubris (Carmustine), Carmustine, Carmustine Implant, Casodex (Bicalutamide), CEM, Ceritinib, Cerubidine (Daunorubicin Hydrochloride), Cervarix (Recombinant HPV Bivalent Vaccine), Cetuximab, CEV, Chlorambucil, CHLORAMBUCIL-PREDNISONE, CHOP, Cisplatin, Cladribine, Clafen (Cyclophosphamide), Clofarabine, Clofarex (Clofarabine), Clolar (Clofarabine), CMF, Cobimetinib, Cometriq (Cabozantinib-S-Malate), Copanlisib Hydrochloride, COPDAC, COPP, COPP-ABV, Cosmegen (Dactinomycin), Cotellic (Cobimetinib), Crizotinib, CVP, Cyclophosphamide, Cyfos (Ifosfamide), Cyramza (Ramucirumab), Cytarabine, Cytarabine Liposome, Cytosar-U (Cytarabine), Cytoxan (Cyclophosphamide), Dabrafenib, Dacarbazine, Dacogen (Decitabine), Dactinomycin, Daratumumab, Darzalex (Daratumumab), Dasatinib, Daunorubicin Hydrochloride, Daunorubicin Hydrochloride and Cytarabine Liposome, Decitabine, Defibrotide Sodium, Defitelio (Defibrotide Sodium), Degarelix, Denileukin Diftitox, Denosumab, DepoCyt (Cytarabine Liposome), Dexamethasone, Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Durvalumab, Efudex (Fluorouracil-Topical), Elitek (Rasburicase), Ellence (Epirubicin Hydrochloride), Elotuzumab, Eloxatin (Oxaliplatin), Eltrombopag Olamine, Emend (Aprepitant), Empliciti (Elotuzumab), Enasidenib Mesylate, Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase Erwinia chrysanthemi), Ethyol (Amifostine), Etopophos (Etoposide Phosphate), Etoposide, Etoposide Phosphate, Evacet (Doxorubicin Hydrochloride Liposome), Everolimus, Evista, (Raloxifene Hydrochloride), Evomela (Melphalan Hydrochloride), Exemestane, 5-FU (Fluorouracil Injection), 5-FU (Fluorouracil-Topical), Fareston (Toremifene), Farydak (Panobinostat), Faslodex (Fulvestrant), FEC, Femara (Letrozole), Filgrastim, Fludara (Fludarabine Phosphate), Fludarabine Phosphate, Fluoroplex (Fluorouracil-Topical), Fluorouracil Injection, Fluorouracil-Topical, Flutamide, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Hemangeol (Propranolol Hydrochloride), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hydrea (Hydroxyurea), Hydroxyurea, Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Idhifa (Enasidenib Mesylate), Ifex (Ifosfamide), Ifosfamide, Ifosfamidum (Ifosfamide), IL-2 (Aldesleukin), Imatinib Mesylate, Imbruvica (Ibrutinib), Imfinzi (Durvalumab), Imiquimod, Imlygic (Talimogene Laherparepvec), Inlyta (Axitinib), Inotuzumab Ozogamicin, Interferon Alfa-2b, Recombinant, Interleukin-2 (Aldesleukin), Intron A (Recombinant Interferon Alfa-2b), Iodine I 131 Tositumomab and Tositumomab, Ipilimumab, Iressa (Gefitinib), Irinotecan Hydrochloride, Irinotecan Hydrochloride Liposome, Istodax (Romidepsin), Ixabepilone, Ixazomib Citrate, Ixempra (Ixabepilone), Jakafi (Ruxolitinib Phosphate), JEB, Jevtana (Cabazitaxel), Kadcyla (Ado-Trastuzumab Emtansine), Keoxifene (Raloxifene Hydrochloride), Kepivance (Palifermin), Keytruda (Pembrolizumab), Kisqali (Ribociclib), Kymriah (Tisagenlecleucel), Kyprolis (Carfilzomib), Lanreotide Acetate, Lapatinib Ditosylate, Lartruvo (Olaratumab), Lenalidomide, Lenvatinib Mesylate, Lenvima (Lenvatinib Mesylate), Letrozole, Leucovorin Calcium, Leukeran (Chlorambucil), Leuprolide Acetate, Leustatin (Cladribine), Levulan (Aminolevulinic Acid), Linfolizin (Chlorambucil), LipoDox (Doxorubicin Hydrochloride Liposome), Lomustine, Lonsurf (Trifluridine and Tipiracil Hydrochloride), Lupron (Leuprolide Acetate), Lupron Depot (Leuprolide Acetate), Lupron Depot-Ped (Leuprolide Acetate), Lynparza (Olaparib), Marqibo (Vincristine Sulfate Liposome), Matulane (Procarbazine Hydrochloride), Mechlorethamine Hydrochloride, Megestrol Acetate, Mekinist (Trametinib), Melphalan, Melphalan Hydrochloride, Mercaptopurine, Mesna, Mesnex (Mesna), Methazolastone (Temozolomide), Methotrexate, Methotrexate LPF (Methotrexate), Methylnaltrexone Bromide, Mexate (Methotrexate), Mexate-AQ (Methotrexate), Midostaurin, Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Necitumumab, Nelarabine, Neosar (Cyclophosphamide), Neratinib Maleate, Nerlynx (Neratinib Maleate), Netupitant and Palonosetron Hydrochloride, Neulasta (Pegfilgrastim), Neupogen (Filgrastim), Nexavar (Sorafenib Tosylate), Nilandron (Nilutamide), Nilotinib, Nilutamide, Ninlaro (Ixazomib Citrate), Niraparib Tosylate Monohydrate, Nivolumab, Nolvadex (Tamoxifen Citrate), Nplate (Romiplostim), Obinutuzumab, Odomzo (Sonidegib), OEPA, Ofatumumab, OFF, Olaparib, Olaratumab, Omacetaxine Mepesuccinate, Oncaspar (Pegaspargase), Ondansetron Hydrochloride, Onivyde (Irinotecan Hydrochloride Liposome), Ontak (Denileukin Diftitox), Opdivo (Nivolumab), OPPA, Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Paraplat (Carboplatin), Paraplatin (Carboplatin), Pazopanib Hydrochloride, PCV, PEB, Pegaspargase, Pegfilgrastim, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Portrazza (Necitumumab), Pralatrexate, Prednisone, Procarbazine Hydrochloride, Proleukin (Aldesleukin), Prolia (Denosumab), Promacta (Eltrombopag Olamine), Propranolol Hydrochloride, Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, Relistor (Methylnaltrexone Bromide), R-EPOCH, Revlimid (Lenalidomide), Rheumatrex (Methotrexate), Ribociclib, R-ICE, Rituxan (Rituximab), Rituxan Hycela (Rituximab and Hyaluronidase Human), Rituximab, Rituximab and, Hyaluronidase Human, Rolapitant Hydrochloride, Romidepsin, Romiplostim, Rubidomycin (Daunorubicin Hydrochloride), Rubraca (Rucaparib Camsylate), Rucaparib Camsylate, Ruxolitinib Phosphate, Rydapt (Midostaurin), Sclerosol Intrapleural Aerosol (Talc), Siltuximab, Sipuleucel-T, Somatuline Depot (Lanreotide Acetate), Sonidegib, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synribo (Omacetaxine Mepesuccinate), Tabloid (Thioguanine), TAC, Tafinlar (Dabrafenib), Tagrisso (Osimertinib), Talc, Talimogene Laherparepvec, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Tecentriq, (Atezolizumab), Temodar (Temozolomide), Temozolomide, Temsirolimus, Thalidomide, Thalomid (Thalidomide), Thioguanine, Thiotepa, Tisagenlecleucel, Tolak (Fluorouracil-Topical), Topotecan Hydrochloride, Toremifene, Torisel (Temsirolimus), Tositumomab and Iodine I 131 Tositumomab, Totect (Dexrazoxane Hydrochloride), TPF, Trabectedin, Trametinib, Trastuzumab, Treanda (Bendamustine Hydrochloride), Trifluridine and Tipiracil Hydrochloride, Trisenox (Arsenic Trioxide), Tykerb (Lapatinib Ditosylate), Unituxin (Dinutuximab), Uridine Triacetate, VAC, Vandetanib, VAMP, Varubi (Rolapitant Hydrochloride), Vectibix (Panitumumab), VeIP, Velban (Vinblastine Sulfate), Velcade (Bortezomib), Velsar (Vinblastine Sulfate), Vemurafenib, Venclexta (Venetoclax), Venetoclax, Verzenio (Abemaciclib), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Vistogard (Uridine Triacetate), Voraxaze (Glucarpidase), Vorinostat, Votrient (Pazopanib Hydrochloride), Vyxeos (Daunorubicin Hydrochloride and Cytarabine Liposome), Wellcovorin (Leucovorin Calcium), Xalkori (Crizotinib), Xeloda (Capecitabine), XELIRI, XELOX, Xgeva (Denosumab), Xofigo (Radium 223 Dichloride), Xtandi (Enzalutamide), Yervoy (Ipilimumab), Yondelis (Trabectedin), Zaltrap (Ziv-Aflibercept), Zarxio (Filgrastim), Zejula (Niraparib Tosylate Monohydrate), Zelboraf (Vemurafenib), Zevalin (Ibritumomab Tiuxetan), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib), and/or Zytiga (Abiraterone Acetate).

8. Methods of Treating Physical Insults Causing Physical or Oosttraumatic Inflammation.

Many inflammatory conditions result from physical injuries mediated by inflammation (such as, for example abrasion, puncture, laceration, contusion, including brain trauma, blunt force trauma, ischemia, surgery, transplant, sunburn, chemical burn, high temperature burn, low temperature burn, radiation). As noted above, the NTMs disclosed herein can target the nuclear transport shuttles, Imp α5 and Imp β1, that translocate SRTFs, ChREBPs, and SREBPs to the nucleus and control signal transduction pathways, which culminate in genomic reprogramming in response to trauma or burns. Thus, the novel forms of immunotherapy disclosed herein that targets nuclear import as described herein can arrest inflammation-driven organ damage associated with these physical injuries that cause swelling, redness, elevated temperature, pain, and loss of organ function. Accordingly, in one aspect, disclosed herein are methods of treating inflammation caused by physical injury (such as, for example, abrasion, puncture, laceration, contusion, blunt force trauma, ischemia, surgery, transplant, sunburn, chemical burn, high temperature burn, low temperature burn) comprising administering to a subject with a physical injury a therapeutically effective amount of a composition comprising an NTM (such as, for example, a composition comprising an NTM an NTM that comprises the sequence set forth in SEQ ID NO: 1, SEQ ID NO: 2, SEQ ID NO: 3; SEQ ID NO: 4; SEQ ID NO: 5; SEQ ID NO: 6, SEQ ID NO: 7, SEQ ID NO: 8, SEQ ID NO: 9, SEQ ID NO: 11, SEQ ID NO: 13, SEQ ID NO: 16, SEQ ID NO: 17, SEQ ID NO: 18, SEQ ID NO: 19; SEQ ID NO: 20; SEQ ID NO: 21; SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29; SEQ ID NO: 30; SEQ ID NO: 31; SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39; SEQ ID NO: 40; and/or SEQ ID NO: 41).

It is understood and herein contemplated that many inflammatory conditions resulting from injury or physical insults mediated by inflammation (such as, for example abrasion, puncture, laceration, contusion, blunt force trauma, ischemia, surgery, transplant, sunburn, chemical burn, high temperature burn, low temperature burn, radiation), said treatments will involve the treatment of a wound. Thus, in one aspect, disclosed herein are methods of treating a wound comprising contacting the wound with a therapeutically effective amount of a composition comprising a Nuclear Transport Modifier (NTM) such as, for example, an NTM that comprises the sequence set forth in SEQ ID NO: 1, SEQ ID NO: 2, SEQ ID NO: 3; SEQ ID NO: 4; SEQ ID NO: 5; SEQ ID NO: 6, SEQ ID NO: 7, SEQ ID NO: 8, SEQ ID NO: 9, SEQ ID NO: 11, SEQ ID NO: 13, SEQ ID NO: 16, SEQ ID NO: 17, SEQ ID NO: 18, SEQ ID NO: 19; SEQ ID NO: 20; SEQ ID NO: 21; SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29; SEQ ID NO: 30; SEQ ID NO: 31; SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39; SEQ ID NO: 40; and/or SEQ ID NO: 41. It is further understood, that by treating a wound with a therapeutically effective amount of a composition comprising a Nuclear Transport Modifier (NTM) not only will the wound be treated, but the time needed for the healing process can be reduced compared to untreated wounds. Thus, disclosed herein are methods of reducing the healing time of a wound comprising contacting the wound with a therapeutically effective amount of a composition comprising a Nuclear Transport Modifier (NTM) such as, for example, an NTM that comprises the sequence set forth in SEQ ID NO: 1, SEQ ID NO: 2, SEQ ID NO: 3; SEQ ID NO: 4; SEQ ID NO: 5; SEQ ID NO: 6, SEQ ID NO: 7, SEQ ID NO: 8, SEQ ID NO: 9, SEQ ID NO: 11, SEQ ID NO: 13, SEQ ID NO: 16, SEQ ID NO: 17, SEQ ID NO: 18, SEQ ID NO: 19; SEQ ID NO: 20; SEQ ID NO: 21; SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29; SEQ ID NO: 30; SEQ ID NO: 31; SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39; SEQ ID NO: 40; and/or SEQ ID NO: 41. In some aspect, the NTM can be administered orally, topically, intravenously, and/or a medicated adhesive bandage, wound dressing, surgical drape, suture, salve, cream, or wound adhesive comprising a therapeutically effective amount of a composition comprising a Nuclear Transport Modifier (NTM).

In one aspect, it is understood and herein contemplated that one way to treat a wound is through administration of the NTM subcutaneously, intramuscularly, intravenously, intranasally, topically (such as, for example, through the use of salves, creams, and/or ointments, and sprays), but also by impregnating bandages, dressing, sutures, drapes, surgical adhesive, and/or staples with the NTM. Thus, in one aspect, disclosed herein are medicated adhesive bandages, wound dressings, surgical drapes, sutures, salves, creams, lotions, or wound adhesives comprising a therapeutically effective amount of a composition comprising a Nuclear Transport Modifier (NTM) such as, for example, an NTM that comprises the sequence set forth in SEQ ID NO: 1, SEQ ID NO: 2, SEQ ID NO: 3; SEQ ID NO: 4; SEQ ID NO: 5; SEQ ID NO: 6, SEQ ID NO: 7, SEQ ID NO: 8, SEQ ID NO: 9, SEQ ID NO: 11, SEQ ID NO: 13, SEQ ID NO: 16, SEQ ID NO: 17, SEQ ID NO: 18, SEQ ID NO: 19; SEQ ID NO: 20; SEQ ID NO: 21; SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29; SEQ ID NO: 30; SEQ ID NO: 31; SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39; SEQ ID NO: 40; and/or SEQ ID NO: 41. It is understood and herein contemplated that the medicated adhesive bandages, wound dressings, surgical drapes, staples, sutures, salves, creams, or wound adhesives disclosed herein can be used in conjunction with any of the disclosed methods of treatment. Thus, in one aspect, disclosed herein are methods of treating/inhibiting/reducing a physical injury mediated by inflammation (including, but not limited to inflammatory skin disorders caused by physical insults that are mediated by inflammation), treating a wound, and/or reducing the healing time of a wound comprising administering to a subject with a wound the compositions comprising administering to the subject a therapeutically effective amount of a composition comprising a Nuclear Transport Modifier (NTM) and/or any medicated adhesive bandages, wound dressings, surgical drapes, staples, sutures, salves, lotions, creams, or wound adhesives disclosed herein.

9. Methods of Treating Microbial Disease

In response to infection with a microbe such as, for example, a virus, bacterium, fungus, or parasite, the host immune system attempts to eliminate the infecting microbe by employing arms of the innate and adaptive immune systems including the production of cytokines, antibodies, and effector mechanisms of granulocyte, monocyte, macrophage, dendritic cell, innate lymphoid cells, NK cells, NK T cells, T cells, B cells, and plasma cells. In any microbial inflammation, inflammatory signaling cascades, which are initiated by cell responses to microbial virulence factors and endogenous cytokines, culminate in nuclear translocation of Stress-Responsive Transcription Factor (SRTFs) that upregulate inflammatory gene networks. Unchecked, this genomic reprogramming (genomic storm) leads to endothelial dysfunction, multi-organ failure and ultimately fatal shock, known as septic shock, that represents the ultimate end stage of microbial inflammation, one of the 10 leading causes of death in developed and developing countries.

"Microbial inflammation" refers to a condition associated with its cardinal signs such as redness, swelling, increase in temperature, pain, and impairment of organ function such as disordered respiration as a result of the epithelial injury with adjacent microvascular endothelial injury in the lungs (and other organs) due to a microbial infection such as a virus, bacteria, fungi, or parasite. That is, "Microbial inflammation" is a mechanism of disease caused by infection ("microbial insult"). Microbial inflammation evolves from innate immune response to an infection due to a microbe such as, for example, a virus, bacterium, fungus, or parasite. Thus, the microbial injury caused by microbial virulence factors is aggravated by the host-produced inflammatory mediators that impede the clearance of invading microbes and add insult to organ's injury. It is understood and herein contemplated that the microbial inflammation and its end stage, sepsis can result from any microbial insult elicited by known (or unknown) virulence factors and microbial antigens.

The innate and adaptive immune response to infecting pathogen (disease-causing microorganism) can include the burst in production of cytokines, chemokines, and proteolytic enzymes by granulocytes, monocytes, macrophages, dendritic cells, mast cells, innate lymphoid cells, T cells, B cells, NK cells, and NK T cells. Microbial inflammation can be localized to a specific organ- or can be systemic. Microbial inflammation can proceed in stages from acute to subacute and chronic with attendant tissue destruction and subsequent fibrosis. Left unchecked, the acute microbial inflammation can lead to sepsis and septic shock, the end stage of microbial inflammation.

"Pathogen" is an agent that causes infection or disease, especially a virus, bacterium, fungus, protozoa, or parasite.

It is understood that the pathogen can be a virus. Thus in one embodiment the pathogen can be selected from the group consisting of Herpes Simplex virus-1, Herpes Simplex virus-2, Varicella-Zoster virus, Epstein-Barr virus, Cytomegalovirus, Human Herpes virus-6, Variola virus, Vesicular stomatitis virus, Hepatitis A virus, Hepatitis B virus, Hepatitis C virus, Hepatitis D virus, Hepatitis E virus, Rhinovirus, Coronavirus (including, but not limited to avian coronavirus (IBV), porcine coronavirus HKU15 (PorCoV HKU15), Porcine epidemic diarrhea virus (PEDV), HCoV-229E, HCoV-OC43, HCoV-HKU1, HCoV-NL63, SARS-CoV, SARS-CoV-2, or MERS-CoV), Influenza virus A, Influenza virus B, Measles virus, Polyomavirus, Human Papillomavirus, Respiratory syncytial virus, Adenovirus, Coxsackie virus, Chikungunya virus, Dengue virus, Mumps virus, Poliovirus, Rabies virus, Rous sarcoma virus, Reovirus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Simian Immunodeficiency virus, Human T-cell Leukemia virus type-1, Hantavirus, Rubella virus, Simian Immunodeficiency virus, Human Immunodeficiency virus type-1, and Human Immunodeficiency virus type-2.

Also disclosed are methods wherein the pathogen is a bacterium. The pathogen can be selected from the group of bacteria consisting of *Mycobacterium tuberculosis, Mycobacterium bovis, Mycobacterium bovis* strain BCG, BCG substrains, *Mycobacterium avium, Mycobacterium intracellular, Mycobacterium africanum, Mycobacterium kansasii, Mycobacterium marinum, Mycobacterium ulcerans, Mycobacterium avium* subspecies *paratuberculosis, Mycobacterium chimaera, Nocardia asteroides,* other *Nocardia* species, *Legionella pneumophila,* other *Legionella* species, *Acetinobacter baumanii, Salmonella typhi, Salmonella enterica,* other *Salmonella* species, *Shigella boydii, Shigella dysenteriae, Shigella sonnei, Shigella flexneri,* other *Shigella* species, *Yersinia pestis, Pasteurella haemolytica, Pasteurella multocida,* other *Pasteurella* species, *Actinobacillus pleuropneumoniae, Listeria monocytogenes, Listeria ivanovii, Brucella abortus,* other *Brucella* species, *Cowdria ruminantium, Borrelia burgdorferi, Bordetella avium, Bordetella pertussis, Bordetella bronchiseptica, Bordetella trematum, Bordetella hinzii, Bordetella pteri, Bordetella parapertussis, Bordetella ansorpii* other *Bordetella* species, *Burkholderia mallei, Burkholderia psuedomallei, Burkholderia cepacian, Chlamydia pneumoniae, Chlamydia trachomatis, Chlamydia psittaci, Coxiella burnetii, Rickettsial* species, *Ehrlichia* species, *Staphylococcus aureus, Staphylococcus epidermidis, Streptococcus pneumoniae, Streptococcus pyogenes, Streptococcus agalactiae, Escherichia coli, Vibrio cholerae, Campylobacter* species, *Neiserria meningitidis, Neiserria gonorrhea, Pseudomonas aeruginosa,* other *Pseudomonas* species, *Haemophilus influenzae, Haemophilus ducreyi,* other *Hemophilus* species, *Clostridium tetani,* other *Clostridium* species, *Yersinia enterolitica,* and other *Yersinia* species, and *Mycoplasma* species. In one aspect the bacteria is not *Bacillus anthracis*.

Also disclosed are methods wherein the pathogen is a fungus selected from the group of fungi consisting of *Candida albicans, Cryptococcus neoformans, Histoplasma capsulatum, Aspergillus fumigatus, Coccidiodes immitis, Paracoccidiodes brasiliensis, Blastomyces dermitidis, Pneumocystis carinii, Penicillium marneffi,* and *Alternaria alternata*.

Also disclosed are methods wherein the pathogen is a parasite selected from the group of parasitic organisms consisting of *Toxoplasma gondii, Plasmodium falciparum, Plasmodium vivax, Plasmodium malariae,* other *Plasmodium* species, *Entamoeba histolytica, Naegleria fowleri, Rhinosporidium seeberi, Giardia lamblia, Enterobius vermicularis, Enterobius gregorii, Ascaris lumbricoides, Ancylostoma duodenale, Necator americanus, Cryptosporidium* spp., *Trypanosoma brucei, Trypanosoma cruzi, Leishmania major,* other *Leishmania* species, *Diphyllobothrium latum, Hymenolepis nana, Hymenolepis diminuta, Echinococcus granulosus, Echinococcus multilocularis, Echinococcus vogeli, Echinococcus oligarthrus, Diphyllobothrium latum, Clonorchis sinensis; Clonorchis viverrini, Fasciola hepatica, Fasciola gigantica, Dicrocoelium dendriticum, Fasciolopsis buski, Metagonimus yokogawai, Opisthorchis viverrini, Opisthorchis felineus, Clonorchis sinensis, Trichomonas vaginalis, Acanthamoeba* species, *Schistosoma intercalatum, Schistosoma haematobium, Schistosoma japonicum, Schistosoma mansoni,* other *Schistosoma* species, *Trichobilharzia regenti, Trichinella spiralis, Trichinella britovi, Trichinella nelsoni, Trichinella nativa,* and *Entamoeba histolytica*.

It is understood and herein contemplated that the microbial inflammation being treated can be in any tissue, organ, or system in the subject where a microbial infection can take place, including, but not limited to the blood, brain, sinuses, upper respiratory tract, or lungs heart, bone marrow, spleen, liver, kidneys, genito-urinary tract, bladder, aural cavities, stomach, intestines, skin, eyes, teeth, or gingiva, and musculoskeletal system. Thus, in one aspect, disclosed herein are methods of treating, inhibiting, reducing, or preventing microbial inflammation at its different stages (such as, for example, acute inflammation, subacute inflammation, chronic inflammation, organ-specific inflammation, systemic inflammation, and/or sepsis and septic shock as the end stage of microbial inflammation) in a subject comprising administering to the subject an anti-microbial agent and a composition comprising one or more NTM, wherein the microbial inflammation is in the blood, brain, sinuses, upper respiratory tract, or lungs, heart, bone marrow, spleen, liver, kidneys, genito-urinary tract, bladder, aural cavities, stomach, intestines, skin, eyes, teeth, or gingiva and musculoskeletal system.

As shown herein, the disclosed NTM (such as, for example, SEQ ID NO: 1, SEQ ID NO: 2, SEQ ID NO: 3; SEQ ID NO: 4; SEQ ID NO: 5; SEQ ID NO: 6, SEQ ID NO: 7, SEQ ID NO: 8, SEQ ID NO: 9, SEQ ID NO: 11, SEQ ID NO: 13, SEQ ID NO: 16, SEQ ID NO: 17, SEQ ID NO: 18, SEQ ID NO: 19; SEQ ID NO: 20; SEQ ID NO: 21; SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29; SEQ ID NO: 30; SEQ ID NO: 31; SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39; SEQ ID NO: 40; and/or SEQ ID NO: 41) can enhance clearance of an infecting microbe even without the presence of an anti-microbial agent and without being directly microbicidal. This clearance can be the result of the ability of the NTM to control the inflammatory response so the host immune system can remove the infecting microbe whereas without the NTM, uncontrolled inflammation (such as, for example, acute inflammation, subacute inflammation, chronic inflammation, organ-specific inflammation, systemic inflammation, and/or sepsis) would proceed, increase, or continue, or by reduction of virulence factors production in the infecting pathogen such a virus, fungus, or protozoa. Accordingly, in one aspect, disclosed herein are methods of reducing the burden of a pathogenic microbe (i.e., clearing the microbe) in the blood, brain, upper respiratory tract including sinuses, and/or lungs, heart, bone marrow, spleen, liver, kidneys, genito-urinary tract, bladder, aural cavities, stomach, intestines, skin, eyes, teeth, and gingiva comprising administering to the subject a therapeutically effective amount of a composition comprising one or more NTM. In one aspect, the methods of reducing/inhibiting the presence of a pathogenic microbe (i.e., clearing the microbe) comprise administering to a subject a composition comprising an NTM but said method does not comprise the administration of an anti-microbial agent. In one aspect, the methods of reducing/inhibiting the presence of a pathogenic microbe (i.e., clearing the microbe) can further comprise the administration of an anti-microbial agent. As used herein, clearance refers to a reduction in the number of infecting microbes at a site of infection such as a tissue, organ, or system (such as for example, blood, upper respiratory tract including sinuses, and/or lungs, brain, bone marrow, spleen, liver, kidneys, genito-urinary tract, bladder, aural cavities, stomach, intestines, skin, eyes, teeth and gingiva). It is understood and herein contemplated that clearance while including the complete or partial elimination of the infecting pathogenic microbe can include less robust reductions in the infecting microbes. Thus, clearance can include such as a 10, 20, 25, 30, 33, 45, 40, 45, 50, 55, 60, 66, 70, 75, 80, 85, 90, 95, 96, 97, 98, or 99% reduction in the numbers of the infecting microbe.

It is understood and herein contemplated that the anti-inflammatory effects observed as a result of the disclosed compositions and used in the disclosed methods treating microbial inflammation can have a therapeutic effect even without the presence of any anti-microbial agent being administered in a composition with and/or in a separate composition from the NTM. Thus, in one aspect, disclosed herein are methods of treating, inhibiting, reducing, and/or preventing microbial inflammation at its different stages (such as, for example, acute inflammation, subacute inflammation, chronic inflammation, organ-specific inflammation, systemic inflammation, and/or sepsis and septic shock as the end stage of microbial inflammation) in a subject comprising an NTM (such as, for example, SEQ ID NO: 1, SEQ ID NO: 2, SEQ ID NO: 3; SEQ ID NO: 4; SEQ ID NO: 5; SEQ ID NO: 6, SEQ ID NO: 7, SEQ ID NO: 8, SEQ ID NO: 9, SEQ ID NO: 11, SEQ ID NO: 13, SEQ ID NO: 16, SEQ ID NO: 17, SEQ ID NO: 18, SEQ ID NO: 19; SEQ ID NO: 20; SEQ ID NO: 21; SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29; SEQ ID NO: 30; SEQ ID NO: 31; SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39; SEQ ID NO: 40; and/or SEQ ID NO: 41), wherein the methods does not comprise administering an anti-microbial agent either as part of the NTM composition or as a separate administration.

In one aspect, it is understood and herein contemplated that despite being able to reduce inflammation and clear microbes from host tissue, organs, or systems without administration of an anti-microbial agent, the disclosed NTM (such as, for example, SEQ ID NO: 1, SEQ ID NO: 2, SEQ ID NO: 3; SEQ ID NO: 4; SEQ ID NO: 5; SEQ ID NO: 6, SEQ ID NO: 7, SEQ ID NO: 8, SEQ ID NO: 9, SEQ ID NO: 11, SEQ ID NO: 13, SEQ ID NO: 16, SEQ ID NO: 17, SEQ ID NO: 18, SEQ ID NO: 19; SEQ ID NO: 20; SEQ ID NO: 21; SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29; SEQ ID NO: 30; SEQ ID NO: 31; SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39; SEQ ID NO: 40; and/or SEQ ID NO: 41) are not microbicidal. Thus, there can also be situations where the addition of an anti-microbial agent to the treatment regimen such as a component in the composition comprising the NTM or via a separate administration is desired. Accordingly, disclosed herein are methods of treating, inhibiting, reducing, and/or preventing microbial inflammation at its different stages (such as, for example, acute inflammation, subacute inflammation, chronic inflammation, organ-specific inflammation, systemic inflammation, and/or sepsis and septic shock as the end stage of microbial inflammation) in a subject, comprising administering to the subject an anti-microbial agent and a composition comprising one or more NTM(such as, for example, SEQ ID NO: 1, SEQ ID NO: 2, SEQ ID NO: 3; SEQ ID NO: 4; SEQ ID NO: 5; SEQ ID NO: 6, SEQ ID NO: 7, SEQ ID NO: 8, SEQ ID NO: 9, SEQ ID NO: 11, SEQ ID NO: 13, SEQ ID NO: 16, SEQ ID NO: 17, SEQ ID NO: 18, SEQ ID NO: 19; SEQ ID NO: 20; SEQ ID NO: 21; SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29; SEQ ID NO: 30; SEQ ID NO: 31; SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39; SEQ ID NO: 40; and/or SEQ ID NO: 41). The NTM and anti-microbial agent can be administered as part of the same composition or separately. Examples of anti-microbial agents include but are not limited to antibiotics, antibodies, small molecules, and functional nucleic acids (siRNA, RNAi, anti-sense oligonucleotides), that directly attack the infecting microbe or alter host conditions rendering the host system inhospitable to the microbe.

Furthermore, it is understood and herein contemplated that as the disclosed NTM (such as, for example, SEQ ID NO: 1, SEQ ID NO: 2, SEQ ID NO: 3; SEQ ID NO: 4; SEQ ID NO: 5; SEQ ID NO: 6, SEQ ID NO: 7, SEQ ID NO: 8, SEQ ID NO: 9, SEQ ID NO: 11, SEQ ID NO: 13, SEQ ID NO: 16, SEQ ID NO: 17, SEQ ID NO: 18, SEQ ID NO: 19; SEQ ID NO: 20; SEQ ID NO: 21; SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29; SEQ ID NO: 30; SEQ ID NO: 31; SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39; SEQ ID NO: 40; and/or SEQ ID NO: 41) can, without the aid of an anti-microbial agent, reduce the numbers of infecting microbes and alter the inflammatory milieu such that the host immune system can appropriately fight the infecting microbe, and as these actions are complimentary to the actions of an anti-microbial agent; one way to increase the therapeutic efficacy of an anti-microbial agent is to administer the NTM (such as, for example, SEQ ID NO: 1, SEQ ID NO: 2, SEQ ID NO: 3; SEQ ID NO: 4; SEQ ID NO: 5; SEQ ID NO: 6, SEQ ID NO: 7, SEQ ID NO: 8, SEQ ID NO: 9, SEQ ID NO: 11, SEQ ID NO: 13, SEQ ID NO: 16, SEQ ID NO: 17, SEQ ID NO: 18, SEQ ID NO: 19; SEQ ID NO: 20; SEQ ID NO: 21; SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29; SEQ ID NO: 30; SEQ ID NO: 31; SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39; SEQ ID NO: 40; and/or SEQ ID NO: 41) with the anti-microbial agent. Accordingly, disclosed herein are methods of increasing the therapeutic efficacy of an anti-microbial agent in a subject by further administering to the subject a composition comprising one or more NTM (such as, for example, SEQ ID NO: 1, SEQ ID NO: 2, SEQ ID NO: 3; SEQ ID NO: 4; SEQ ID NO: 5; SEQ ID NO: 6, SEQ ID NO: 7, SEQ ID NO: 8, SEQ ID NO: 9, SEQ ID NO: 11, SEQ ID NO: 13, SEQ ID NO: 16, SEQ ID NO: 17, SEQ ID NO: 18, SEQ ID NO: 19; SEQ ID NO: 20; SEQ ID NO: 21; SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29; SEQ ID NO: 30; SEQ ID NO: 31; SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39; SEQ ID NO: 40; and/or SEQ ID NO: 41). In some aspects of the disclosed treatment methods of increasing the therapeutic efficacy of an anti-microbial agent, an accompanying anti-microbial is a component of the NTM comprising composition. In another aspect, the anti-microbial agent is administered separately from the NTM. Administration of the anti-microbial agent can be prior to, simultaneous with, concurrent with, or following administration of the NTM composition.

It is understood and herein contemplated that despite the ability of the disclosed compositions to inhibit microbial virulence and effectuate microbial clearance in tissue without the addition of an anti-microbial agent, there can be instances where the addition (either in the composition itself or as a separate administration) of an anti-microbial is desired. Accordingly, disclosed herein are methods of treating, inhibiting, reducing, or preventing microbial inflammation in a subject, wherein the method comprises administering to the subject an anti-microbial agent.

As noted above, anti-microbial agents can comprise any antibiotics, antibodies, small molecules, and functional nucleic acids (siRNA, RNAi, anti-sense oligonucleotides), that directly attack the infecting microbe or alter host conditions rendering the host system inhospitable to the microbe. Such agents include, but are not limited to Abacavir, Acyclovir, Adefovir, Amantadine, Amprenavir, Ampligen, Arbidol, Atazanavir, Atripla, Balavir, Beta-D-N4-hydroxycitidine (NHC, EIDD-1931), Cidofovir, Combivir, Dolutegravir, Darunavir, Delavirdine, Didanosine, Docosanol, Edoxudine, Efavirenz, Emtricitabine, Enfuvirtide, Entecavir, Ecoliever, Famciclovir, Fomivirsen, Fosamprenavir, Foscarnet, Fosfonet, Ganciclovir, Hydroxychloroquine, Ibacitabine, Imunovir, Idoxuridine, Imiquimod, Indinavir, Inosine, Lamivudine, Lopinavir, Loviride, Maraviroc, Moroxydine, Methisazone, Nelfinavir, Nevirapine, Nexavir, Nitazoxanide, Norvir, Oseltamivir, Peginterferon alfa-2a, Penciclovir, Peramivir, Pleconaril, Podophyllotoxin, Raltegravir, Remdecivir, Ribavirin, Rimantadine, Ritonavir, Pyramidine, Saquinavir, Sofosbuvir, Stavudine, Telaprevir, Tenofovir, Tenofovir disoproxil, Tipranavir, Trifluridine, Trizivir, Tromantadine, Truvada, Valaciclovir, Valganciclovir, Vicriviroc, Vidarabine, Viramidine, Zalcitabine, Zanamivir, Zidovudine, Clofazimine; Dapsone; Capreomycin; Cycloserine; Ethambutol(Bs); Ethionamide; Isoniazid; Pyrazinamide; Rifampicin; Rifabutin; Rifapentine; Streptomycin; Arsphenamine; Chloramphenicol(Bs); Fosfomycin; Fusidic acid; Metronidazole; Mupirocin; Platensimycin; Quinupristin/Dalfopristin; Thiamphenicol; Tigecycline(Bs); Tinidazole; Trimethoprim(Bs); aminoglycosides such as, for example, Amikacin, Gentamicin, Kanamycin, Meropenem, Neomycin, Netilmicin, Tobramycin, Paromomycin, Streptomycin, Spectinomycin, Nitazoxanide, Melarsoprol Eflornithine, Metronidazole, Tinidazole, Miltefosine, Mebendazole, Pyrantel pamoate, Thiabendazole, Diethylcarbamazine, Ivermectin, Niclosamide, Praziquantel, Albendazole, Praziquantel, Rifampin, Amphotericin B, Fumagillin, Amphotericin B, Candicidin, Filipin, Hamycin, Natamycin, Nystatin, Rimocidin, Bifonazole, Butoconazole, Clotrimazole, Econazole, Fenticonazole, Isoconazole, Ketoconazole, Luliconazole, Miconazole, Omoconazole, Oxiconazole, Sertaconazole, Sulconazole, Tioconazole, Albaconazole, Efinaconazole, Epoxiconazole, Fluconazole, Isavuconazole, Itraconazole, Posaconazole, Propiconazole, Ravuconazole, Terconazole, Voriconazole, Abafungin, Anidulafungin, Caspofungin, Micafungin, Aurones, Benzoic acid, Ciclopirox, Flucytosine, Griseofulvin, Haloprogin, Tolnaftate, Undecylenic acid, Crystal violet, Balsam of Peru, Orotomide, Miltefosine, ansamycins, such as, for example, geldanamycin, rifaximin, herbimycin; Carbapenems, such as, for example, Ertapenem, Doripenem, Imipenem/Cilastatin, and Meropenem; Cephalosporins, such as, for example, Cefadroxil, Cefazolin, Cephradine, Cephapirin, Cephalothin, Cefalexin, Cefaclor, Cefoxitin, Cefotetan, Cefamandole, Cefmetazole, Cefonicid, Loracarbef, Cefprozil, Cefuroxime, Cefixime, Cefdinir, Cefditoren, Cefoperazone, Cefotaxime, Cefpodoxime, Ceftazidime, Ceftibuten, Ceftizoxime, Moxalactam, Ceftriaxone, Cefepime, Ceftaroline fosamil, and Ceftobiprole; Glycopeptides, such as, for example Teicoplanin, Vancomycin, Telavancin, Dalbavancin, and Oritavancin; Lincosamides(Bs), such as, for example, Clindamycin and Lincomycin; Lipopeptides, such as, for example, Daptomycin; Macrolides (Bs), such as, for example, Azithromycin, Clarithromycin, Erythromycin, Roxithromycin, Telithromycin, and Spiramycin; Monobactams, such as, for example, Aztreonam; Nitrofurans, such as, for example, Furazolidone and Nitrofurantoin(Bs); Oxazolidinones(Bs), such as, for example, Linezolid, Posizolid, Radezolid, and Torezolid; Penicillins, such as, for example, Amoxicillin, Ampicillin, Azlocillin, Dicloxacillin, Flucloxacillin, Mezlocillin, Methicillin, Nafcillin, Oxacillin, Penicillin G, Penicillin V, Piperacillin, Penicillin G, Temocillin, and Ticarcillin; Polypeptides, such as, for example, Bacitracin, Colistin, and Polymyxin B; Quinolones/Fluoroquinolones, such as, for example, Ciprofloxacin, Enoxacin, Gatifloxacin, Gemifloxacin, Levofloxacin, Lomefloxacin, Moxifloxacin, Nadifloxacin, Nalidixic acid, Norfloxacin, Ofloxacin, Trovafloxacin, Grepafloxacin, Sparfloxacin, and Temafloxacin; Sulfonamides(Bs), such as, for example, Mafenide, Sulfacetamide, Sulfadiazine, Silver sulfadiazine, Sulfadimethoxine, Sulfamethizole, Sulfamethoxazole, Sulfanilimide (archaic), Sulfasalazine, Sulfisoxazole, Trimethoprim-Sulfamethoxazole (Co-trimoxazole) (TMP-SMX), and Sulfonamidochrysoidine (archaic); Tetracyclines(Bs), such as, for example, Demeclocycline, Doxycycline, Metacycline, Minocycline, Oxytetracycline, and Tetracycline; monoclonal antibodies such as, for example, Actoxumab, Atidortoxumab, Berlimatoxumab, Bezlotoxumab, Cosfroviximab, Edobacomab, Felvizumab, Firivumab, Foravirumab, Larcaviximab, Motavizumab, Navivumab, Panobacumab, Palivizumab, Porgaviximab, CR6261, Rafivirumab, Pagibaximab, Obiltoxaximab, Ibalizumab, Regavirumab, Rmab, Sevirumab, Rivabazumab pegol, Tefibazumab, Suvratoxumab, and Tuvirumab; and checkpoint inhibitors; Pembrolizumab, Nivolumab, Atezolizumab, Avelumab, Durvalumab, pidilizumab, AMP-224, AMP-514, PDR001, cemiplimab, and Ipilimumab.

10. Methods of Treating or Preventing Inflammatory Disorders in a Mammalian Subject A typical method of treating or preventing an inflammatory disorder in a mammalian subject includes administering a composition including at least one importin alpha-selective NTM or at least one importin beta-selective NTM including an SSHR domain and a cargo, including peptides listed in Tables 1 and 2, to the mammalian subject in an amount effective for reducing importin alpha- and/or importin beta-mediated nuclear translocation of at least one transcription factor, and reducing inflammation in the mammalian subject. In the methods disclosed herein, the NTM reduces importin alpha-mediated nuclear translocation of Stress-Responsive Transcription Factor (SRTFs) that respond to inflammatory stress, and/or Carbohydrate-Responsive Element-Binding Proteins (ChREBPs) that respond to metabolic stress by binding to importin alpha. Alternatively, the NTM reduces importin beta-mediated nuclear translocation of transcription factors that respond to metabolic stress, e.g., SREBP transcription factors by binding to importin beta, respectively. Any suitable NTM can be used, e.g., one or more of the sequences disclosed herein, i.e., SEQ ID NOs: 1-9, 13, and 16-41 and/or derivatives and/or analogues thereof. The composition may be administered via any suitable route, e.g., orally, topically, intravenously, or subcutaneously. The therapeutic methods of the invention in general include administration of a therapeutically effective amount of a composition described herein to a subject (e.g., animal) in need thereof, including a mammal, particularly a human.

11. Pharmaceutical Carriers/Delivery of Pharmaceutical Products

Compositions, e.g., pharmaceutical compositions, described herein for treating inflammation disorders (such as, for example, allergic, autoimmune, metabolic, microbial, physical, and constitutive inflammation comprising organ-specific or systemic inflammation exemplified by sepsis as the end stage of microbial inflammation) including, but not limited to microbial disease, liver metabolic disease (such as, for example, alcoholic liver disease), autoimmune disease, autoinflammatory disorder, other metabolic disorder, neoplastic disorder, inflammatory skin disorder, and/or physical insults that are mediated by inflammation in a subject (e.g., a human subject) include a therapeutically effective amount of a Nuclear Transport Modifier (such as cSN50, cSN50.1, cSN50.1 beta, or a NTM as set forth in SEQ ID NO: 3, SEQ ID NO: 4, SEQ ID NO: 5, SEQ ID NO: 6, SEQ ID NO: 7, SEQ ID NO: 8, and/or SEQ ID NO: 9) sufficient for treating inflammation disorders at their different stages and location (such as, for example, acute inflammation, subacute inflammation, chronic inflammation, organ-specific inflammation, systemic inflammation, and/or sepsis and septic shock as the end stage of microbial inflammation) including, but not limited to microbial disease, liver metabolic disease (such as, for example, alcoholic liver disease), autoimmune disease, autoinflammatory disorder, other metabolic disorder, neoplastic disorder, inflammatory skin disorder, and/or physical insults that are mediated by inflammation in a subject. Similarly, compositions described herein for treating microbial inflammation in a subject (e.g., a human subject) include a therapeutically effective amount of a Nuclear Transport Modifier (such as cSN50, cSN50.1, cSN50.1 beta, or a NTM as set forth in SEQ ID NO: 3, SEQ ID NO: 4, SEQ ID NO: 5, SEQ ID NO: 6, SEQ ID NO: 7, SEQ ID NO: 8, and/or SEQ ID NO: 9) sufficient for reducing nuclear levels of a SRTFs, ChREBPs, and SREBPs in a subject with an inflammation disorder (for example, at its different stages and location (such as, for example, acute inflammation, subacute inflammation, chronic inflammation, organ-specific inflammation, systemic inflammation, and/or sepsis and septic shock as the end stage of microbial inflammation) including, but not limited to microbial disease, liver injury (such as, for example, alcoholic liver disease), autoimmune disease, autoinflammatory disorder, metabolic disorder, neoplastic disorder, inflammatory skin disorder, and/or physical insults that are mediated by inflammation) and a pharmaceutically acceptable carrier. In some aspect, the composition does not further comprise an anti-microbial agent.

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, subcutaneous injection, by intraperitoneal injection, transdermally, extracorporeally, topically or the like, including topical intranasal administration or administration by inhalant. As used herein, "topical intranasal administration" means delivery of the compositions onto any dermal or exposed mucosal surface of the nose. Delivery can include creams, lotions, salves, wound adhesives, adhesive bandage, wound dressing, surgical drape, suture, spraying mechanism or droplet mechanism, or through aerosolization. Delivery can also be directly directed to any area of the respiratory system (e.g., lungs) via intubation or inhalation. The exact amount of the compositions required will vary from subject to subject, depending on the species, age, weight and general condition of the subject, the severity of the allergic disorder being treated, the particular nucleic acid or vector used, its mode of administration and the like. Thus, an appropriate amount can be determined by one of ordinary skill in the art using only routine experimentation given the teachings herein.

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent that treats inflammatory disorders (such as, for example, allergic, autoimmune, metabolic, microbial, physical, and constitutive inflammation comprising organ-specific or systemic inflammation exemplified by sepsis and septic shock as the end stage of microbial inflammation) including, but not limited to microbial disease, liver injury (such as, for example, alcoholic liver disease), autoimmune disease, autoinflammatory disorder, metabolic disorder, neoplastic disorder, inflammatory skin disorder, and/or physical insults that are mediated by inflammation, or skin disorders, the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing agents.

The materials may be in solution, suspension (for example, incorporated into microparticles, liposomes, or cells). These may be targeted to a particular cell type via antibodies, receptors, or receptor ligands. The following references are examples of the use of this technology to target specific proteins in tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129:57-80, (1992); and Roffler, et al., Biochem. Pharmacol, 42:2062-2065, (1991)). Vehicles such as "stealth" and other antibody conjugated liposomes (including lipid mediated drug targeting to colonic carcinoma), lymphocyte directed tumor targeting such as Chimeric Antigen Receptor (CART) therapy, and highly specific therapeutic retroviral targeting of murine glioma cells in vivo. The following references are examples of the use of this technology to target specific proteins or peptides to tumor tissue (Hughes et al., *Cancer Research,* 49:6214-6220, (1989); and Litzinger and Huang, *Biochimica et Biophysica Acta,* 1104: 179-187, (1992)).

a) Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection using a two-compartment injector. The disclosed compositions can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Materials for use in the preparation of microspheres and/or microcapsules are, e.g., biodegradable/bioerodible polymers such as polygalactin, poly-(isobutyl cyanoacrylate), poly(2-hydroxyethyl-L-glutamine), and poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly (glycolic acid) or poly(ortho esters) or combinations thereof).

Formulations for oral use include tablets containing the active ingredient(s) (e.g., cSN50, cSN50.1, cSN50.1 alpha, cSN50.1 beta, or a NTM as set forth in SEQ ID NO: 3, SEQ ID NO: 4, SEQ ID NO: 5, SEQ ID NO: 6, SEQ ID NO: 7, SEQ ID NO: 8, and/or SEQ ID NO: 9) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethyl cellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material, such as, e.g., glyceryl monostearate or glyceryl distearate may be employed.

The solid tablet compositions may include a coating adapted to protect the composition from unwanted chemical changes, (e.g., chemical degradation prior to the release of the active therapeutic substance). The coating may be applied on the solid dosage form in a similar manner as that described in Swarbrick, J. and Boylan, J. C., vide supra. At least two therapeutics (e.g., a composition including cSN50, cSN50.1 or any of the NTM as set forth in SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 11, SEQ ID NO: 16, as well as any anti-microbial) may be mixed together in the tablet, or may be partitioned. In one example, the first active therapeutic is contained on the inside of the tablet, and the second active therapeutic is on the outside, such that a substantial portion of the second active therapeutic is released prior to the release of the first active therapeutic.

Formulations for oral use may also be presented as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus or a spray drying equipment. Compositions as described herein can also be formulated for inhalation and topical applications. Optionally, an anti-microbial agent may be administered in combination with the NTM; such methods are known to the skilled artisan (see, e.g., Gennaro, supra). Combinations are expected to be advantageously synergistic.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

Effective dosages and schedules for administering the compositions may be determined empirically, and making such determinations is within the skill in the art. The dosage ranges for the administration of the compositions are those large enough to produce the desired effect in which the symptoms of the disorder are affected. The dosage should not be so large as to cause adverse side effects, such as unwanted cross-reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products.

Homology/identity

It is understood that one way to define any known variants and derivatives or those that might arise, of the disclosed genes and proteins herein is through defining the variants and derivatives in terms of homology to specific known sequences. For example, SEQ ID NO: 2 sets forth a particular sequence of an NTM (cSN50.1). Specifically disclosed are variants of these and other genes and proteins herein disclosed which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent homology to the stated sequence. Those of skill in the art readily understand how to determine the homology of two proteins or nucleic acids, such as genes. For example, the homology can be calculated after aligning the two sequences so that the homology is at its highest level. As used herein, sequence homology is used interchangeably with sequence identity.

Another way of calculating homology can be performed by published algorithms Optimal alignment of sequences for comparison may be conducted by the local homology algorithm of Smith and Waterman *Adv. Appl. Math.* 2: 482 (1981), by the homology alignment algorithm of Needleman and Wunsch, *J. MoL Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment.

12. Peptides a) Peptides Derived from Protein Variants

As discussed herein there are numerous variants of the NTM that are known and herein contemplated. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Cell-penetrating fusion protein derivatives, are made by fusing a polypeptide sufficiently large to confer intracellular delivery of the targeting sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 3 and 4 and are referred to as conservative substitutions.

TABLE 3

Amino Acid Abbreviations

| Amino Acid | Abbreviations | |
|---|---|---|
| Alanine | Ala | A |
| allosoleucine | AIle | |
| Arginine | Arg | R |
| asparagine | Asn | N |
| aspartic acid | Asp | D |
| Cysteine | Cys | C |
| glutamic acid | Glu | E |
| Glutamine | Gln | Q |
| Glycine | Gly | G |
| Histidine | His | H |
| Isolelucine | Ile | I |
| Leucine | Leu | L |
| Lysine | Lys | K |
| phenylalanine | Phe | F |
| proline | Pro | P |
| pyroglutamic acid | pGlu | |
| Serine | Ser | S |
| Threonine | Thr | T |
| Tyrosine | Tyr | Y |
| Tryptophan | Trp | W |
| Valine | Val | V |

TABLE 4

Amino Acid Substitutions Original Residue Exemplary Conservative Substitutions, others are known in the art.

| | |
|---|---|
| Ala | Ser |
| Arg | Lys; Gln |
| Asn | Gln; His |
| Asp | Glu |
| Cys | Ser |
| Gln | Asn, Lys |
| Glu | Asp |
| Gly | Pro |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Substantial changes in function or immunological identity are made by selecting substitutions that are less conservative than those in Table 4, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed protein-derived peptides herein is through defining the variants and derivatives in terms of homology/identity to specific known sequences. For example, SEQ ID NO:2 sets forth a particular sequence of cSN50.1. Specifically disclosed are variants of these and other proteins herein disclosed which have at least, 70%, 75%, 80%, 85%, 90%, 91%, 92%, 93%, 94%, 95%, 96%, 97%, 98%, 99%, 99.1,%, 99.2%, 99.3%, 99.4%, 99.5%, 99.6%, 99.7%, 99.8%, 99.9%, or 100% sequence identity to the stated sequence. Those of skill in the art readily understand how to determine the homology of two proteins. For example, the homology can be calculated after aligning the two sequences so that the homology is at its highest level.

Another way of calculating homology can be performed by published algorithms Optimal alignment of sequences for comparison may be conducted by the local homology algorithm of Smith and Waterman *Adv. Appl. Math.* 2: 482 (1981), by the homology alignment algorithm of Needleman and Wunsch, *J. MoL Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989.

It is understood that the description of conservative mutations and homology can be combined together in any combination, such as embodiments that have at least 70% homology to a particular sequence wherein the variants are conservative mutations.

As this specification discusses various peptides and peptide sequences it is understood that the nucleic acids that can encode those protein-derived peptide sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence.

It is understood that there are numerous amino acid and peptide analogs which can be incorporated into the disclosed compositions. For example, there are numerous D amino acids or amino acids which have a different functional substituent then the amino acids shown in Table 3 and Table 4. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way.

Molecules can be produced that resemble peptides, but which are not connected via a natural peptide linkage. For example, linkages for amino acids or amino acid analogs can include —CH$_2$NH—, —CH$_2$S—, —CH$_2$—CH$_2$—, —CH=CH— (cis and trans), —COCH$_2$—, —CH(OH)CH$_2$—, and —CHH$_2$SO— (These and others can be found in Spatola, A. F. in *Chemistry and Biochemistry of Amino Acids, Peptides, and Proteins*, B. Weinstein, eds., Marcel Dekker, New York, p. 267 (1983); Spatola, A. F., *Vega Data* (March 1983), Vol. 1, Issue 3, Peptide Backbone Modifications (general review); Morley, *Trends Pharm Sci* (1980) pp. 463-468; Hudson, D. et al., Int J Pept Prot Res 14:177-185 (1979) (—CH$_2$NH—, CH$_2$CH$_2$—); Spatola et al. *Life Sci* 38:1243-1249 (1986) (—CH H$_2$—S); Hann *J. Chem. Soc Perkin Trans*. I307-314 (1982) (—CH—CH—, cis and trans); Almquist et al. *J. Med. Chem.* 23:1392-1398 (1980) (—COCH$_2$—); Jennings-White et al. *Tetrahedron Lett* 23:2533 (1982) (—COCH$_2$—); Szelke et al. European Appin, EP 45665 CA (1982): 97:39405 (1982) (—CH(OH)CH$_2$—); Holladay et al. *Tetrahedron*. Lett 24:4401-4404 (1983) (—C(OH)CH$_2$—); and Hruby *Life Sci* 31:189-199 (1982) (—CH$_2$—S—); each of which is incorporated herein by reference. A particularly preferred non-peptide linkage is —CH$_2$NH—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. Stapled alpha-helical sequence of signal-sequence hydrophobic region and/or other fragments used as cargo" can be used to stabilize their conformation in NTM peptides.

C. EXAMPLES

1. Example 1

Tissue injury induced by alcohol abuse constitutes a worldwide health problem. The primary targets of alcohol toxicity are the gastrointestinal system and liver. Alcoholic liver disease (ALD) characterized by infiltrating T cells in regenerating nodules, intralobular zones of inflammation, and central sclerosis, afflicts an estimated 2 million patients in the US. Among these cases, the combination of liver cirrhosis and alcoholic hepatitis contributes to an astounding 65% mortality rate over a 4-year period. This represents a toll greater than many oncologic diseases. Ethanol (EtOH)-induced hepatocellular injury involves not only excessive oxidant stress but also T cell- and Kupffer cell-mediated inflammatory responses. T cell-mediated hepatitis can be recapitulated in mice by injection of a polyclonal T cell activator, plant lectin concanavalin A (Con A), which evokes production of proinflammatory cytokines/chemokines, granulocyte accumulation in liver sinusoids, and apoptosis/necrosis of hepatocytes. It was discovered that these pathologic changes can be significantly attenuated by an innovative cell-penetrating nuclear import inhibitory peptide (cSN50) as the platform in a series of recent studies on inflammatory liver injury. Thus, the role of nuclear import adaptors in the mechanism of EtOH-altered intracellular proinflammatory and proapoptotic signaling to the nucleus can be established.

a) Investigating the Mechanism of Ethanol-Enhanced Liver Injury

It is shown herein (i) that EtOH alters homeostatic balance between these two signal transducers: (ii) that interruption of proinflammatory signaling in Kupffer cells slow down disease progression in EtOH-enhanced liver injury in the background of excessive oxidant stress and proinflammatory/proapoptotic signaling: and (iii) that the nuclear import adaptors for Stress-Responsive Transcription Factors (SRTFs) play an essential role in EtOH-associated inflammatory liver injury mediated by macrophages (Kupffer cells) and caused by endotoxic lipopolysaccharide (LPS). It was established in a modified model of EtOH-induced-liver injury mediated by T cells and caused by Con A to demonstrate EtOH deleterious effect on the biomarkers of inflammatory and apoptotic liver injury.

b) Investigating Whether Tolerance to Endotoxic LPS Changes the Outcome of EtOH-Induced Liver Injury.

The "leaky gut" hypothesis of EtOH-induced liver injury stipulates continuing transfer of LPS and other proinflammatory microbial products through ethanol-compromised intestinal mucosa to LPS-sensing liver's macrophages (Kupffer cells). These cells, in turn, produce proinflammatory cytokines/chemokines which target EtOH-compromised hepatocytes.

c) Delineating the Role of Nuclear Import Adaptors in EtOH-Enhanced Liver Injury.

Inflammatory liver injury mediated by macrophages (Kupffer cells) or T cells depends on the nuclear import of SRTFs. SRTFs regulate the genome response to proinflammatory and proapoptotic cues. The mechanism of action of cell-penetrating peptides SN50 and its cyclized analog cSN50 that inhibit the nuclear import of SRTFs is shown herein. SN50 binds to a nuclear import adaptor protein termed importin α5/karyopherin α1 (/KPNA1/SRP1) and inhibits its function as a cytoplasmic/nuclear shuttle for SRTFs. Moreover, herein it was demonstrated attenuation of proinflammatory cytokine/chemokine response by cSN50 in EtOH-fed mice challenged with LPS. However, prior to the present disclosure, it was not known how EtOH influences the importin α5/karyopherin α1 (/KPNA1/SRP1)—mediated signaling to the nucleus and genome response in hepatocytes induced by LPS or Con A. Also identified was another putative nuclear import adapter, termed SARM, which appears to participate in LPS-induced liver injury. Importantly, SARM expression is down-regulated in the liver during the process of inflammation-induced massive apoptosis. Example 2: Nuclear Import of Stress-Responsive Transcription Factors (SRTFs) Is Required for Inflammatory and Apoptotic Gene Expression.

Nuclear entry is controlled by the complex system of pores that allow free passage to small (<40 kD) karyophilic proteins. Larger proteins such as SRTFs bear a zip code denoted "nuclear localization sequence" (NLS) that is recognized by the "nuclear mail carriers" known as importins/karyopherins. These adaptor proteins, also called NLS receptors, deliver SRTFs to their nuclear site of action. As illustrated in FIG. 1, nuclear import constitutes the last signaling checkpoint before SRTFs are translocated to the nucleus. Six different human importin/karyopherin alpha adaptor proteins have been reported. Among the known importins/karyopherins, importin/karyopherin alpha 5 (SRP1/KPNA1) is the target for a cell-permeant peptide (SN50). Further studies with this new class of cell-penetrating peptide inhibitors of nuclear import allows for the development of inhibitors that target other nuclear import shuttles involved in inflammatory liver injury.

Example 9: Ethanol Feeding Enhances T Cell-Mediated Hepatitis Induced by Concanavalin A (Con A).

Figure 3:
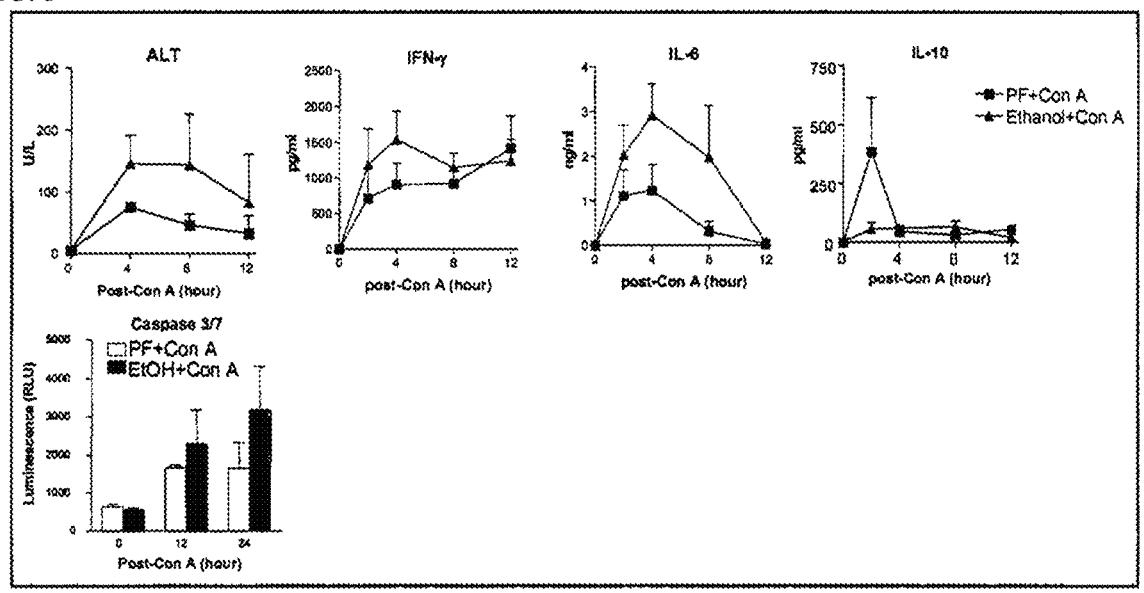
FIG. 3 shows EtOH-Enhanced liver injury caused by Concanavalin A (Con A). Elevated levels of serum hepatic enzyme ALT, plasma cytokines, and liver tissue Caspase 3/7 activity.

T cell mediated hepatitis model induced by Con A was modified to include ethanol as a potential liver injury enhancing agent. First, a range of Con A concentrations was tested to establish the threshold dose (0.5 mg/kg) which induces subclinical liver injury in C57BL/6J mice. Then, the ethanol (EtOH) feeding protocol was applied based on an experimental model of LPS-induced liver injury following ethanol exposure. Briefly, 7-week-old female C57BL-6J mice were fed control liquid diets for 3-5 days, then the mice were divided into two groups. Half were fed EtOH-containing (6%) liquid diet and half were fed similar control diet in which EtOH was substituted isocalorically with dextrin maltose. Both diets were purchased from BioServ, Inc. (Frenchtown, N.J.). During the 10-day feeding period, the control mice were pair-fed (PF) the same volume of an isocaloric of ethanol-free diet daily. At the end of the EtOH- and pair-feeding, mice received a single injection of Con A (Sigma) via tail vein. Animals were sacrificed at 12- and 24-hours post-Con A. At these time points, fragments of each liver were freeze-clamped in liquid nitrogen and stored at −80° C. until analysis. The remaining liver fragments and other organs were fixed in buffered formalin for subsequent histologic evaluation. EtOH feeding raised the level of the liver enzyme ALT and proinflammatory cytokines IL6 and IFN gamma (FIG. 3). At the same time interval, anti-inflammatory cytokine IL10 rapidly reached a peak at 2 h and then returned to the baseline (FIG. 3). Thus, EtOH feeding reversed the initial rise in anti-inflammatory cytokine, IL10, level while increasing pro-apoptotic Caspase 3/7 activity in the liver. In EtOH-fed mice (FIG. 4) multiple foci of necrosis as compared to few lesions in pair-fed controls were also demonstrated (FIG. 4). These results are in general agreement with recently published study although the contrasting pattern of EtOH-increased pro-inflammatory and anti-inflammatory cytokines was not reported therein. Cumulatively, both studies validated that EtOH feeding enhanced the extent of liver injury mediated by T cells and evoked by Con A. The current protocol is based on 10-day EtOH feeding following a 3-day adjustment to liquid diet. However, EtOH feeding can be extended to 21-day regimen to produce a "chronic" EtOH exposure with more manifestations of EtOH toxicity.

2. Example 2

Liver Apoptosis and Necrosis Induced by SEB and Mediated by T Cells is Suppressed by Nuclear Import Inhibitors As documented above, Staphylococcal immunotoxin, termed enterotoxin B, and related toxins that target T cells have the capacity to elicit systemic inflammation, liver injury, and death. Cell-penetrating peptides targeting importin/karyopherin alpha 5/KPNA1, a nuclear import adaptor protein, are delivered to T cells where they inhibit the Staphylococcal enterotoxin B-induced production of inflammatory cytokines ex vivo in cultured primary spleen cells and in vivo. The systemic production of tumor necrosis factor alpha, interferon gamma, and interleukin-6 was attenuated in mice either by a cell-penetrating cyclized form of SN50 peptide or by a transgene whose product suppresses the nuclear import of transcription factor nuclear factor/cB in T cells. The extent of liver apoptosis and hemorrhagic necrosis was also reduced, which correlated with significantly decreased mortality rates.

The protective in vivo effect of cSN50, administered during the first 12 h of SEB-induced systemic inflammation, lasts at least 72 h and does not seem to cause undesirable side effects. Taken together, the experiments highlight the in vivo efficacy of cell-penetrating peptides as nuclear import inhibitors of SRTFs involved in SEB-induced and T cell-mediated inflammatory liver injury. These findings highlight nuclear import inhibitors as a useful countermeasure for staphylococcal enterotoxin B and other toxins that trigger harmful systemic inflammatory responses.

3. Example 3

Inflammation-Associated Liver Apoptosis and Necrosis Induced by LPS and Mediated by Toll-Like Receptor 4 (TLR4)—Expressing Macrophages (Kupffer Cells) Requires Nuclear Import of SRTFs Stimulation of macrophages with LPS leads to the production of cytokines that elicit massive liver apoptosis. The in vivo role of SRTFs in this process was investigated focusing on the precipitating events that are sensitive to cSN50, a cell-permeant peptide inhibitor of SRTF nuclear import. In the absence of cSN50, mice challenged with LPS displayed very early bursts of the inflammatory cytokines/chemokines TNFα(1 h), IL-6 (2 h), IL-1/3 (2 h), and MCP-1 (2 h). Activation of both initiator caspases 8 and 9 and effector caspase 3 was noted 4 h later when full-blown DNA fragmentation and chromatin condensation were first observed (6 h). At this time, an increase of proapoptotic Bax gene expression was observed. It was preceded by a decrease of antiapoptotic Bcl2 and BclXi_gene transcripts. Massive apoptosis was accompanied by microvascular injury manifested by hemorrhagic necrosis and a precipitous drop in blood platelets observed at 6 h. An increase in fibrinogen/fibrin degradation products and a rise in plasminogen activator inhibitor 1 occurred between 4 h and 6 h. Inhibition of SRTFs nuclear import with the cSN50 peptide abrogated all these changes and increased survival from 7% to 71% (FIG. 5). Thus, the nuclear import of SRTFs induced by LPS is a prerequisite for activation of the genetic program that governs cytokines/chemokines production, liver apoptosis, microvascular injury, and death. These results can facilitate the rational design of drugs that protect the liver from inflammation-driven apoptosis.

4. Example 4

Ethanol Feeding Enhances Inflammatory Liver Injury Induced by LPS

Protective effect of Nuclear Import Inhibitor cSN50. A study was conducted herein validating that nuclear import of Stress-Responsive Transcription Factor (SRTFs) mediates EtOH-enhanced liver injury induced by LPS. As shown herein, the ethanol (EtOH) feeding protocol based on an experimental model of LPS-induced liver injury following ethanol exposure as established. At the end of the 10-day feeding period, the EtOH-fed and pair-fed (PF) control mice (C57BL/6J strain) were challenged with a single intraperitoneal (i.p.) injection of LPS (10 jug). The mice were divided into control group injected i.p. with diluent and treatment group receiving cell-penetrating nuclear import inhibitory peptide (cSN50) injected i.p. at 30 min before and 30, 90, 150, 210 min and 6, and 12 hours after LPS. The control and treated animals were sacrificed at 12 and 24 hours post-LPS. At the time of sacrifice, fragments of each liver were freeze-clamped in liquid nitrogen and stored at −80° C. until analysis. The remaining liver tissues and other organs were fixed in buffered formalin for subsequent evaluation of histology. As documented in FIG. 6, EtOH feeding enhanced substantially production of proinflammatory cytokines and chemokines (TNF alpha, IL6, and MCP1) whereas anti-inflammatory cytokine IL10 remained unchanged. Treatment with the cSN50 peptide suppressed EtOH enhanced proinflammatory cytokines and chemokine production to the baseline level. In contrast, cSN50 peptide induced an increase in anti-inflammatory cytokine IL10 which was more apparent in pair-fed rather than EtOH-fed mice. These most intriguing results are very encouraging and provide an impetus for studying the mechanism of nuclear import of SRTFs in EtOH-enhanced liver injury caused by IPS. The current protocol is based on 10-day EtOH feeding following a 3-day adjustment to liquid diet. However, EtOH feeding can be extended to a 21-day (or longer) regimen to produce a "chronic" EtOH exposure with more manifestations of EtOH toxicity.

5. Example 5

The Mechanism of Intracellular Delivery of Cell-Penetrating Peptides that Carry Membrane-Translocating Motif Based on Signal Sequence Hydrophobic Region (SSHR)

Targeting of peptides, proteins, and other functional cargo into living cells is contingent upon efficient transport across the plasma membrane barrier. The signal sequence hydrophobic region (SSHR) was harnessed to deliver functional cargoes to cultured cells and to experimental animals. Two chirally distinct forms of SSHR composed of all L or all D amino acids showed similar membrane-translocating activity as assessed by confocal microscopy, flow cytometry, and direct fluorescence measurement. An attached nuclear localization sequence ferried by the SSHR enantiomers displayed similar intracellular function by inhibiting inducible nuclear import of transcription factor nuclear factor κB (NF-κB and suppressing NF-κB-dependent gene expression of cytokines. A nuclear localization sequence comprised of a positively charged cluster of amino acids was rapidly translocated by SSHR enantiomers to the interior of unilamellar phospholipid vesicles. These findings indicate that the SSHR translocates functional peptides directly through the plasma membrane phospholipid bilayer without involving chirally specific receptor/transporter mechanisms. This mechanism of SSHR translocation is suitable for facile delivery of biologically active peptides for cell-based and animal-based functional proteomic studies. No increase in plasma membrane permeability of tested cells was observed as evidenced by fluorescein diacetate/ethidium bromide staining with a peptide concentration of up to 150 uM. Thus, SSHR-directed movement of functional cargo through the phospholipid bilayer seems to be harmless in terms of its impact on the structural integrity of the plasma membrane at concentrations sufficient to inhibit intracellular signaling. The work presented herein has demonstrated that the SSHR-based MTM possesses a number of desirable attributes. It is based on the hydrophobic region of a signal sequence that has been conserved through evolution. It translocates freely across a phospholipid bilayer, bypassing a more complex endocytic pathway apparently used by other MTMs such as Antennapedia-based or HIV TAT-based sequences.

6. Example 6

The Mechanism of Inhibition of Nuclear Import of Stress-Responsive Transcription Factors by Cell-Penetrating SN50 Peptide It is well-recognized that signaling to the nucleus plays a key role in the response of T lymphocytes to immune and inflammatory stimuli. The steps involved in this signaling include: 1) antigenic peptide-dependent activation of the TCR/CD3 complex or cytokine-dependent activation of cognate receptors; 2) signal transduction mediated by cytoplasmic kinases and phosphatases; 3) mobilization of various Stress-Responsive Transcription Factors (SRTFs), including NF-κB, NFAT, and STAT, which are sequestered in the cytoplasm, or AP-1 following its de novo synthesis; 4) import of transcription factors into the nucleus where they bind to DMA and activate transcription of a large subset of genes; and 5) nucleocytoplasmic export of some transcription factors, e.g., NFAT. Because distinct signal transduction pathways are involved in the mobilization of NF-κB, AP-1, NFAT, and STAT1 to the nucleus following agonist stimulation, it was important to determine whether a common nuclear import pathway(s) involved in signaling by each of these transcription factors can be regulated by a single NLS peptide derived from the NF-κB p50 and delivered noninvasively to the cytoplasm of Jurkat T cells. The first step in the nuclear import process is recognition of a nuclear localization sequence (NLS) within the karyophilic protein by a cytoplasmic receptor such as the importin (karyopherin)—a subunit. The NLSs of NF-κB, AP-1, and NFAT and STAT1 differ. Inducible nuclear import of NF-κB, AP-1, NFAT, and STAT1 in Jurkat T lymphocytes is significantly inhibited by a cell-penetrating peptide carrying the NLS of the NF-κB1 (p50 subunit). NLS peptide-mediated disruption of the nuclear import of these transcription factors results in inhibition of 1/cBa and IL-2 gene expression, processes dependent on NF-κB or the combination of NF-κB, AP-1, and NFAT. Further, inhibitory NLS peptide interacts with a cytoplasmic NLS receptor complex comprised of the SRP1/importin alpha 5 (karyopherin alpha1)/importin beta 1 heterodimer expressed in Jurkat T cells. Taken together, these data indicate that the inducible nuclear import of NF-κB, AP-1, NFAT, and STAT1 in Jurkat T cells can be regulated by NLS peptide delivered noninvasively to the cytoplasm to target members of the importin alpha 5 (karyopherin alpha1)/importin beta 1 NLS receptor complex.

7. Example 7

Nuclear Import Inhibitor cSN50 Attenuates Expression of ~50% LPS-Inducible Genes in the Liver Endotoxic lipopolysaccharide (LPS, endotoxin) is one of the most potent known pathogen-derived inducers of inflammation. LPS-evoked inflammatory response is dependent on expression of Toll-like receptor (TLR) 4 expressed in macrophages abundantly present in the liver and known as Kupffer cells. In response to a high dose of LPS (40 mg/kg without D-galactosamine) mice produce robustly inflammatory cytokines/chemokines and succumb within 72 hours. An extensive analysis of genes induced by a high dose of LPS in TLR4-sufficient C3H/HeN mice and TLR4-deficient C3H/HeJ mice was conducted. The induction of 1196 genes in the liver is dependent almost entirely on LPS-induced signaling through TLR4. Surprisingly, signaling to the nucleus mediated by Stress-Responsive Transcription Factor (SRTFs) plays a highly significant role in regulating the liver genome's response to proinflammatory cues evoked by LPS. Nuclear import inhibitor, cSN50 peptide, suppressed almost 50% of LPS-inducible genes in the liver. Thus, nuclear import adaptor importin/karyopherin alpha 5 (SRP1, KPNA1), which is targeted by cell-penetrating cSN50, is responsible for cytoplasmic/nuclear translocation of SRTFs and metabolic transcription factors that regulate almost half of the genes induced by LPS signaling to the nucleus through TLR4. This hitherto not reported comprehensive analysis of nuclear import-regulated genome response to proinflammatory agonist, LPS, is consistent with the demonstration of highly protective effect of cell penetrating nuclear import inhibitor cSN50 peptide in a murine model of LPS-induced lethal inflammation, apoptosis, microvascular thrombosis, and hemorrhagic necrosis. The survival of LPS (low dose)-challenged and D-galactosamine-sensitized mice was increased 10 fold (from 7% to 71%) in nuclear import inhibitor treatment group.

8. Example 8

Investigating Whether the Tolerance to Endotoxic LPS Changes the Outcome of Alcohol-Induced Liver Injury The "leaky gut" hypothesis of EtOH-induced liver injury stipulates continuing transfer of LPS and other proinflammatory microbial products through EtOH-compromised intestinal mucosa to liver's macrophages (Kupffer cells). These LPS-sensing "professional phagocytes" utilize Toll-like Receptor 4 (TLR4). The lack of functional TLR4 in C3H/HeJ mice renders them refractory to EtOH-induced liver injury. Kupffer cells can be turned into a state of LPS tolerance by engineering and delivering a physiologic inhibitor of TLR4 signaling. IL1-receptor associated kinase (IRAK)-M. This regulatory protein lacks a functional catalytic site and acts as dominant negative inhibitor of LPS- and IL1beta-induced proinflammatory signaling. IRAK-M for intracellular delivery can be enabled in cultured cells and in vivo.

Consistent with a "leaky gut" hypothesis, EtOH-induced liver injury is dependent on continuing stimulation of Kupffer cells by endotoxic lipopolysaccharide (LPS) shed from Gram-negative bacteria in the gut and entering the portal circulation through EtOH-altered intestinal mucosa. In response to LPS, Kupffer cells produce proinflammatory cytokines and chemokines which evoke proapoptotic signaling pathways in hepatocytes that are "sensitized" by oxidant stress induced by EtOH interaction with hepatocytes and other liver cells. IRAK-M, a physiologic inhibitor of LPS signaling in macrophages and other phagocytes, can render Kupffer cells "LPS tolerant" upon delivery of cell-penetrating form of this dominant negative inhibitor of LPS signaling. Thus, Kupffer cells and other LPS responders become refractory to LPS and unable to produce proinflammatory cytokines/chemokines required for inflammatory and apoptotic injury of hepatocytes. EtOH-induced oxidant stress is significantly enhanced by continuing activation of Kupffer cells. LPS tolerance reduces EtOH-related liver injury in the setting of excessive oxidant stress. This understanding can be supported by rendering SOD−/− mice refractory to LPS.

a) Rationale and Results.

There is a continuing debate concerning the mechanisms involved in EtOH-induced activation monocytes and macrophages in regard to pathogenesis of alcoholic liver injury (ALD). The prevailing view is based on significant role played by gut microbiota-derived bacterial products, exemplified by endotoxic LPS, in development of inflammatory liver injury in the context of the second ongoing process, namely, metabolic changes due to alcohol oxidation. Whether oxidant stress per se is sufficient to induce liver injury without contribution of LPS-stimulated Kupffer cells remains to be discerned. Disclosed herein is an innovative approach to control excessive stimulation of Kupffer cells by gut-derived LPS and other bacterial agonists. This approach can target signaling pathways initiated by LPS in Kupffer cells and render them "LPS tolerant" or non-responsive. While EtOH continues to exert its toxic effect on the gut and the liver cells, Kupffer cells can be prevented from generating proinflammatory and proapoptotic cytokines in response to LPS and other bacterial products that gained entry to portal circulation. IRAK-M mediates refractoriness to LPS ("endotoxin tolerance") predominantly in macrophages (e.g. Kupffer cells), dendritic cells, and other phagocytes of myelomonocytic lineage. Therefore, by engineering and delivering cell-penetrating (CP) forms of IRAK-M to Kupffer cells LPS-evoked proinflammatory signaling can be ablated in vivo in models of EtOH-induced tissue injury. CP-IRAK-M can be studied not only in EtOH-fed mice challenged with LPS or Con A, but also in Sod1−/− mice which are inherently prone to EtOH-associated liver injury due to oxidative stress. These experiments can define the role of LPS tolerance in EtOH-associated liver injury in wild type and SOD−/− mice that display an excessive oxidative stress.

9. Example 11

Suppressing EtOH-Associated Liver Injury by Targeting Relevant Nuclear Import Adaptors Herein is demonstrated that inflammatory liver injury mediated by macrophages (Kupffer cells) or T cells depends on the nuclear import of SRTFs and metabolic transcription factors SREBPs and ChREBPs. These transcription factors regulate the genome response to proinflammatory, metabolic, and proapoptotic cues. Prior studies have established the mechanism of action of SN50 and its congeners, the cell-penetrating peptides that inhibit the nuclear import of SRTFs, SREBPs and ChREBPs. SN50 and the congeners bind to a nuclear import adaptor protein termed importin/karyopherin alpha 5 (SRP1/KPNA1) and inhibit its function as a cytoplasmic/nuclear binder for SRTFs and ChREBPs whereas the binding site for importin beta exists on the SSHR of SN50 and its congeners. Also identified was another putative nuclear import adapter, termed SARM, which appears to participate in inflammatory liver injury. Importantly, SARM expression is down-regulated in the liver during the process of inflammation-induced massive apoptosis. SARM TIR domain expressed in human hepatoma cell line (HepG2) reduced Interleukin 1 beta-induced expression of the NF-κB-regulated reporter gene expression (FIG. 7). Complementary studies of importin alpha 5 (SRP1/KPNA1), importin beta 1, and SARM in hepatocytes are planned in order to understand the role of nuclear import adaptors in EtOH-associated liver injury.

Based on highly significant effect of a novel nuclear import inhibitor on inflammation associated massive liver apoptosis and necrosis in D-galactosamine-sensitized mice, nuclear import of Stress-Responsive Transcription Factor (SRTFs),Carbohydrate-Responsive Element-Binding proteins (ChREBPs), and Sterol Regulatory Element-Binding Proteins (SREBPs), can also play a significant role in EtOH associated liver injury mediated by T cells and Kupffer cells. Moreover, liver-expressed adaptor SARM, which bridges Toll-like receptors (TLRs) with nuclear import mechanism, can play a significant role in EtOH-associated liver injury.

a) Rationale and Results.

Alcoholic liver disease is associated with the action of endotoxin (lipopolysaccharide, LPS) absorbed from the gut microbiota, and oxidative stress. Both LPS and EtOH-induced metabolic changes, produce oxidative stress that activate a set of intracellular Stress-Responsive Transcription Factor (SRTFs), Carbohydrate-Responsive Element-Binding proteins (ChREBPs), and Sterol Regulatory Element-Binding Proteins (SREBPs). They are imported to the nucleus to reprogram the genome toward continuous expression of proinflammatory, metabolic, and proapoptotic mediators. At the molecular genetic level (nuclear regulome), the inflammatory response is mediated by one or more SRTFs, ChREBPs, and SREBPs that are shuttled to the nucleus by a set of adaptor proteins known as importins/karyopherins alpha/beta and possibly a new adaptor SARM. In turn, nuclear SRTFs, ChREBPs, and SREBPs activate a myriad of genes that encode inflammatory cytokines/chemokines such as TNFα, IFNγ, and MCP-1, metabolic genes responsible for hyperglycemia, and hypertriglyceridemia. The results indicate that the massive liver apoptosis and hemorrhagic necrosis, induced by bacterial lipopolysaccharide (LPS, endotoxin) or by staphylococcal immunotoxin ("superantigen"), termed enterotoxin B (SEB), are dependent on nuclear import of proinflammatory transcription factors (SRTFs) and metabolic transcription factors, ChREBPs, and SREBPs. The cSN50 peptide and its cell-penetrating congeners, prevent fatal liver injury in two experimental models. When associated with importin β1, nuclear import adaptor protein denoted importin α5/karyopherin α1 (KPNA1/SRP1) ferry proinflammatory Stress-Responsive Transcription Factor (SRTFs) to the nucleus. Importin α5 was identified as the target of the cell-penetrating peptide SN50 that prevents nuclear import of four SRTFs in human T lymphocytes. Importin β1 was identified as a sole carrier of SREBPs. Both importins, α5 and β1, are carriers of ChREBPs.

b) Experimental Design and Methods (1) Testing Nuclear Transport Modifiers of SRTFs, ChREBPs and SREBPs in Ethanol-Enhanced Model of Inflammatory Liver Injury Mediated by T cells.

The role of nuclear import of SRTFs, ChREBPs and SREBPs can be elucidated in EtOH-enhanced and T cell-mediated hepatitis induced by concanavalin A. The studies demonstrate that concanavalin A and SEB induce inflammatory liver injury in mice via a mechanism mediated by T lymphocytes. The studies indicate that EtOH-enhanced liver injury induced by LPS is attenuated by the cSN50 peptide. These advances in the suppression of nuclear import of SRTF, ChREBPs and SREBPs warrant further studies to assess the cytoprotective effect of SN50, cSN50, cSN50.1 and their congeners in EtOH-enhanced inflammatory liver injury induced by Con A and LPS using the protocols described herein.

D. REFERENCES

Akira, S. and Kaisho, T., Toll-like receptors: critical proteins linking innate and acquired immunity. Nat Immunol, 2001. 2(8): p. 675-80.

Alexander, W. S., Starr, R., Fenner, J. E., Scott, C. L., Handman, E., Sprigg, N. S., Corbin, J. E., Cornish, A. L., Darwiche, R., Owczarek, C. M., Kay, T. W., Nicola, N. A., Hertzog, P. J., Metcalf, D. and Hilton, D. J., SOCS1 is a critical inhibitor of interferon gamma signaling and prevents the potentially fatal neonatal actions of this cytokine. Cell, 1999. 98(5): p. 597-608.

Alexander, W. S., Suppressors of cytokine signaling (SOCS) in the immune system. Nat. Rev. Immunol., 2002. 2(6): p. 410-6.

Askjaer, P., Galy, V., Hannak, E. and Mattaj, I. W., Ran GTPase cycle and importins alpha and beta are essential for spindle formation and nuclear envelope assembly in living *Caenorhabditis elegans* embryos. Mol Biol Cell, 2002. 13(12): p. 4355-70.

Baldwin, A. S., Jr., The NF-kappa B and I kappa B proteins: new discoveries and insights. Annu Rev Immunol, 1996.14: p. 649-83.

Batey, R. G., Cao, Q. and Gould, B., Lymphocyte-mediated liver injury in alcohol-related hepatitis. Alcohol, 2002. 27(1): p. 37-41.

Bode, C. and Bode, J. C., Activation of the innate immune system and alcoholic liver disease: effects of ethanol per se or enhanced intestinal translocation of bacterial toxins induced by ethanol? Alcohol Clin Exp Res, 2005. 29(11 Suppl): p. 166S-71S.

Bode, J. G., Nimmesgern, A., Schmitz, J., Schaper, F., Schmitt, M., Frisch, W., Haussinger, D., Heinrich, P. C. and Graeve, L., LPS and TNFalpha induce SOCS3 mRNA and inhibit IL-6-induced activation of STATS in macrophages. FEBS Lett., 1999. 463(3): p. 365-70.

Boldin, M. P., Goncharov, T. M., Goltsev, Y. V. and Wallach, D., Involvement of MACH, a novel MORT1/FADD-interacting protease, in Fas/APO-1- and TNF receptor-induced cell death. Cell, 1996. 85(6): p. 803-15.

Bonizzi, G. and Karin, M., The two NF-kappaB activation pathways and their role in innate and adaptive immunity. Trends Immunol, 2004. 25(6): p. 280-8.

Car, B. D., Eng, V. M., Schnyder, B., Ozmen, L, Huang, S., Gallay, P., Neumann, D., Aguet, M. and Ryffel, B., Interferon gamma receptor deficient mice are resistant to endotoxic shock. J Exp Med, 1994. 179(5): p. 1437-44.

Car, B. D., Eng, V. M., Schnyder, B., Ozmen, L., Huang, S., Gallay, P., Heumann, D., Aguet, M. and Ryffel, B., Interferon gamma receptor deficient mice are resistant to endotoxic shock. J. Exp. Med., 1994. 179(5): p. 1437-1444.

Carballo, E., Lai, W. S. and Blackshear, P. J., Feedback inhibition of macrophage tumor necrosis factoralpha production by tristetraprolin. Science, 1998. 281(5379): p. 1001-5.

Chedid, A., Mendenhall, C. L., Moritz, T. E., French, S. W., Chen, T. S., Morgan, T. R., Roselle, G. A., Nemchausky, B. A., Tamburro, C. H., Schiff, E. R. and et al., Cell-mediated hepatic injury in alcoholic liver disease. Veterans Affairs Cooperative Study Group 275. Gastroenterology, 1993.105(1): p. 254-66.

Chinnaiyan, A. M., O'Rourke, K., Tewari, M. and Dixit, V. M., FADD, a novel death domain-containing protein, interacts with the death domain of Fas and initiates apoptosis. Cell, 1995. 81(4): p. 505-12.

Couillault, C., Pujol, N., Reboul, J., Sabatier, L., Guichou, J. F., Kohara, Y. and Ewbank, J. J., TLRindependent control of innate immunity in *Caenorhabditis elegans* by the TIR domain adaptor protein TIR-1, an ortholog of human SARM. Nat Immunol, 2004. 5(5): p. 488-94.

Croker, B. A., Krebs, D. L, Zhang, J. G., Wormald, S., Willson, T. A., Stanley, E. G., Robb, L, Greenhalgh, C. J., Forster, I., Clausen, B. E., Nicola, N. A., Metcalf, D., Hilton, D. J., Roberts, A. W. and Alexander, W. S., SOCS3 negatively regulates IL-6 signaling in vivo. Nat. Immunol., 2003. 4(6): p. 540-5.

Danial, N. N. and Korsmeyer, S. J., Cell death: critical control points. Cell, 2004.116(2): p. 205-219.

Dey, A. and Cederbaum, A. I., Alcohol and oxidative liver injury. Hepatology, 2006. 43(2 Suppl 1): p.S63-74.

Doerschug, K., Sanlioglu, S., Flaherty, D. M., Wilson, R. L., Yarovinsky, T., Monick, M. M., Engelhardt, J. F. and Hunninghake, G. W., First-generation adenovirus vectors shorten survival time in a murine model of sepsis. J. Immunol., 2002.169(11): p. 6539-6545.

Donald, R., Ballard, D. W. and Hawiger, J., Proteolytic processing of NF-kappa B/1 kappa B in human monocytes. ATP-dependent induction by pro-inflammatory mediators. J Biol Chem, 1995. 270(1): p. 9-12.

Fan, H. and Cook, J. A., Molecular mechanisms of endotoxin tolerance. J Endotoxin Res, 2004.10(2): p. 71-84.

Geles, K. G., Johnson, J. J., Jong, S. and Adam, S. A., A role for *Caenorhabditis elegans* importin IMA-2 in germ line and embryonic mitosis. Mol Biol Cell, 2002.13(9): p. 3138-47.

Ghosh, S. and Karin, M., Missing pieces in the NF-kappaB puzzle. Cell, 2002.109 Suppl: p. S81-96.

Gilmore, T., Gapuzan, M. E., Kalaitzidis, D. and Starczynowski, D., Rel/NF-kappa B/1 kappa B signal transduction in the generation and treatment of human cancer. Cancer Lett, 2002.181(1): p. 1-9.

Gorlich, D., Henklein, P., Laskey, R. A. and Hartmann, E., A 41 amino acid motif in importin-alpha confers binding to importin-beta and hence transit into the nucleus. Embo J, 1996.15(8): p. 1810-7.

Hawiger, J. (1999) Noninvasive intracellular delivery of functional peptides and proteins. Curr. Opin. Chem. Biol., 3:89-94.

Hawiger, J. (2001) Innate immunity and inflammation: a transcriptional paradigm. Immunol. Res., 23(2-3):99-109.

Hawiger J, Zienkiewicz J (2019) Decoding Inflammation, Its Causes, Genomic Responses, and Emerging Countermeasures. Scand. J. Immunol. e12812

Hawiger J, Veach, R A, Zienkiewicz J (2015). New Paradigms in Sepsis: From Prevention to Protection of Failing Microcirculation J. Thromb. Haemost. 13(10): 1743-56

Hawiger, J. (2002) Peptide/protein delivery in Encyclopedia of Molecular Medicine, John Wiley and Sons, 2435-2438.

Ho, Y. S., Gargano, M., Cao, J., Branson, R. T., Heimler, I. and Hutz, R. J., Reduced fertility in female mice lacking copper-zinc superoxide dismutase. J Biol Chem, 1998. 273(13): p. 7765-9.

Hong, F., Jaruga, B., Kim, W. H., Radaeva, S., E I-Assal, O, N., Tian, Z., Nguyen, V. A. and Gao, B., Opposing roles of STAT1 and STATS in T cell-mediated hepatitis: regulation by SOCS. J Clin Invest, 2002.110(10): p. 1503-13.

Ihle, J. N., STATs: signal transducers and activators of transcription. Cell, 1996. 84(3): p. 331-4.

Im, S. H. and Rao, A., Activation and deactivation of gene expression by Ca2+/calcineurin-NFATmediated signaling. Mol Cells, 2004. 18(1): p. 1-9.

Jaeschke, H., Gujral, J. S. and Bajt, M. L., Apoptosis and necrosis in liver disease. Liver Int, 2004. 24(2): p. 85-9.

Janssens, S. and Beyaert, R., Functional diversity and regulation of different interleukin-1 receptor associated kinase (IRAK) family members. Mol Cell, 2003.11(2): p. 293-302.

Jaruga, B., Hong, F., Kim, W. H. and Gao, B., IFN-gamma/STAT1 acts as a proinflammatory signal in T cell-mediated hepatitis via induction of multiple chemokines and adhesion molecules: a critical role of IRF-1. Am J Physiol Gastrointest Liver Physiol, 2004. 287(5): p. G1044-52.

Jo, D., Liu, D., Yao, S., Collins, R. D. and Hawiger, J., Intracellular protein therapy with SOCS3 inhibits inflammation and apoptosis. Nat Med, 2005.11(8): p. 892-8.

Jo, D., Nashabi, A., Doxsee, C., Lin, Q., Unutmaz, D., Chen, J. and Ruley, H. E., Epigenetic regulation of gene structure and function with a cell-permeable Cre recombinase. Nat. Biotechnol., 2001.19(10): p. 929-33.

Johnston, J. A. and O'Shea, J. J., Matching SOCS with function. Nat Immunol, 2003. 4(6): p. 507-9.

Keshavarzian, A. and Fields, J., Alcoholic liver disease: is it an "extraintestinal" complication of alcohol induced intestinal injury? J Lab Clin Med, 2003.142(5): p. 285-7.

Kessova, I. G., Ho, Y. S., Thung, S. and Cederbaum, A. I., Alcohol-induced liver injury in mice lacking Cu, Zn-superoxide dismutase. Hepatology, 2003. 38(5): p. 1136-45.

Kobayashi, K., Hernandez, L. D., Galan, J. E., Janeway, C. A., Jr., Medzhitov, R. and Flavell, R. A., IRAK M is a negative regulator of Toll-like receptor signaling. Cell, 2002.110(2): p. 191-202.

Kohler, M., Speck, C., Christiansen, M., Bischoff, F. R., Prehn, S., Haller, H., Gorlich, D. and Hartmann, E., Evidence for distinct substrate specificities of importin alpha family members in nuclear protein import. Mol Cell Biol, 1999. 19(11): p. 7782-91.

Koteish, A., Yang, S., Lin, H., Huang, X. and Diehl, A. M., Chronic ethanol exposure potentiates lipopolysaccharide liver injury despite inhibiting Jun N-terminal kinase and caspase 3 activation. J Biol Chem, 2002. 277(15): p. 13037-44.

Koziel, M. J., Cytokines in viral hepatitis. Semin Liver Dis, 1999.19(2): p. 157-69.

Krebs, D. L. and Hilton, D. J., SOCS proteins: negative regulators of cytokine signaling. Stem Cells, 2001. 19(5): p. 378-87.

Krebs, D. L. and Hilton, D. J., SOCS: physiological suppressors of cytokine signaling. J. Cell Sci., 2000. 113 (Pt16): p. 2813-9.

Kubo, M., Hanada, T. and Yoshimura, A., Suppressors of cytokine signaling and immunity. Nat Immunol, 2003. 4(12): p. 1169-76.

Kusters, S., Gantner, F., Kunstle, G. and Tiegs, G., Interferon gamma plays a critical role in T cell dependent liver injury in mice initiated by concanavalin A. Gastroenterology, 1996.111(2): p. 462-71.

Lai, W. S., Carballo, E., Thorn, J. M., Kennington, E. A. and Blackshear, P. J., Interactions of CCCH zinc finger proteins with mRNA. Binding of tristetraprolin-related zinc finger proteins to Au-rich elements and destabilization of mRNA. J Biol Chem, 2000. 275(23): p. 17827-37.

Lang, R., Pauleau, A. L., Parganas, E., Takahashi, Y., Mages, J., Ihle, J. N., Rutschman, R. and Murray, P. J., SOCS3 regulates the plasticity of gp130 signaling. Nat Immunol, 2003. 4(6): p. 546-50.

Lehmann, U., Schmitz, J., Weissenbach, M., Sobota, R. M., Hortner, M., Friederichs, K., Behrmann, I., Tsiaris, W., Sasaki, A., Schneider-Mergener, J., Yoshimura, A., Neel, B. G., Heinrich, P. C. and Schaper, F., SHP2 and SOCS3 contribute to Tyr-759-dependent attenuation of interleukin-6 signaling through gp130. J Biol Chem, 2003. 278(1): p. 661-71.

Levy, D. E. and Darnell, J. E., Jr., Stats: transcriptional control and biological impact. Nat Rev Mol Cell Biol, 2002. 3(9): p. 651-62.

Li, C., Zienkiewicz, J., Hawiger, J. Interactive sites in the MyD88 Toll/interleukin (IL) 1 receptor domain responsible for coupling to the IL1p signaling pathway. J Biol Chem. 2005, 280:26152-9

Li, P., Nijhawan, D., Budihardjo, I., Srinivasula, S. M., Ahmad, M., Alnemri, E. S. and Wang, X., Cytochrome c and dATP-dependent formation of Apaf-1/caspase-9 complex initiates an apoptotic protease cascade. Cell, 1997. 91(4): p. 479-89.

Liberati, N T., Fitzgerald, K. A., Kim, D. H., Feinbaum, R., Golenbock, D. T. and Ausubel, F. M., Requirement for a conserved Toll/interleukin-1 resistance domain protein in the Caenorhabditis elegans immune response. Proc Natl Acad Sci USA, 2004.101(17): p. 6593-8.

Lin, H. Z., Yang, S. Q., Chuckaree, C., Kuhajda, F., Ronnet, G. and Diehl, A. M., Metformin reverses fatty liver disease in obese, leptin-deficient mice. Nat Med, 2000. 6(9): p. 998-1003.

Link, A. J., Eng, J., Schieltz, D. M., Carmack, E., Mize, G. J., Morris, D. R., Garvik, B. M. and Yates, I., J. R., Direct Analysis of protein complexes using mass spectrometry. Nature Biotechnology, 1999.17: p. 676-682.

Liu, D., Li, C., Chen, Y., Burnett, C., Liu, X. Y., Downs, S., Collins, R. D. and Hawiger, J., Nuclear import of proinflammatory transcription factors is required for massive liver apoptosis induced by bacterial lipopolysaccharide. J. Biol. Chem., 2004. 279(46): p. 48434-42.

Liu, D., Liu, X. Y., Robinson, D., Burnett, C., Jackson, C., Seele, L., Veach, R. A., Downs, S., Collins, R. D., Ballard, D. W., and Hawiger, J. (2004) Suppression of staphylococcal enterotoxin B-induced toxicity by a nuclear import inhibitor. J. Biol. Chem., 279: 19239-46.

Liu D, Zienkiewicz J, DiGiandomenico A, Hawiger J. Suppression of Acute Lung Inflammation by intracellular peptide delivery of a nuclear transport inhibitor. Mol. Ther. 2009, 17(5):796-802.

Liu, X. Y., Robinson, D., Veach, R. A., Liu, D., Timmons, S., Collins, R. D. and Hawiger, J., Peptide directed suppression of a pro-inflammatory cytokine response. J Biol Chem, 2000, 275(22): p. 16774-8.

Liu Y, Veach R A, Zienkiewicz J, Boyd K L, Smith T E, Xu X Q, Wylezinski L. and Hawiger J. Protection from Endotoxin Shock by Selective Targeting of Proinflammatory Signaling to the Nucleus Mediated by Importin Alpha 5. ImmunoHorizons 2019; 3 (9),440-446.

Madge, L. A. and Pober, J. S., TNF signaling in vascular endothelial cells. Exp Mol Pathol, 2001. 70(3): p. 317-25.

Mann R E, Smart R G, and Govoni R (2003) The Epidemiology of Alcoholic Liver Disease Alcohol Research& Health Mansell, A., Smith, R., Doyle, S. L., Gray, P., Fenner, J. E., Crack, P. J., Nicholson, S. E., Hilton, D. J., O'Neill, L. A. and Hertzog, P. J., Suppressor of cytokine signaling 1 negatively regulates Toll-like receptor signaling by mediating Mal degradation. Nat Immunol, 2006. 7(2): p. 148-55.

Marine, J. C., McKay, C., Wang, D., Topham, D. J., Parganas, E., Nakajima, H., Pendeville, H., Yasukawa, H., Sasaki, A., Yoshimura, A. and Ihle, J. N., SOCS3 essential in the regulation of fetal liver erythropoiesis. Cell, 1999. 98(5): p. 617-27.

Martin, G. S., Mannino, D. M., Eaton, S. and Moss, M., The epidemiology of sepsis in the United States from 1979 through 2000. N Engl J Med, 2003. 348(16): p. 1546-54.

Matsui, H., Hikichi, Y., Tsuji, I., Yamada, T. and Shintani, Y., LIGHT, a member of the tumor necrosis factor ligand superfamily, prevents tumor necrosis factor-alpha-mediated human primary hepatocyte apoptosis, but not Fas-mediated apoptosis. J Biol Chem, 2002. 277(51): p. 50054-61.

McClain, C. J., Song, Z., Barve, S. S., Hill, D. B. and Deaciuc, I., Recent advances in alcoholic liver disease. IV. Dysregulated cytokine metabolism in alcoholic liver disease. Am J Physiol Gastrointest Liver Physiol, 2004. 287(3): p. G497-502.

McGettrick, A. F. and O'Neill, L. A., The expanding family of MyD88-like adaptors in Toll-like receptor signal transduction. Mol Immunol, 2004. 41(6-7): p. 577-82.

McMullen, M. R., Cocuzzi, E., Hatzoglou, M. and Nagy, I. E., Chronic ethanol exposure increases the binding of HuR to the TNFalpha S'-untranslated region in macrophages. J Biol Chem, 2003. 278(40): p. 38333-41.

Medzhitov, R. and Janeway, C., Jr., Innate immunity. N Engl J Med, 2000. 343(5): p. 338-44.

Melen, K., Fagerlund, R., Franke, J., Kohler, M., Kinnunen, L. and Julkunen, I., Importin alpha nuclear localization signal binding sites for STAT1, STAT2, and influenza A virus nucleoprotein. J Biol Chem, 2003. 278(30): p. 28193-200.

Mink, M., Fogelgren, B., Olszewski, K., Maroy, P. and Csiszar, K., A novel human gene (SARM) at chromosome 17q11 encodes a protein with a SAM motif and structural similarity to Armadillo/betacatenin that is conserved in mouse, *Drosophila*, and *Caenorhabditis elegans*. Genomics, 2001. 74(2): p. 234-44.

Nagy, I. E., MOLECULAR ASPECTS OF ALCOHOL METABOLISM: Transcription Factors Involved in Early Ethanol-induced Liver Injury. Annu Rev Nutr, 2004. 24: p. 55-78.

Nagy, L. E., Recent insights into the role of the innate immune system in the development of alcoholic liver disease. Exp Biol Med (Maywood), 2003. 228(8): p. 882-90.

Naka, T., Matsumoto, T., Narazaki, M., Fujimoto, M., Morita, Y., Ohsawa, Y., Saito, H., Nagasawa, T., Uchiyama, Y. and Kishimoto, T., Accelerated apoptosis of lymphocytes by augmented induction of Bax in SSI-1 (STAT-induced STAT inhibitor-1) deficient mice. ProcNatlAcadSciUSA, 1998. 95(26): p. 15577-82.

Naka, T., Tsutsui, H., Fujimoto, M., Kawazoe, Y., Kohzaki, H., Morita, Y., Nakagawa, R., Narazaki, M., Adachi, K., Yoshimoto, T., Nakanishi, K. and Kishimoto, T., SOCS-1/SS1-1-deficient NKT cells participate in severe hepatitis through dysregulated cross-talk inhibition of IFN-gamma and IL-4 signaling in vivo. Immunity, 2001.14(5): p. 535-45.

Naveau, S., Chollet-Martin, S., Dharancy, S., Mathurin, P., Jouet, P., Piquet, M. A., Davion, T., Oberti, F., Broet, P. and Emilie, D., A double-blind randomized controlled trial of infliximab associated with prednisolone in acute alcoholic hepatitis. Hepatology, 2004. 39(5): p. 1390-7.

O'Neill, L. A., Fitzgerald, K. A. and Bowie, A. G., The Toll-IL-1 receptor adaptor family grows to five members. Trends Immunol, 2003. 24(6): p. 286-90.

Pahl, H. L., Activators and target genes of Rel/NF-kappaB transcription factors. Oncogene, 1999. 18(49): p. 6853-6866.

Pfeffer, K., Matsuyama, T., Kundig, T. M., Wakeham, A., Kishihara, K., Shahinian, A., Wiegmann, K., Ohashi, P. S., Kronke, M. and Mak, T. W., Mice deficient for the 55 kd tumor necrosis factor receptor are resistant to endotoxic shock, yet succumb to L. monocytogenes infection. Cell, 1993. 73(3): p. 457-467.

Raper, S. E., Yudkoff, M., Chirmule, N., Gao, G. P., Nunes, F., Haskal, Z. J., Furth, E. E., Propert, K. J., Robinson, M. B., Magosin, S., Simoes, H., Speicher, L., Hughes, J., Tazelaar, J., Wivel, N. A., Wilson, J. M. and Batshaw, M. L., A pilot study of in vivo liver-directed gene transfer with an adenoviral vector in partial ornithine transcarbamylase deficiency. Hum. Gene Ther., 2002.13(1): p. 163-175.

Roberts, A. W., Robb, L, Rakar, S., Hartley, L, Cluse, L, Nicola, N. A., Metcalf, D., Hilton, D. J. and Alexander, W. S., Placental defects and embryonic lethality in mice lacking suppressor of cytokine signaling 3. Proc NatlAcad Sci USA, 2001. 98(16): p. 9324-9.

Rosati, O. and Martin, M. U., Identification and characterization of murine IRAK-M. Biochem Biophys Res Commun, 2002. 293(5): p. 1472-5.

Rothe, J., Lesslauer, W., Lotscher, H., Lang, Y., Koebel, P., Kontgen, F., Althage, A., Zinkernagel, R., Steinmetz, M. and Bluethmann, H., Mice lacking the tumour necrosis factor receptor 1 are resistant to TNF-mediated toxicity but highly susceptible to infection by Listeria monocytogenes. Nature, 1993. 364(6440): p. 798-802.

Schooley, K., Zhu, P., Dower, S. K. and Qwarnstrom, E. E., Regulation of nuclear translocation of nuclear factor-kappaB relA: evidence for complex dynamics at the single-cell level. Biochem J, 2003. 369(Pt2): p. 331-9.

Schwarze, S. R. and Dowdy, S. F., In vivo protein transduction: intracellular delivery of biologically active proteins, compounds and DNA. Trends Pharmacol Sci, 2000. 21(2): p. 45-8.

Seino, K., Kayagaki, N., Takeda, K., Fukao, K., Okumura, K. and Yagita, H., Contribution of Fas ligand to T cell-mediated hepatic injury in mice. Gastroenterology, 1997. 113(4): p. 1315-22.

Shayakhmetov, D. M., Li, Z. Y., Ni, S. and Lieber, A., Analysis of adenovirus sequestration in the liver, transduction of hepatic cells, and innate toxicity after injection of fiber-modified vectors. J. Virol., 2004. 78(10): p. 5368-5381.

Siegmund, S. V. and Brenner, D. A., Molecular pathogenesis of alcohol-induced hepatic fibrosis. Alcohol Clin Exp Res, 2005. 29(11 Suppl): p. 102S-109S.

Silverman, N. and Maniatis, T., NF-kappaB signaling pathways in mammalian and insect innate immunity. Genes Dev, 2001.15(18): p. 2321-42.

Song, E., Lee, S. K., Wang, J., Ince, N., Ouyang, N., Min., J., Chen, J., Shankar, P. and Lieberman, J., RNA interference targeting Fas protects mice from fulminant hepatitis. Nat Med, 2003. 9(3): p. 347-51.

Starr, R., Metcalf, D., Elefanty, A. G., Brysha, M., Willson, T. A., Nicola, N. A., Hilton, D. J. and Alexander, W. S., Liver degeneration and lymphoid deficiencies in mice lacking suppressor of cytokine signaling-1. Proc NatlAcad Sci USA, 1998. 95(24): p. 14395-9.

Stoiber, D., Kovarik, P., Cohney, S., Johnston, J. A., Steinlein, P. and Decker, T., Lipopolysaccharide induces in macrophages the synthesis of the suppressor of cytokine signaling 3 and suppresses signal transduction in response to the activating factor IFN-gamma. J. Immunol., 1999.163(5): p. 2640-7.

Takahashi, Y., Carpino, N., Cross, J. C., Torres, M., Parganas, E. and Ihle, J. N., SOCS3: an essential regulator of LIF receptor signaling in trophoblast giant cell differentiation. Embo J, 2003. 22(3): p. 372-84.

Thornberry, N. A. and Lazebnik, Y., Caspases: enemies within. Science, 1998. 281(5381): p. 1312-6.

Tiegs, G., Hentschel, J. and Wendel, A., A T cell-dependent experimental liver injury in mice inducible by concanavalin A. J Clin Invest, 1992. 90(1): p. 196-203.

Tilg, H. and Diehl, A. M., Cytokines in alcoholic and nonalcoholic steatohepatitis. N Engl J Med, 2000. 343 (20): p. 1467-76.

Torgerson, T. R., Colosia, A. D., Donahue, J. P., Lin, Y. Z. and Hawiger, J., Regulation of NF-kappa B, AP-1, NFAT, and STAT1 nuclear import in T lymphocytes by noninvasive delivery of peptide carrying the nuclear localization sequence of NF-kappa B p50. J Immunol, 1998. 161(11): p. 6084-92.

Trautwein, C., Rakemann, T., Malek, N. P., Plumpe, J., Tiegs, G. and Manns, M. P., Concanavalin Ainduced liver injury triggers hepatocyte proliferation. J Clin Invest, 1998.101(9): p. 1960-9.

Tuschl, H. and Schwab, C. E., Flow cytometric methods used as screening tests for basal toxicity of chemicals. Toxicol In Vitro, 2004. 18(4): p. 483-91.

Uesugi, T., Froh, M., Arteel, G. E., Bradford, B. U. and Thurman, R. G., Toll-like receptor 4 is involved in the mechanism of early alcohol-induced liver injury in mice. Hepatology, 2001. 34(1): p. 101-8.

Veach, R. A., Liu, D., Yao, S., Chen, Y., Liu, X. Y., Downs, S. and Hawiger, J., Receptor/transporter independent targeting of functional peptides across the plasma membrane. J. Biol. Chem., 2004. 279(12): p. 11425-31.

Venkatesh, N., Feng, Y., DeDecker, B., Yacono, P., Golan, D., Mitchison, T. and McKeon, F., Chemical genetics to identify NFAT inhibitors: potential of targeting calcium mobilization in immunosuppression. ProcNatlAcadSciUSA, 2004.101(24): p. 8969-74.

Weis, K., Regulating access to the genome: nucleocytoplasmic transport throughout the cell cycle. Cell, 2003. 112 (4): p. 441-451.

Wolter, K. G., Hsu, Y. T., Smith, C. L., Nechushtan, A., Xi, X. G. and Youle, R. J., Movement of Bax from the cytosol to mitochondria during apoptosis. J Cell Biol, 1997.139 (5): p. 1281-92.

Yasukawa, H., Ohishi, M., Mori, H., Murakami, M., Chinen, T., Aki, D., Hanada, T., Takeda, K., Akira, S., Hoshijima, M., Hirano, T., Chien, K. R. and Yoshimura, A., IL-6 induces an anti-inflammatory response in the absence of SOCS3 in macrophages. Nat Immunol, 2003. 4(6): p. 551-6.

Yoshimura, A., Mori, H., Ohishi, M., Aki, D. and Hanada, T., Negative regulation of cytokine signaling influences inflammation. CurrOpin Immunol, 2003.15(6): p. 704-8.

Zhang, J. G., Metcalf, D., Rakar, S., Asimakis, M., Greenhalgh, C. J., Willson, T. A., Starr, R., Nicholson, S. E., Carter, W., Alexander, W. S., Hilton, D. J. and Nicola, N. A., The SOCS box of suppressor of cytokine signaling-1 is important for inhibition of cytokine action in vivo. Proc. Natl. Acad. Sci. U.S.A., 2001.98(23): p. 13261-5.

Zima, T. and Kalousova, M., Oxidative stress and signal transduction pathways in alcoholic liver disease. Alcohol Clin Exp Res, 2005. 29(11 Suppl): p. 110S-115S.

What is claimed is:

1. A method of treating/inhibiting/reducing inflammatory liver injury in a subject comprising administering to the subject a therapeutically effective amount of a composition comprising a Nuclear Transport Modifier (NTM); wherein the NTM comprises the sequence set forth in SEQ ID NO: 2, SEQ ID NO: 3; SEQ ID NO: 4; SEQ ID NO: 5; SEQ ID NO: 6, SEQ ID NO: 7, SEQ ID NO: 8, SEQ ID NO: 9, SEQ ID NO: 11, SEQ ID NO: 16, SEQ ID NO: 18, SEQ ID NO: 19; SEQ ID NO: 20; SEQ ID NO: 21; SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29; SEQ ID NO: 30; SEQ ID NO: 31; SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39; SEQ ID NO: 40; and/or SEQ ID NO: 41.

2. The method of claim 1, wherein the inflammatory liver disease is caused by ethanol.

3. The method of claim 2, wherein the inflammatory liver disease is alcoholic liver disease.

4. The method of claim 1 wherein the inflammatory liver injury is caused by allergic, autoimmune, constitutive, metabolic, or physical factors.

5. The method of claim 4, wherein the physical factors comprise trauma, burn, or radiation.

* * * * *

UNITED STATES PATENT AND TRADEMARK OFFICE
CERTIFICATE OF CORRECTION

PATENT NO. : 11,571,455 B2  Page 1 of 1
APPLICATION NO. : 16/887860
DATED : February 7, 2023
INVENTOR(S) : Jack Jacek Hawiger, Jozef Zienkiewicz and Danya Liu It is certified that error appears in the above-identified patent and that said Letters Patent is hereby corrected as shown below:

In the Specification

Column 1, Line 23:
Please insert before the "BACKGROUND" paragraph:
-- "This invention was made with government support under AA015752 awarded by the National Institutes of Health. The government has certain rights in the invention." --

This certificate supersedes the Certificate of Correction issued May 29, 2020.

Signed and Sealed this
Twenty-third Day of September, 2025

John A. Squires
*Director of the United States Patent and Trademark Office*